US006054634A

United States Patent [19]
O'Malley et al.

[11] Patent Number: 6,054,634
[45] Date of Patent: Apr. 25, 2000

[54] METHODS FOR WITHIN FAMILY SELECTION IN WOODY PERENNIALS USING GENETIC MARKERS

[75] Inventors: David M. O'Malley, Cary; Ronald R. Sederoff, Raleigh, both of N.C.; Dario Grattapaglia, Brasilia, Brazil

[73] Assignee: North Caroline State University, Raleigh, N.C.

[21] Appl. No.: 08/719,337

[22] Filed: Sep. 25, 1996

Related U.S. Application Data

[63] Continuation of application No. 08/184,567, Jan. 21, 1994, abandoned.
[51] Int. Cl.$^7$ ............................... A01H 1/04; C12Q 1/00
[52] U.S. Cl. ..................... 800/267; 800/260; 800/266; 536/24.3; 435/6
[58] Field of Search .................................. 47/58, DIG. 1; 800/200; 536/24.3; 435/6

[56] References Cited

U.S. PATENT DOCUMENTS

| | | | |
|---|---|---|---|
| 5,126,239 | 6/1992 | Livak et al. | 435/6 |
| 5,385,835 | 1/1995 | Helentjaris et al. | 435/172.3 |

FOREIGN PATENT DOCUMENTS

| | | | |
|---|---|---|---|
| 0483514A1 | 5/1992 | European Pat. Off. | C12Q 1/68 |
| WO807647 | 8/1989 | WIPO | C12N 15/00 |

OTHER PUBLICATIONS

Carlson et al. Segregation of random amplified DNA markers in F1 progeny of conifers. Theoretical Applied Genetics. 83:194–200, 1991.
Tulsieram et al. Single tree genetic linkage mapping in conifers using haploid DNA from megagametophytes. Bio/technology. 10:686–690, 1992.
Neale et al. New Forests. 6:391–407, Jan. 1992.
S. Al–Janabi et al.; A Genetic Linkage Map of *Saccharum spontaneum* L. 'SES 208', *Genetics Society of Am.* 134:1249–1260 (1993).
R. Bernatzky et al.; Marker–aided selection in a backcross breeding program for resistance to chestnut blight in the American chestnut, *Can. J. For Res.* 22:1031–1035 (1992).
M. Bonierbale et al.; RFLP Maps Based on a Common Set of Clones Reveal Modes of Chromosomal Evolution in Potato and Tomato, *Genetics Society of Am.* 120:1095–1103 (1988).
H. Bradshaw, Jr. et al.; Marker–aided selection and propagation systems in trees: advantages of cloning for studying quantitative inheritance, *Can. J. For. Res.* 22:1044–1049 (1992).
J. Carlson et al.; Segregation of random amplified DNA markers in F $_1$ progeny of conifers, *Theor Appl Genet* 83:194–200 (1991).
J. DaSilva et al.; RFLP linkage map and genome analysis of *Saccharum spontaneum*, *Genome* 36: 782–791 (1993).

P. Fritsch et al.; High outcrossing rates maintain male and hermaphrodite individuals in populations of the flowing plant *Datisca glomerata*, *Letters to Nature* 359:633–636 (1992).
C. Gebhardt et al.; RFLP analysis and linkage mapping in *Solanum tuberosum Theor Appl Genet* 78:65–75 (1989).
D. Grattapaglia et al.; Mapping Genomic Regions Controlling Economically Important Traits in Eucalyptus, (Abstract) *Western Forest Genetics Association Annual Meeting*, Oahu, Hawaii (Oct. 1993).
D. Grattapaglia et al.; Genetic Mapping of QTL's Controlling Volume Growth, Vegetative Propagation and Wood Quality Traits in *Eucalyptus grandis* and *E. urophylla*, (Abstract for Plant Genome II) (Jan. 1994).
D. Grattapaglia et al.; QTL Mapping in Eucalyptus Using Pseudo–Testcross RAPD Maps, Half and Full–Sib Families, (Abstract for SFTIC) (Atlanta 1993).
K. Kazan et al.; Inheritance of random amplified plymorphic DNA markers in an interspecific cross in the genus Stylosanthes, *Genome* 36:50–56 (1993).
W. Nance et al.; Potential applications of molecular markers for genetic analysis of host–pathogen systems in forest trees, *Can. J. for Res* 22:1036–1043 (1992).
D. Neale et al.; Restriction fragment length polymorphism mapping in conifers and applications to forest genetics and tree improvement, *Can. J. for Res.* 21:545–554 (1991).
R. Nodari et al.; Towards an integrated linkage map of common bean 2. Development of an RFLP–based linkage map, *Theor Appl Genet* 85:513–520 (1993).
A. Paterson et al.; Mendelian Factors Underlying Quantitative Traits in Tomato: Comparison Across Species, Generations, and Environments, *Genetics Society of Am.* 127:181–197 (1991).
E. Ritter et al.; Estimation of Recombination Frequencies and Construction of RFLP Linkage Maps in Plants from Crosses Between Heterozygous Parents, *Genetics* 125:645–654 (1990).
A. Roy et al.; Segregating random and amplified polymorphic DNA's (RAPDS) in *Betula alleghaniensis*, *Theor Appl Genet* 85:173–180 (1992).
B. Sobral et al.; High output genetic mapping of polyploids using PCR–generated markers, *Theor Appl Genet* 86:105–112 (1993).
S. Strauss et al.; Limitations of molecular–marker–aided selection in forest tree breeding, *Can. J. for Res.* 22:1050–1061 (1992).

(List continued on next page.)

*Primary Examiner*—Douglas W. Robinson
*Assistant Examiner*—Melissa L. Kimball
*Attorney, Agent, or Firm*—Myers Bigel Sibley & Sajovec

[57] ABSTRACT

A method using genetic markers to determine whether a quantitative trait is a heritable oligogenic trait in a woody perennial plant. The method is useful in trees where a three-generation pedigree is not available. Exemplary quantitative traits include disease resistance and wood volume. Methods of selecting, propagating and breeding plants are also provided.

2 Claims, 33 Drawing Sheets

OTHER PUBLICATIONS

C. Tauer et al.; Using marker–aided selection to improve tree growth response to abiotic stress, *Can J. for Res.* 22:1018–1029 (1992).

C. Vallejos et al.; A Molecular Marker–Based Linkage Map of *Phaseolus vulgaris* L., *Genetics Society of Am.* 131:733–740 (1992).

J. Welsh et al.; Polymorphisms generated by arbitrarily primed PCR in the mouse: application to strain identification and genetic mapping, *Nucleic Acids Research* 2:303–306 (1991).

J. William et al.; DNA polymorphisms amplified by arbitrary primers are useful as genetic markers, *Nucleic Acids Research* 18:6531–6535 (1990).

C. Williams et al.; Conifer wood quality and marker–aided selection: a case study, *Can. J. for Res.* 22:1009–1017 (1992).

K. Wu et al.; The detection and estimation of linkage in polyploids using single–dose restriction fragments, *Theor Appl Genet* 83:294–300 (1992).

D. Grattapaglia et al.; RAPD Mapping and Tree Improvement, Abstract #29, *Plant Genome I: The International Conference on the Plant Genome*, Nov. 9–11, 1992, San Diego, CA.

D. Grattapaglia et al.; Pseudo–Testcross Mapping Strategy in Forest Trees: Single Tree RAPD Maps of *Eucalyptus grandis* and *E. urophylla*, Abstract #47, *Plant Genome I: The International Conference on the Plant Genome*, Nov. 9–11, 1992, San Diego, CA.

A. Groover et al.; Mapping of Quantitative Trait Loci Influencing Wood Specific Gravity in Loblolly Pine (*Pinus taeda*), Abstract #48, *Plant Genome I: The International Conference on the Plant Genome*, Nov. 9–11, 1992, San Diego, CA.

D. Lawson et al.; Identification of Genes Influencing Morphological and Physiological Traits in Apple, Abstract #148, *Plant Genome I: The International Conference on the Plant Genome*, Nov. 9–11, 1992, San Diego, CA.

H. Bradshaw et al.; Genetic Mapping in Populus, Abstract#1, *Plant Genome I: The International Conference on the Plant Genome*, Nov. 9–11, 1992, San Diego, CA. (Forest Tree Workshop).

M. Devey et al.; Identification of RAPD Markers Linked with a Major Gene for Resistance to White Pine Blister Rust in Sugar Pine, Abstract #3, *Plant Genome I: The International Conference on the Plant Genome*, Nov. 9–11, 1992, San Diego, CA. (Forest Tree Workshop).

D. Grattapaglia et al.; Pseudo–Testcross Mapping Strategy in Forest Trees: Single Tree RAPD Maps of *Eucalyptus grandis* and *E. urophylla*, Abstract #4, *Plant Genome I: The International Conference on the Plant Genome*, Nov. 9–11, 1992, San Diego, CA. (Forest Tree Workshop).

G. Moran et al.; Molecular Marker Maps in *Pinus Radiata* and *Eucalyptus Nitens* for Application in Tree Breeding Programs, Abstract #10, *Plant Genome I: The International Conference on the Plant Genome*, Nov. 9–11, 1992, San Diego, CA. (Forest Tree Workshop).

D. O'Malley et al.; QTL Mapping in Loblolly Pine Using RAPDs, Abstract #12, *Plant Genome I: The International Conference on the Plant Genome*, Nov. 9–11, 1992, San Diego, CA. (Forest Tree Workshop).

L. Eldredge et al., Application of RFLP Analysis to Genetic Linkage Mapping in Peaches, *HortScience* 27, 160–163 (1992).

Paterson et al. 1991. Advances in Agronomy. 46:40–90.

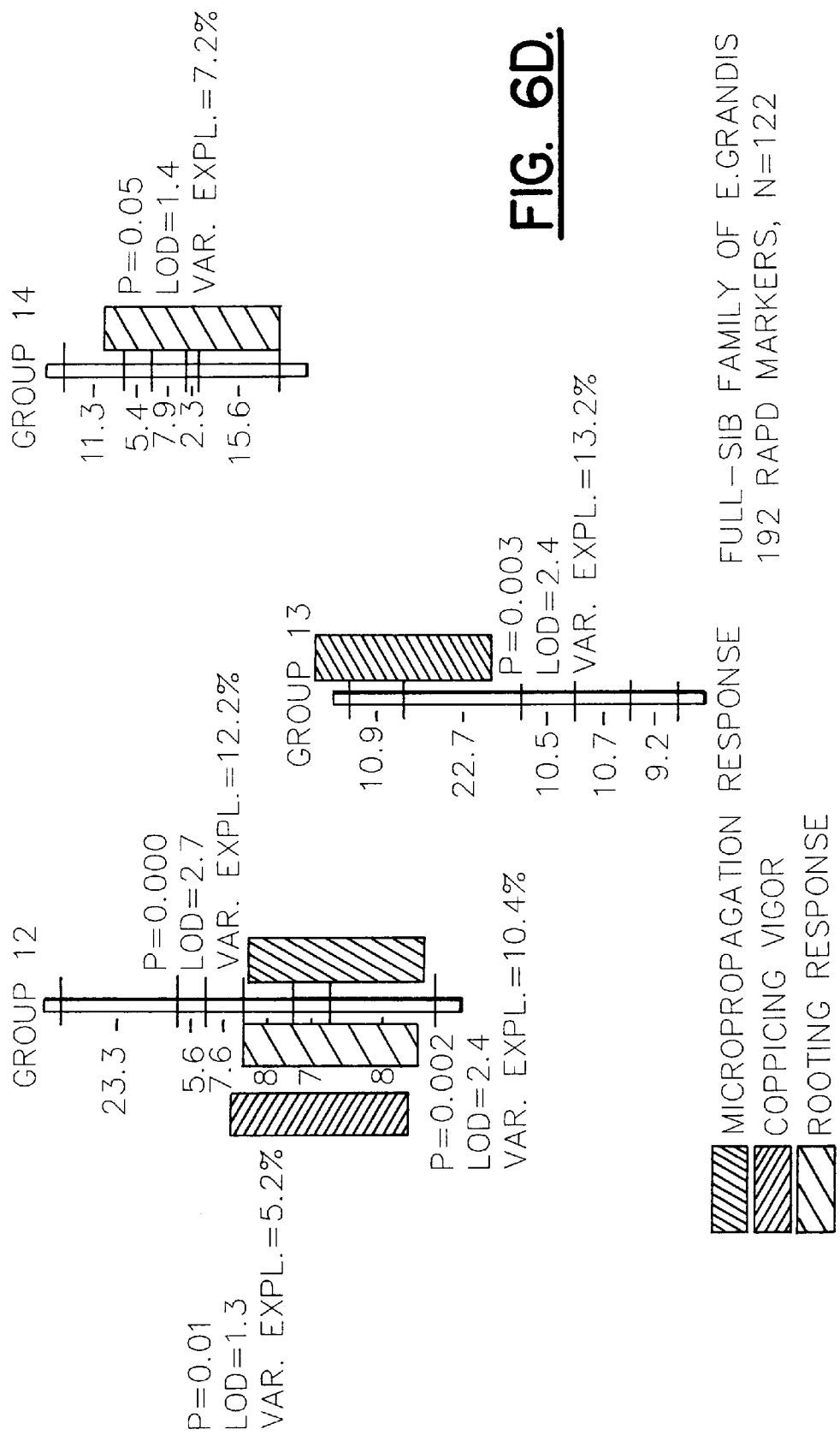

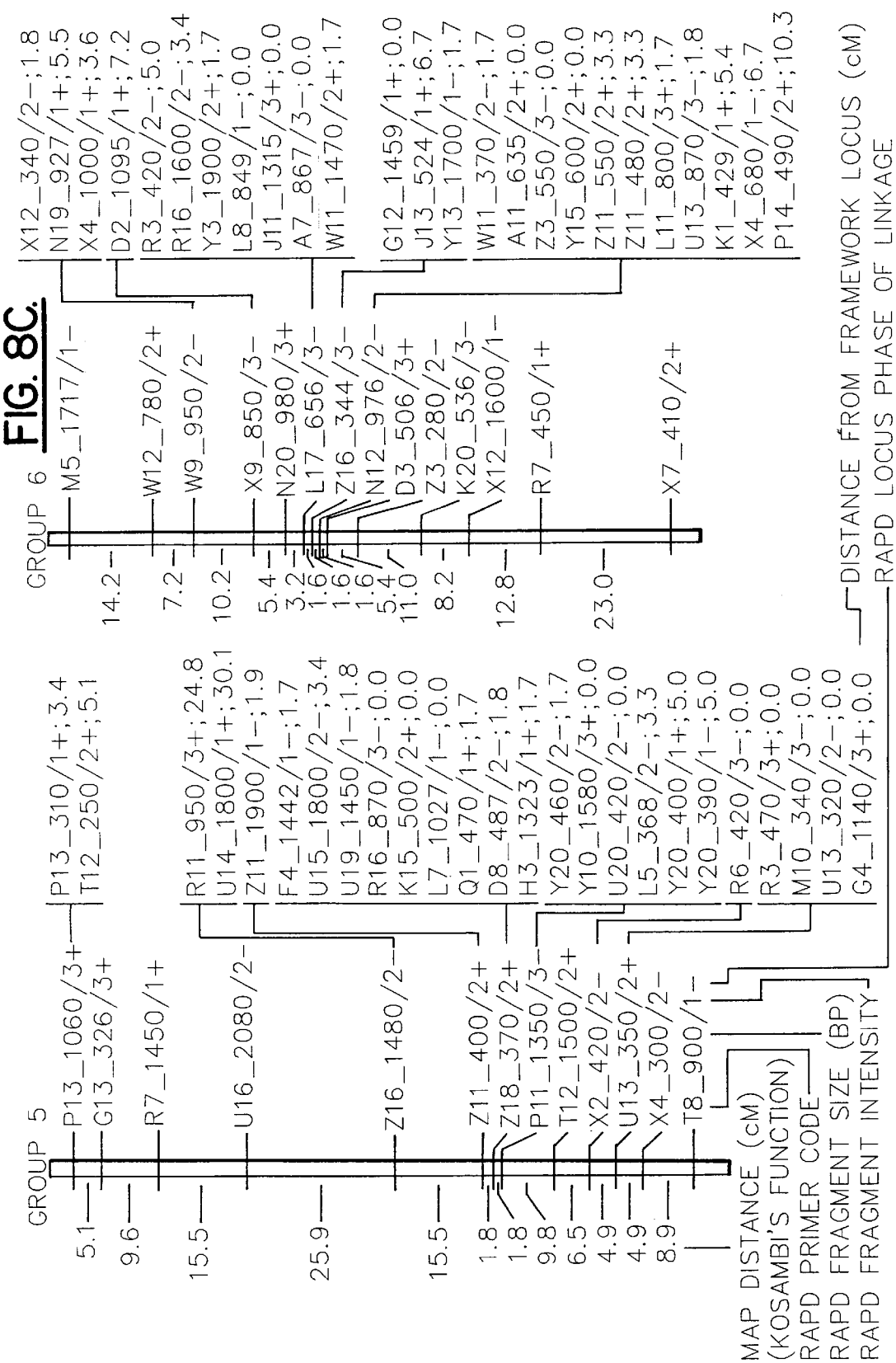

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CTCCACACGG                                                                          10

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CATTCGAGCC                                                                          10

(2) INFORMATION FOR SEQ ID NO:3:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

AGCGCCATTG                                                                          10

(2) INFORMATION FOR SEQ ID NO:4:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:4:

CCTCTCGACA                                                                          10

(2) INFORMATION FOR SEQ ID NO:5:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:5:

CCGAACACGG 10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TGTCATCCCC 10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CCCAGCTGTG 10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GAACGGACTC 10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TCAACGGGAC 10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GGAGTGGACA 10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CTGATGCGTG                                                        10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CCAGCTTAGG                                                        10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTGCGCTGGA                                                        10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GTGCAACGTG                                                        10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AGTCACTCCC                                                        10

(2) INFORMATION FOR SEQ ID NO:16:

(i) SEQUENCE CHARACTERISTICS:
        (A) LENGTH: 10 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

ACAGCCTGCT                                                              10

(2) INFORMATION FOR SEQ ID NO:17:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

TCCCGCCTAC                                                              10

(2) INFORMATION FOR SEQ ID NO:18:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

CCCGTAGCAC                                                              10

(2) INFORMATION FOR SEQ ID NO:19:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:19:

CTGGGCACGA                                                              10

(2) INFORMATION FOR SEQ ID NO:20:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:20:

GAAGCCAGCC                                                              10

(2) INFORMATION FOR SEQ ID NO:21:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

GACGTGGTGA                                                                      10

(2) INFORMATION FOR SEQ ID NO:22:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:22:

CAATCGCCGT                                                                      10

(2) INFORMATION FOR SEQ ID NO:23:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:23:

ACCTCGGCAC                                                                      10

(2) INFORMATION FOR SEQ ID NO:24:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:24:

TTCCGCCACC                                                                      10

(2) INFORMATION FOR SEQ ID NO:25:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:25:

AGTCGCCCTT                                                                      10

(2) INFORMATION FOR SEQ ID NO:26:

(i) SEQUENCE CHARACTERISTICS:
              (A) LENGTH: 10 base pairs
              (B) TYPE: nucleic acid
              (C) STRANDEDNESS: single
              (D) TOPOLOGY: linear -continued

```
    (ii) MOLECULE TYPE: cDNA (xi) SEQUENCE DESCRIPTION: SEQ ID NO:26:

AGGGTCTGTG                                                                     10
```

METHODS FOR WITHIN FAMILY SELECTION IN WOODY PERENNIALS USING GENETIC MARKERS

This application is a continuation of application Ser. No. 08/184,567, filed Jan. 21, 1994 now abandoned.

FIELD OF THE INVENTION

The present invention relates to methods of selecting genetically superior individual plants using molecular markers, and to the breeding of plants to enhance desirable characteristics. The present invention particularly relates to the use of these methods in woody perennials such as forest trees.

BACKGROUND OF THE INVENTION

Current practice in forest tree breeding relies on phenotypic selection, a time-consuming process. Genetic analysis of woody plants is hindered by the long generation times, non-domestication, high levels of genetic diversity and large size of the plants in question. Additionally, little is known about the mode of inheritance for most traits of interest in forest trees. Tree breeding is made more difficult as, in addition to the long generation times, certain traits of interest such as wood properties change during growth and maturation. Methods that allow the early selection of genetically superior individual trees would be of value in programs to improve tree stock.

The use of isozyme markers has been used to explore genetic variation in forest tree populations. The method is limited, however, by the small number of enzymes for which assays are available (Conkle 1981). The scope of genetic analysis for forest trees was extended by the development of restriction fragment length polymorphisms (RFLPs). However, the analysis of RFLP markers is laborious and limiting.

SUMMARY OF THE INVENTION

Disclosed is a method of determining whether a quantitative trait is a heritable oligogenic trait in a woody perennial plant, the plant selected from the group consisting of species exhibiting high genetic variability and hybrids exhibiting high genetic variability. The method comprises the steps of (a) choosing a sexually mature woody perennial parent plant; (b) obtaining a plurality of progeny of said parent plant (the parent and the progeny together comprising a plant family, and the progeny being either full sib progeny, half-sib progeny, or selfed progeny); (c) constructing a genomic map of the plant family using a plurality of genetic markers, the genetic markers segregating in an essentially Mendelian ratio and showing linkage with the other markers; (d) grouping progeny into classes based on the allelic state of a marker; (e) measuring the quantitative trait in each of said progeny; (f) determining the mean of the quantitative trait in each of the classes of progeny; and (g) determining statistically whether said means of said classes differ significantly, wherein a significant difference among means of said classes indicates said trait is a heritable oligogenic trait.

Another aspect of the present invention is the above method, further comprising repeating steps (d)–(g) for additional markers.

Further aspects of the present invention are methods as describe above, wherein the woody perennial plant is a tree of the order Coniferae, or is selected from among Picea species, loblolly pine, lodgepole pine, longleaf pine, Monterey pine, and balsam fir. Further aspects of the present invention are methods as described above where the plant is selected from among Eucalyptus species or from among the genuses Liquidamber, Liriodendron, Populus, and Prunus.

Another aspect of the present invention is a method as described above, wherein said step of constructing a genomic map is carried out by random amplified polymorphic DNA (RAPD) analysis.

An aspect of the present invention is a method of determining whether a quantitative trait is a heritable oligogenic trait in a woody perennial plant, wherein the quantitative trait is selected from among wood volume, wood specific gravity, disease resistance, height, diameter and growth. The method may be directed to a tree of the genus Pinus and the quantitative trait of resistance to fusiform rust disease.

A further aspect of the present invention is a method for selecting individual woody perennial plants from within a family useful for breeding, comprising: (a) choosing a sexually mature woody perennial parent plant; (b) obtaining a plurality of progeny of said parent plant, the parent and progeny together comprising a plant family and the progeny being either full sib progeny, half-sib progeny, or selfed progeny; (c) constructing a genomic map of said plant family using a plurality of genetic markers, said genetic markers segregating in an essentially Mendelian ratio and showing linkage with the other markers; (d) grouping said progeny into classes based on the allelic state of a marker; (e) measuring said quantitative trait in each of said progeny; (f) determining the mean of said quantitative trait in each of said classes of progeny; (g) determining statistically whether said means of said classes differ significantly, a significant difference among means of said classes indicating said trait is a heritable oligogenic trait; (h) associating at least one of said genetic markers with a preselected desirable heritable oligogenic trait to provide at least one quantitative trait loci associated with said trait; and (i) selecting progeny from said family containing said quantitative trait loci; wherein said selected progeny carry a gene for said desirable trait.

Further aspects of the present invention include this method and further include the step of propagating the selected progeny; propagation may be by somatic embryogenesis.

A further aspect of the present invention is a method of breeding woody perennial plants to increase the mean measurement of a chosen quantitative trait, comprising: (a) choosing a sexually mature woody perennial parent plant; (b) obtaining a plurality of progeny of said parent plant, the parent and said progeny comprising a plant family and progeny being selected from the group consisting of full sib progeny, half-sib progeny, and selfed progeny; (c) constructing a genomic map of said plant family using a plurality of genetic markers, said genetic markers segregating in an essentially Mendelian ratio and showing linkage with the other markers; (d) grouping said progeny into classes based on the allelic state of a marker; (e) measuring said quantitative trait in each of said progeny; (f) determining the mean of said quantitative trait in each of said classes of progeny; (g) determining statistically whether said means of said classes differ significantly, a significant difference among means of said classes indicating said trait is a heritable oligogenic trait; (h) associating at least one of said genetic markers with a preselected desirable heritable oligogenic trait to provide at least one quantitative trait loci associated with said trait; (i) selecting progeny from said family containing said quantitative trait loci; and (j) propagating said selected progeny to produce progeny which retain said predetermined trait.

A further aspect of the present invention is a method of selecting a Pinus taeda tree useful for breeding Pinus taeda trees resistant to fusiform rust disease, comprising the steps of (a) choosing a sexually mature Pinus taeda parent tree; (b) obtaining a plurality of progeny of said parent tree, said parent tree and said progeny together comprising a family, said progeny being either full sib progeny, half-sib progeny, or selfed progeny; (c) constructing a genomic map of said Pinus taeda family using a plurality of genetic markers, said genetic markers segregating in an essentially Mendelian ratio and showing linkage with the other markers; (d) grouping said progeny into classes based on the allelic state of a marker; (e) measuring resistance to fusiform rust disease in each of said progeny; (f) determining the mean of said measurements in each of said classes of progeny; (g) determining statistically whether said means of said classes differ significantly, a significant difference among means of said classes indicating resistance to fusiform rust disease is a heritable oligogenic trait; (h) associating at least one of said genetic markers with resistance to fusiform rust disease to provide at least one quantitative trait loci associated with said resistance; and (i) selecting a progeny tree containing said quantitative trait loci; wherein said selected progeny tree carries a gene for resistance to fusiform rust disease.

A further aspect of the present invention is a method of breeding Pinus taeda trees for resistance to fusiform rust disease, comprising (a) choosing a sexually mature Pinus taeda parent tree; (b) obtaining a plurality of progeny of said parent tree, said parent tree and said progeny together comprising a family, said progeny being either full sib progeny, half-sib progeny, or selfed progeny; (c) constructing a genomic map of said Pinus taeda family using a plurality of genetic markers, said genetic markers segregating in an essentially Mendelian ratio and showing linkage with the other markers; (d) grouping said progeny into classes based on the allelic state of a marker; (e) measuring resistance to fusiform rust disease in each of said progeny; (f) determining the mean of said measurements in each of said classes of progeny; (g) determining statistically whether said means of said classes differ significantly, a significant difference among means of said classes indicating resistance to fusiform rust disease is a heritable oligogenic trait; (h) associating at least one of said genetic markers with resistance to fusiform rust disease to provide at least one quantitative trait loci associated with said resistance; (i) selecting a progeny tree containing said quantitative trait loci; (j) propagating said selected progeny tree to produce progeny trees which retain said resistance to fusiform rust disease.

A further aspect of the present invention is a method of selecting a Eucalyptus tree useful for breeding Eucalyptus trees having increased wood volume, comprising: (a) choosing a sexually mature Eucalyptus parent tree; (b) obtaining a plurality of progeny of said parent tree, said parent tree and said progeny together comprising a family, said progeny being either full sib progeny, half-sib progeny, or selfed progeny, (c) constructing a genomic map of said Eucalyptus family using a plurality of genetic markers, said genetic markers segregating in an essentially Mendelian ratio and showing linkage with the other markers; (d) grouping said progeny into classes based on the allelic state of a marker; (e) measuring wood volume in each of said progeny; (f) determining the mean of said measurements in each of said classes of progeny; (g) determining statistically whether said means of said classes differ significantly, a significant difference among means of said classes indicating increased wood volume is a heritable oligogenic trait; (h) associating at least one of said genetic markers with increased wood volume to provide at least one quantitative trait loci associated with wood volume; and (i) selecting a progeny tree containing said quantitative trait loci, wherein said selected progeny tree carries a gene for increased wood volume.

A further aspect of the present invention is a method of breeding Eucalyptus trees for increased wood volume, comprising: (a) choosing a sexually mature Eucalyptus parent tree; (b) obtaining a plurality of progeny of said parent tree, said parent tree and said progeny together comprising a family, said progeny being either full sib progeny, half-sib progeny, or selfed progeny; (c) constructing a genomic map of said Eucalyptus family using a plurality of genetic markers, said genetic markers segregating in an essentially Mendelian ratio and showing linkage with the other markers; (d) grouping said progeny into classes based on the allelic state of a marker; (e) measuring wood volume in each of said progeny; (f) determining the mean of said measurements in each of said classes of progeny, (g) determining statistically whether said means of said classes differ significantly, a significant difference among means of said classes indicating increased wood volume is a heritable oligogenic trait; (h) associating at least one of said genetic markers with increased wood volume to provide at least one quantitative trait loci associated with increased wood volume; (i) selecting a progeny tree containing said quantitative trait loci; (j) propagating said selected progeny tree to produce progeny trees which retain said increased wood volume. A further aspect of the present invention is wood and wood pulp produced from Eucalyptus trees produced according to the methods described above.

BRIEF DESCRIPTION OF THE DRAWINGS

FIGS. 6A–6D together comprise a genomic map of an *E. grandis* individual showing markers representing most regions of the genome, and showing the approximate locations of markers that are statistically associated with quantitative traits of progeny in a half-sib family. These regions of strong marker: trait association are indicative of the existence of one or more QTL in these regions.

FIGS. 8A–8F together comprise the linkage map of *Eucalyptus urophylla* clone 28. Linkage relationships of 251 RAPD markers in 11 linkage groups were estabished at a threshold LOD score 5.0 and maximum γ=0.25. A framework map of 119 loci or loci clusters (indicated in bold letters along the linkage groups) that could be ordered with a likelihood support ≧1000:1 was assembled covering 95.2% of the estimated genome size. RAPD marker loci that could not be ordered with equal confidence were designated as accessory markers and are listed on the right of the linkage groups along with the approximate cM distance to the closest framework locus. RAPD marker loci are identified by Operon Technologies primer code (see above), fragment size in base pairs, fragment amplification density and linkage phase (+ or −). A RAPD marker locus showing a significant distortion from 1:1 segregation ratio is indicated by an asterisk.

DETAILED DESCRIPTION OF THE INVENTION

Figure 1:
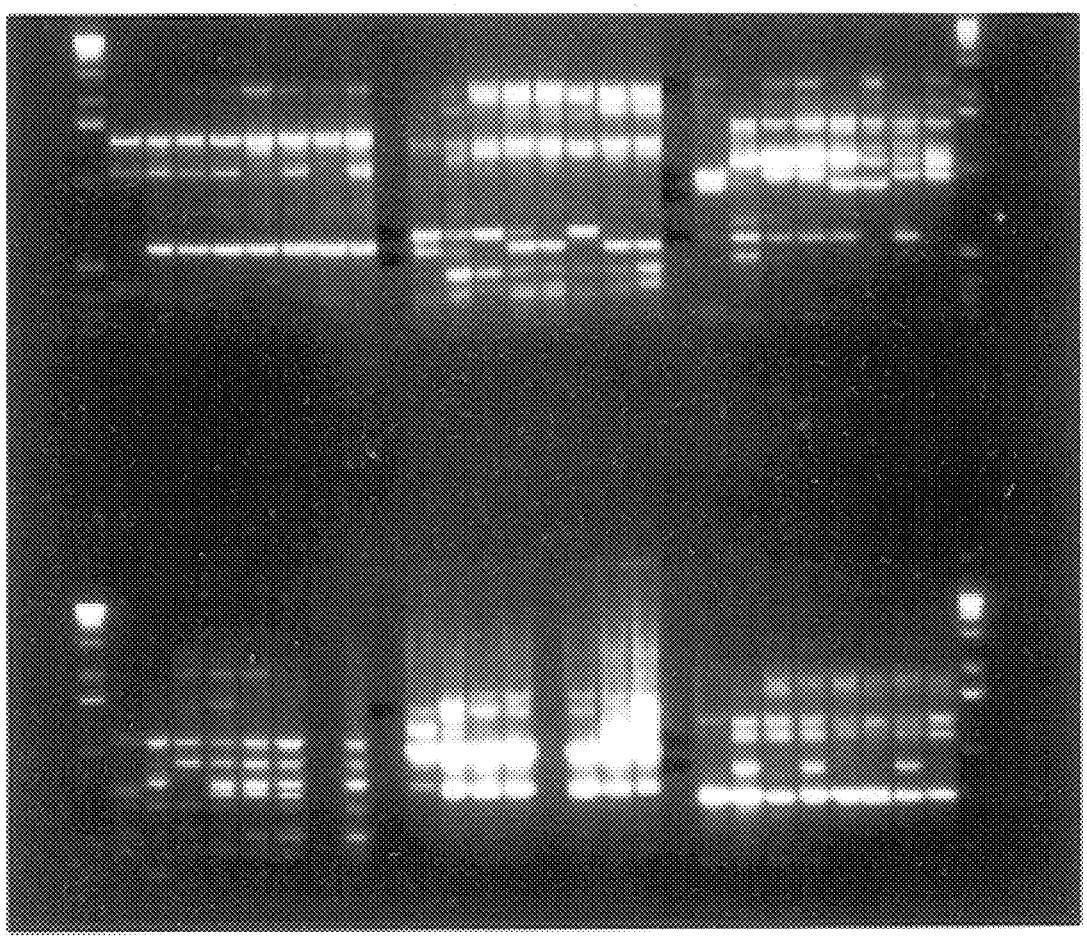
FIG. 1 shows screening of random primers for segregating polymorphisms. Parents (first two lanes of each set) and six F1 individuals were assayed with six primers (results of three primers shown across top of figure, results of three shown across bottom).

The present invention utilizes molecular markers to identify and select genetically superior individuals from within a family of woody perennials such as forest trees. A "family" as used herein refers to a parent plant and a group of its progeny. The progeny may be related to each other as half-sibs (i.e., having one parent in common; half-sib tree progeny commonly result from open pollination of a single maternal tree); as full-sibs (i.e., sharing both maternal and paternal parents); or as selfed progeny (i.e. progeny resulting from crossing pollen and ova from the same plant, known as a self-cross). Selfed progeny are also known in the art as an F2 generation.

Selection of individuals known to carry genes for desirable traits is useful in the propagation of plants with the desirable characteristics. The present invention is directed to a new method for integrating marker analysis and the association of markers with economically important traits, so that genetic marker-assisted selection in woody perennials such as forest trees is possible. Selected individuals are useful for breeding and establishing seed colonies, as well as for clonal propagation. The present method allows the analysis of individual plants within a family for markers of genetic superiority, the selection of plants with markers indicating desirable genotypes, and the propagation of the plants selected.

In forest trees the ability to quickly construct genetic linkage maps in any individual tree opened the way to the heterodox proposal of constructing several maps for individual trees of a breeding population. The paradigm of an index linkage map for a species is an attractive one for comparative mapping applications, however, it does not seem adequate for establishing associations between markers and traits for breeding applications in allogamous populations with wide genetic bases, such as breeding populations of forest trees. Based on this idea, the integration of mapping information into plant breeding programs involves four basic steps: (1) construction of moderate density individual tree maps for elite genotypes, (2) localization of qualitative and quantitative trait loci of interest on these maps by analyzing the performance of multiple members of the family used for map construction. This extended set of progeny would be initially genotyped for a subset of evenly spaced framework markers, followed by a finer search with accessory markers in regions of interest. Alternatively, half-sib families of the mapped individuals could also be used for this purpose; (3) validation of marker-trait associations by replication and prediction experiments, and (4) marker assisted selection of individual plants for propagation or breeding purposes.

The present methods can shorten the time necessary to select superior plants, as the plants need not be grown to full size to ascertain their traits. In forest trees this is especially beneficial due to the time needed to reach maturity. The present method also eliminates the need to select only from full-sib families or multi-generation pedigree (i.e., three generations or more) families of trees in determing genetic superiority. The present method can be used on individual undomesticated trees where limited or no knowledge of the tree's genetic history is available, to perform genetic analysis to determine the existence of genes controlling quantitative or qualitative traits in an oligogenic manner.

The present method is based on a concept which departs from the accepted paradigm of inheritance in woody plants. Traditional, standard quantitative genetics is based on a presumption of polygenic inheritance, i.e., that large numbers of genes act collectively to determine a given trait, with each gene having a small effect. Each trait is thought to be determined by many genes, each gene having only a slight effect on the expression of that trait. Traits believed to be under such genetic control are termed "polygenic traits". The present invention is based on the paradigm of oligogenetic inheritance, in which a small number of genes have a large effect on a given trait; not all genes are equal in effect, rather, some genes have a disproportionate effect on a given trait. Traits believed to be under such genetic control are termed "oligogenic traits".

The present method involves a four-step method: (a) analyzing individual trees' genotypes by the process of genetic mapping, (b) associating genetic markers with specific and desirable traits, (c) selecting plants with these genotypic indications of trait superiority, and (d) propagating the selected tree(s) (e.g., by breeding or by vegetative propagation) to produce progeny which retain the selected trait.

A. Genetic Mapping

The first step is to construct a genomic map of an individual tree using genetic markers. Genetic or recombinant maps are graphical depictions of the relative locations of genes along the chromosomes of a particular genome based on the linkages between specific markers.

A marker indicates an allele whose inheritance is observed during a cross of two parents. An efficient way to construct a genetic map is by using a random amplified polymorphic DNA (RAPD) marker system. See, e.g., Williams et al., *Nucleic Acids Res.*, 18, 6531 (1990); Welsh and McClelland, *Nucleic Acids Res.*, 19, 303 (1990), Williams et al., *Methods in Enzymology: Recombinant DNA*, (1992). Other marker techniques may also be utilized; the methods of the present invention are not limited to the use of RAPD. Any marker system capable of constructing the required genetic maps is suitable for use in the methods of the present invention. Such marker systems include, but are not limited to, RAPD, AFLP, and microsatellite marker systems.

A presently preferred marker system is that of RAPD. RAPD methods are based on polymerase chain reaction (PCR) techniques. DNA fragments are amplified by PCR, based on the presence of short inverted DNA repeats. RAPD markers are typically synthesized by PCR from 10-base oligonucletide primers of arbitrary sequence. Any short sequence of 10 nucleotides is likely to find many complementary sites in any eukaryotic genome. When two sites are nearby and in inverted orientation, PCR can amplify the DNA between the sites; this DNA fragment is identified by its size which is determined by the distance between the short inverted repeats. RAPD methods thus identify genetic polymorphisms that are inherited as dominant Mendelian markers. If one or more of the target sites are absent in a genome, a null phenotype is indicated by the lack of a band.

Construction of a genomic map of a tree with genetic markers is carried out using a family of trees, where the family of trees comprises either full-sib, half-sib, or selfed progeny. Full-sib trees are those having the same female and the same male parent. Half-sibs are those trees having only one parent in common. Selfed progeny result from the union of pollen and egg from the same parent. A special feature of gymnosperms is the nutritive haploid megagametophyte tissue in the seeds, which is a mitotic derivative of a single haploid megaspore which is derived from the same megaspore that gives rise to the maternal gamete. The embryo and the megagametophyte differ only in the paternal contribution to the zygote. Each seed of a tree carries the genetic information from an independent meiotic event in the seed parent. Megagametophytes derived from seeds of a single tree show 1:1 segregation and are equivalent to a test cross. Mapping strategy using only megagametophytes from the seed parent is equivalent to half-sib mapping. The half-sib mapping strategy depends on finding individual trees that are heterozygous for many loci, and on examining the genotypes of the haploid megagametophytes. Extended pedigrees are not needed, and mapping can be done on the seed parent using controlled cross or open pollinated seed. The frequency of genetic polymorphism is typically high for conifer species.

The methods of the present invention can be used to map traits for any sexually mature individual tree belonging to a species exhibiting high genetic variability, i.e., where the level of segregating polymorphisms is high enough that obtaining a genomic map of moderate density is possible, for example, where obtaining approximately 200 or more markers is feasible. The methods assume that the individual parent plant and its progeny are available for testing. Preferably, the level of polymorphism of the species is sufficient to allow genetic maps to be created using a few hundred oligonucleotides for initial screening and a subset of oligonucleotides for mapping. Thus the methods of the present invention do not require that a three-generation family of trees be available. Any individual tree and its progeny may be mapped; both conifers (which contain haploid megagametophyte tissue) and deciduous trees (containing only diploid somatic tissue) can be used in the present methods. Mapping can be done using open pollinated trees or on trees in full sib crosses. The ability to map any sexually mature tree from collected open pollinated seed allows variation, recombination and linkage in individual trees to be studied directly in natural populations.

B. Associating Genetic Markers with Traits

The next step of the method is to associate individual markers with specific traits and validate this association. This determination is accomplished using large sets of full-sib, half-sib, or selfed families. The traits selected for association to markers are preferably economically desirable traits such as growth, disease resistance, wood volume and wood quality (e.g., specific gravity of the wood).

In mapping quantitative trait loci (QTLs) using the methods of the present invention, RAPD markers may be used. In mapping half sib conifer families exact knowledge of the markers contributed by the maternal parent of the embryo or seedling can be obtained from the megagametophyte. The analysis of the maternal contribution to a quantitative trait is carried out by detemining the genotype of the megagametophyte and scoring the dipoloid progeny for quantitative traits. The genes contributed to the half sib progeny by the common male parent are deduced from the progeny genotypes.

The understanding of the genetic control of complex economic traits has been changed by the use of molecular markers to identify genomic regions which have phenotypic effects. These genomic regions are assumed to contain genes controlling quantitative traits or quantitative trait loci (QTLs). QTLs have been found in several field crops, such as maize, tomato, and soybean. Many methods have been proposed for mapping quantitative trait loci (QTL) for field crops. The statistical approaches to QTL analysis include: simple t-test, simple linear regression, multiple linear regression, log-linear functions, mixture distributions, and nonlinear regression. Single marker, two adjacent marker interval mapping, and multiple marker methods have been proposed to locate QTLs on genomic maps.

Single-Marker Model: This is the simplest search for association between markers and quantitative traits. The model assumes that a marker associated with a QTL with two alleles (diploid) and locates a QTL r percent recombination away from the marker. For the backcross configuration (1:1), a t-test can be used for detecting the difference of the trait performances among the two marker genotypes. For the F2 configuration (1:2:1), regression and analysis of variance can be used to detect the association between trait performances among the three marker genotypes which can be coded as 0, 1, and 2 based on number of certain alleles presented in the genotype. For both backcross and F2 configurations, a likelihood approach can be used to detect the association based on a mixture model. The advantage of the single marker model is the simplicity. Commercially available statistical software, such as SAS, can be used to perform the analysis. The limitation is the low power of detecting the association when the linkage map is not dense enough because the recombination between the marker and QTL is confounded with the QTL effect.

Two-Marker Model (interval mapping): The model assumes that two markers are linked with recombination r and a QTL locates between the two markers. The expected frequencies and trait value for each of the genotypes of two markers and the QTL can be formulated as functions of QTL effects and recombination among the two markers and the QTL. To solve this model, likelihood approaches, linear regression, and nonlinear regression can be used. MAPMAKER/QTL developed by MIT and QTLSTAT developed at Oregon State University are commonly used now to perform the analysis. One limitation of the two-marker model is that it is still a single QTL model and does not deal with interactions among QTLs.

Multiple-Marker Model: Analyses involving as many markers as possible have gained attention recently due to the limitations of interval mapping. This model requires a large sample size to achieve reasonable results. At this time interactions among QTLs have not been integrated into the model. There is no available software to perform the data analysis.

Marker Assisted Selection: Marker aided selection (MAS) has been studied theoretically (Lande and Thompson 1990; Paterson et al. 1991). The general conclusions are (1) MAS for traits with high heritability is less valuable than for traits with low heritability, (2) QTLs are harder to detect when the trait has low heritability, (3) MAS is efficient when selection intensity is high and the population size is very large. Several aspects of these arguments, however, may have overstated the limitations of selection. First, the multiple regression method of QTL mapping assumed in the work is not entirely suitable. New methods of genome mapping provide greater resolution. Second, oligogenic models of genetic control are more appropriate to QTL analysis than the polygenic models used in this work. The polygenic concepts of heritability and selection response may not adequately model selection based on QTL effects and QTL genotypes. Finally, an assumption of infinite population size is not consistent with the limitations of breeding populations. An alternative approach to classical quantitative genetics MAS within breeding populations would take into account more realistic models for mapping, for oligogenic control of traits, and for limited populations sizes.

Marker Assisted Parent Selection: GMAPB (Genome Map Assisted Plant Breeding) could help breeders carry out parent selection for breeding population synthesis, for maximizing genetic gain, and for maintaining genetic diversity. Genetic diversity of breeding populations is essential for sustainable genetic improvement. Genetic diversity is important for environmental stress resistance and disease resistance.

C. Selecting Desired Individual Plants

After individual plants are analyzed for allele/marker makeup, trees with markers indicating desirable genetic traits are selected, based on the previous association of individual markers with specific traits.

D. Propagation of Selected Individuals

Propagation of the selected individuals may be carried out either through breeding programs or by asexual (vegetative) propagation. As used herein, vegetative propagation refers to the asexual propagation of the plant, e.g., by taking cuttings from the individual and propagating these. Breeding means using the selected trees as parents (either maternal or paternal) in crosses with other trees or self-crosses. These other trees may or may not be known to contain compatible or complementary markers.

E. Subjects

The method of the present invention may be applied to any tree, including both angiosperms and gymnosperms. Of the gymnosperms, conifers are particularly suitable for use in the present invention. Angiosperms suitable for use in practicing the present method include forest trees belonging to the genus Eucalyptus, Liquidambar (e.g, sweetgum), Liriodendron (e.g., yellow-poplar), Platanus (sycamore), Populus (e.g., cottonwoods, poplars, aspens) and domesticated trees such as those belonging to the genus Prunus (e.g., cherries and plums). Eucalyptus species are economically important in providing wood pulp to industries worldwide. Wood pulp is a wood product created by collecting and fragmenting wood, and pulping the wood fragments to obtain wood pulp.

As used herein, the term "conifer" refers to a member of the order Coniferae in the sub-phylum Gymnospermae in the phylum Spermaphyta. Exemplary conifers which may be used in practicing the present invention are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); spruces such as the black spruce and the white spruce (genus Picea); Douglas fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*), noble fir (*Abies procera*), white fir (*Abies concolor*), balsam fir (*Abies balsamea*); and the cedars which include Western red cedar (*Thuja plicata*), incense cedar (*Libocedrus decurrens*), Port Oxford cedar (*Chamaecyparis lawsoniona*), and Alaska yellow-cedar (*Chamaecyparis nootkatensis*); and Western larch (*Laryx occidentalis*). Preferred for practicing the present invention are the pines (genus Pinus) and the most preferred for practicing the present invention is the loblolly pine (*Pinus taeda*).

F. Traits

The method of the present invention may be used to select individual trees carrying genes for desirable traits. Such desirable traits may be quantitative or qualitative traits. As used herein, qualitative trait refers to a trait which is either present or absent, such as flower color or presence of a particular enzyme (i.e., the phenotype is either + or − for the trait). A qualitative trait may be under oligogenic or polygenic control; if under polygenic control the trait is present or absent based on a threshold concept. Complex qualitative traits exist. The mendelian inheritance of these traits is not readily apparent. The discussions herein directed to QTLs (quantitative trait loci) are equally applicable to the analysis of complex qualitative traits.

Quantitative traits are those which are present in every plant, such as height or rate of growth, but which exhibit a range of values. Quantitative traits in woody perennials such as forest trees include, but are not limited to, disease resistance, insect resistance, wood volume, wood quality, height and growth. As used herein, "growth" may refer to the overall rate of increase in mass of an individual tree, or to the rate of increase of a single measurable dimension such as height or diameter. As used herein, "disease resistance" refers to both the ability of an individual tree to avoid infection and damage by pathogens such as viruses (as compared to wild type trees of the same species), and the ability of a stand of clonal trees to resist damage overall due to a pathogen than a stand of wild type counterparts. As used herein, "insect resistance" refers to both the ability of an individual tree to avoid infestation and damage by insects (as compared to wild type trees of the same species), and the ability of a stand of clonal trees to resist insect damage overall than a stand of wild type counterparts. As used herein, "wood volume" refers to the total mass of wood produced by an individual tree. Wood specific gravity is accepted in the art as a measure of wood quality, and reflects the ratio of solids to voids in wood.

As used herein, LOD means Log of the Odds, a statistical measure of significance known in the art; significant difference refers to a departure from expectation unlikely to have resulted by chance, and quantifiable by a probability statement or other measure of significance, such as LOD. As used herein, linkage refers to a statistically significant correlation of the segregation of two genes (for example, a P<0.001 or a LOD>3 would be statistically significant, indicating linkage). As used herein, segregating in an essentially Mendelian manner means segregation in a ratio similar to expected Mendelian ratios (e.g., 1:1, 3:1, 1:2:1, etc.).

As used herein, the term "pseudo-testcross" refers to a strategy using a cross between heterozygous parents. In a cross between heterozygous parents, many single-dose polymorphic markers will be heterozygous in one parent, null in the other and therefore segregate 1:1 in their progeny as a testcross. The name "pseudo-testcross" is used because the testcross mating configuration is not known a priori as in a conventional testcross where the tester is homozygous recessive for the locus of interest. Rather the configuration is inferred a posteriori after analyzing the parental origin and genetic segregation of the marker in the progeny of a cross between highly heterogenous parents with no prior genetic information. When this inference is done for both parents involved in the cross, the term "two-way pseudo-testcross" is more appropriately used.

As used herein, "woody perennial plant" encompasses perennials such as trees, dwarf trees and shrubs. As used herein, hybrid refers to plants resulting from interspecific crosses; sexually mature plant refers to a plant capable of reproducing. As used herein, a plant termed "useful for breeding" refers to plants which carry genetic markers indicating the presence of genes coding for desirable traits.

The methods of the present invention can involve vegetative propagation. Any method of vegetative propagation known in the art to be successful with the particular plant species being worked with is suitable for use in the methods of the present invention. Such methods include but are not limited to grafting, somatic embryogenesis (a tissue culture process which results in production of embryos from cultured cells), rooting of cuttings, auxiliary shoot formation or adventitious bud formation in tissue culture.

Nucleotide sequences disclosed herein are presented in single strand, in the 5' to 3' direction, from left to right, where A=adenine, C=cytosine, T=thymine, G=Guanine.

The following examples are provided to illustrate the present invention, and should not be construed as limiting thereof. In these examples, RAPD means Random Amplified Polymorphic DNA, $\mu$l means microliter, $\mu$M means micro molar, mM means milliMolar, ng means nanogram, ° C. means degrees centigrade, cM means centimorgan (a measure of the recombinational distance between genes on a chromosome), PCR means polymerase chain reaction, g means gravity, and min means minutes.

EXAMPLE 1

Materials & Methods for RAPD Analysis

RAPD Analysis Technique: Random ten base primers were obtained from Operon Technologies (Alameda, Calif.). Amplification reactions were performed in bovine serum albumin (BSA) containing 1.3 $\mu$l of 10× buffer (100 mM Tris-HCl pH=8.8, 500 mM KCl, 15 mM MgCl2, 1% Triton-X 100), 100 $\mu$M each of dATP, dCTP, dGTP, dTTP, 0.2 mM primer, 5 to 10 ng of genomic DNA and 0.7 units of Taq DNA polymerase. If BSA was not available the reaction mixture was brought up to volume using sterile water, however, the use of BSA was preferred. Amplification was performed in 96-well plates using a MJ Research PT-100 thermal controller programmed for 41 cycles of 1 minute at 92° C., 1 minute at 35° C., 2 minutes at 72° C. Amplification products were analyzed by horizontal gel electrophoresis in 1.5 percent agarose TBE gels and detected by ethidium bromide staining. Gels were run at RT, 100 V, for 4.5 hours or until the dye had touched the very bottom of the gel. Molecular weight markers were used as standards. Gels were photographed under ultraviolet light with POLAROID™ film 667. RAPD fragments visualized as bands on a gel were scored for presence or absence across the individuals or bulks analyzed. Fragment sizes were calculated using the software SEQAID II (Rhoads & Roufa, SEQAID 3.80 (1990)).

EXAMPLE 2

Optimization of the RAPD Analysis for Eucalyptus

Among several DNA isolation procedures tested, the CTAB (hexadecyltrimethylammonium bromide) DNA isolation procedure proved the most efficient at obtaining genomic DNA that would consistently amplify by PCR. See Doyle and Doyle, *BRL Focus*, 12, 13–15 (1990); Bernatzky and Tanksley, *Theor. Appl. Genet.*, 72, 314 (1986). Starting tissue was an important variable. Young, tender tissue from expanding leaflets proved to be the best starting material in order to obtain high yields of clean DNA. To obtain such tissue, plants were either grown in the greenhouses under intensive care or maintained in vitro in a culture flask. For adult leaf tissue, the DNA procedure was essentially the same. However, oxidized phenolics and polysaccharides frequently co-precipitated with the DNA and tended to inhibit the PCR reaction. To overcome this problem the best strategy was to not clean the DNA but rather to either establish an "in vitro" stock of the genotype of interest, or to induce epicormic shoots from branches under mist irrigation to obtain cleaner starting tissue.

The optimal RAPD reaction conditions for Eucalyptus were established after testing variable concentrations of template genomic DNA, magnesium and Taq polymerase (data not shown). Concentrations between 5 and 10 ng of genomic DNA were optimal. Magnesium concentration between 1.5 and 2.0 mM could be used, however 1.5 mM was the concentration at which the RAPD reaction showed less primer dependency. Taq polymerase concentrations down to 0.5 units (in 13 $\mu$l) could be used, however, it was found that with 0.7 units consistency was higher. Over 200 different random ten-base oligonucleotides were tested. Primer concentration of 0.2 mM was optimal. Variable success was obtained in the assay depending on the primer used. In general, about 50 to 70 percent of the random primers screened yielded informative DNA polymorphisms.

EXAMPLE 3

Genetic Inheritance, Segregation and Linkage of RAPD Markers

Screening of Random Primers for Segregating Polymorphisms: To assess the inheritance and segregation of RAPD markers, forty random primers were used to carry out a RAPD analysis on two parent plants and a sample of 6 F1 individuals of a controlled cross. This screening step looked for RAPD fragments that were transmitted from parents to F1 and that segregated for presence and absence among the progenies. FIG. 1 shows the result of this screening step with six different primers (this being a general example, primer sequences are not shown). The first two lanes of each set are parent plants; lanes 3–8 are the six individual F1 progeny. Several RAPD fragments were found to be polymorphic between the two parents and to segregate in the progenies. From a total of 40 primers screened, 28 were found to yield at least one polymorphic segregating RAPD marker. For a total of 58 markers, segregation was analyzed on 30 F1 individuals.

Figure 2:
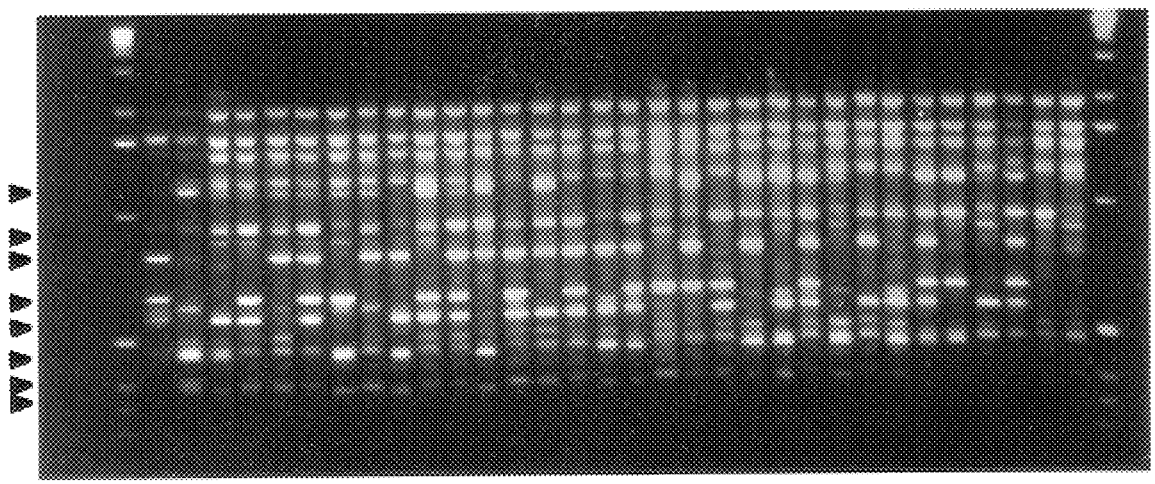
FIG. 2 shows the genetic inheritance and segregation of RAPD markers in Eucalyptus. The first and last lanes are size markers. The second and third lanes on the left of the figure are the two parental profiles; the remaining 30 lanes represent 30 F1 individuals. The eight segregating markers obtained with this primer are indicated by arrows.
Figure 3A:
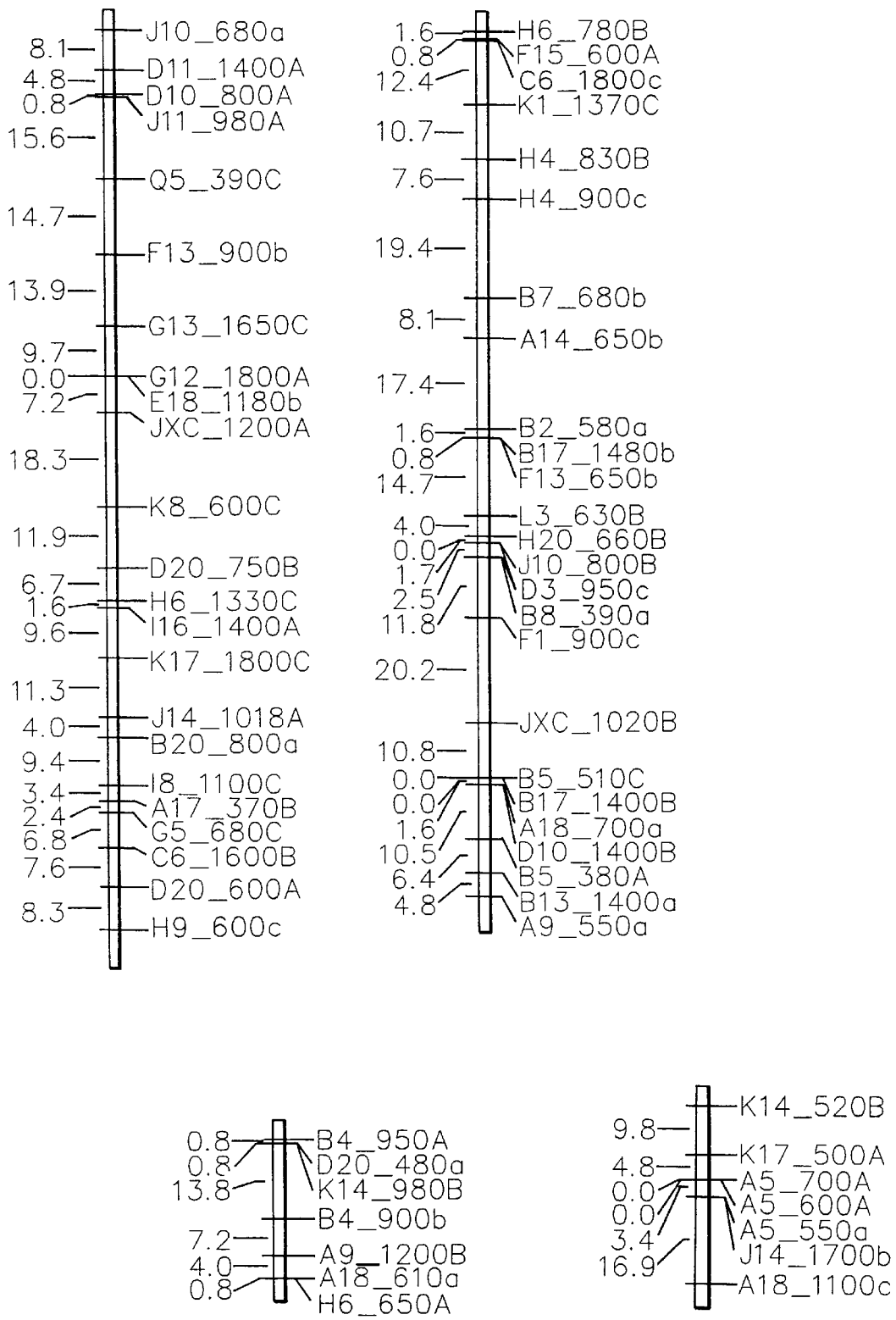
FIGS. 3A–3D together comprise a linkage map of the genome of Pinus taeda (loblolly pine) derived from clone 10-5 from the NCSU: Industry Tree Improvement Cooperative Breeding Program. Seventeen linkage groups are indicated. The numbers to the left of the linkage groups represent the location of markers along the linkage group in cM. Designations to the right of the linkage groups are the names of primers as designated by Operon Technologies, Inc. (Alameda, Calif.) corresponding to a particular ten-base sequence, followed by an underscore, then a number indicating the fragment size in base pairs. The estimated genomic coverage is 99%.
Figure 3B:
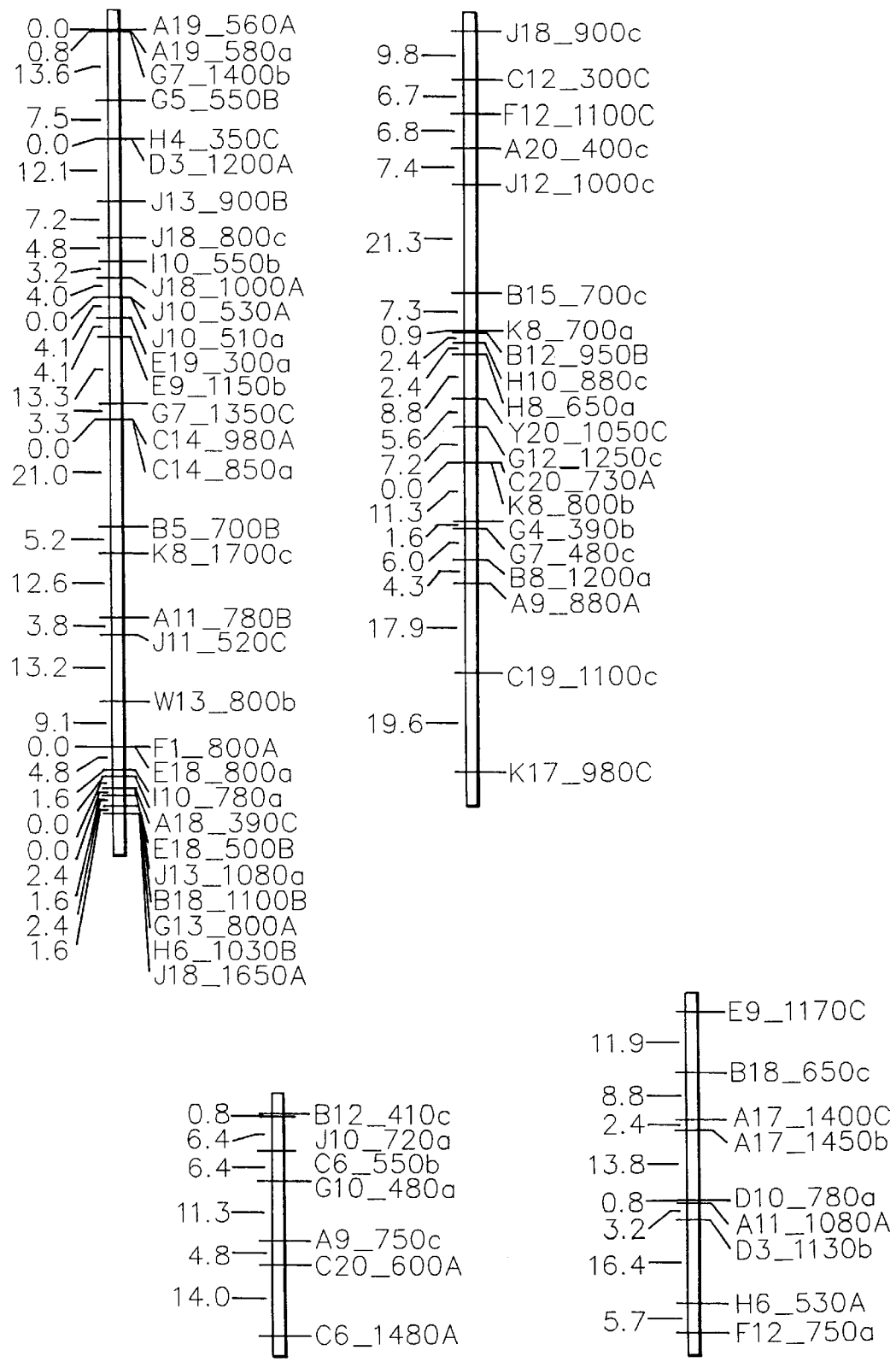
Figure 3C:
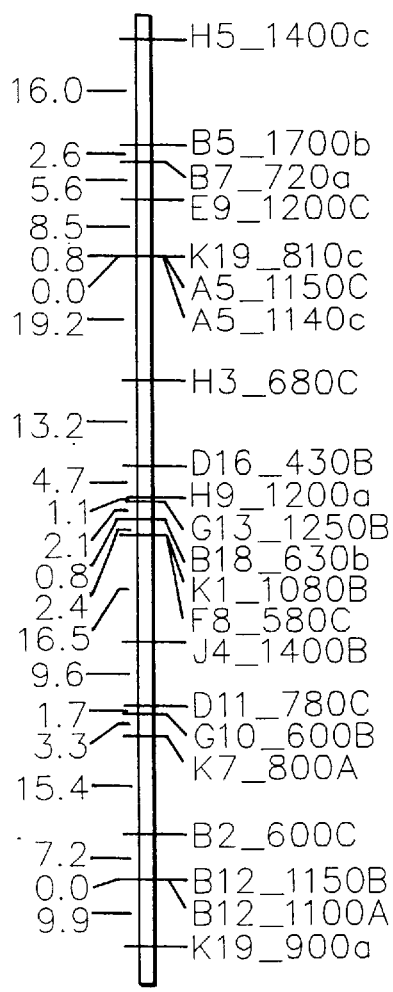
Figure 3C:
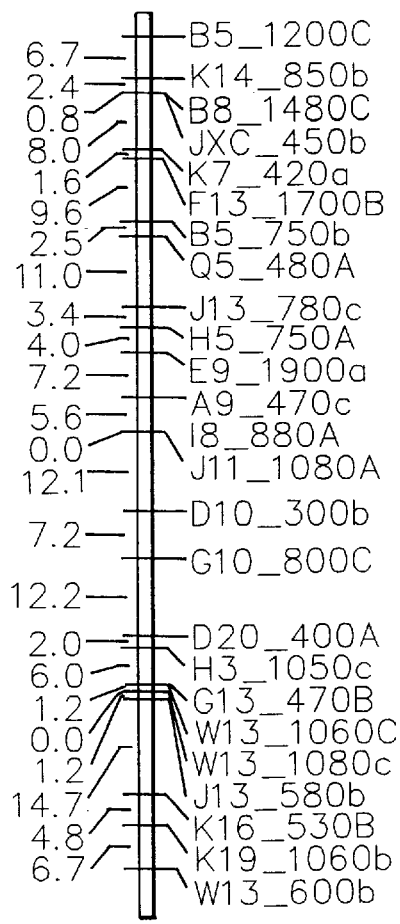
Figure 3C:
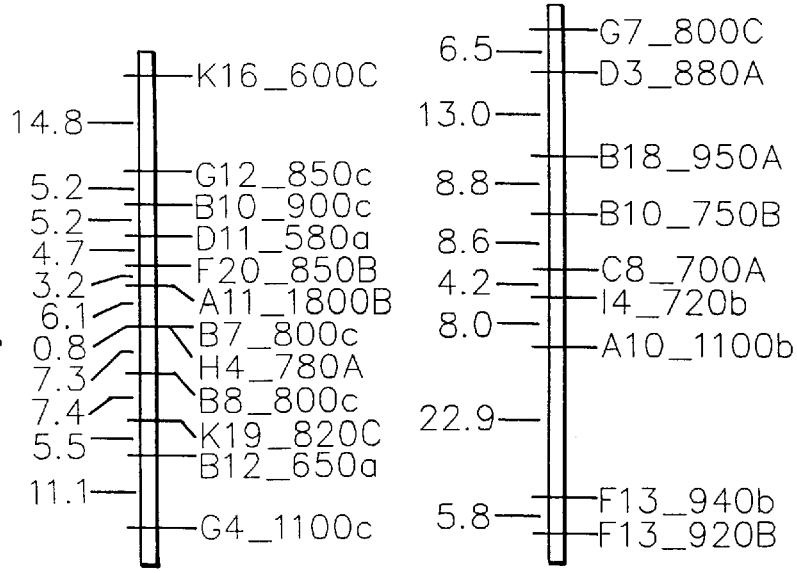
Figure 3D:
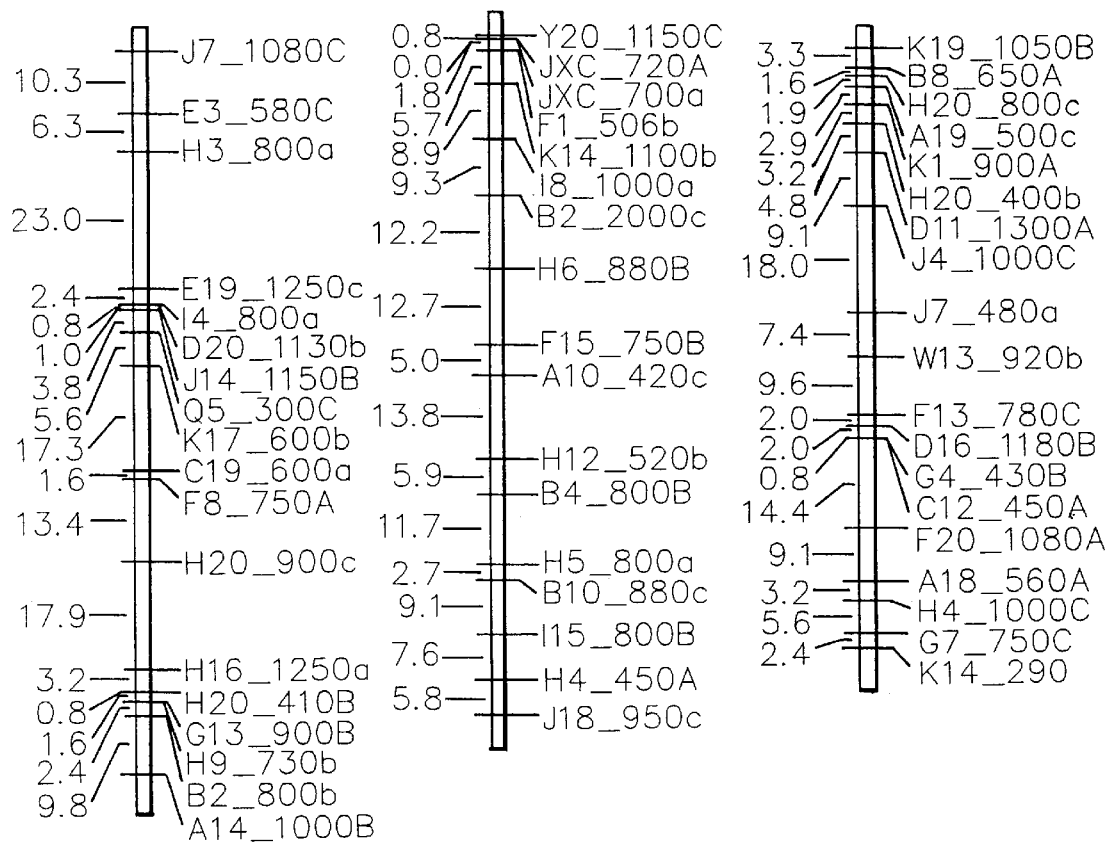
Figure 3D:
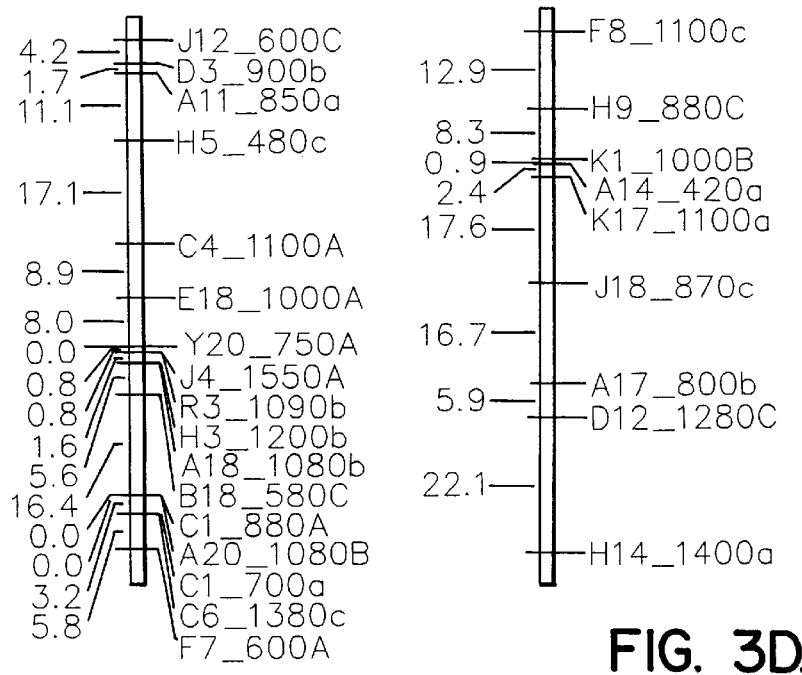

Genetic Inheritance and Segregation of RAPD Markers in Eucalyptus: Two parental plants (*E. grandis* clone 44 and *E. urophylla* clone 28) and 30 F1 individuals of this cross, were analyzed. FIG. 2 shows the genetic inheritance and segregation of several RAPD markers amplified with a single primer (first and last lanes=size markers; lane 2 parent *E. grandis* clone 44; lane 3 parent *E. urophylla* clone 28; lanes 4–33 are 30 F1 individuals). Segregating markers are indicated by arrows; a total of eight markers were obtained with this primer. Results of the Chi-square analysis of goodness-of-fit are given in TABLE 1. The observed 1:1 ratio follows the expected Mendelian segregation of alleles in a test cross, where one of the parents is heterozygous (genotype +/−) and the other parent is homozygous null (−/−) for the locus under consideration. This configuration is here referred to as pseudo-testcross since the marker configuration of the parents is inferred from the progenies a posteriori, i.e. without prior planning as in a true testcross. For only four RAPD loci a significant Chi-square statistic was obtained, which indicates distortion from a 1:1 ratio. To minimize type 1 errors, a cut-off Chi-square of 15.00 was used as criterion to determine linkage between pairs of markers. The observed number of linkages agrees with the expectation based on the prior probability of linkage with the available number of markers as previously described (Grattapaglia et al., *Plant Genome I*, San Diego, Calif., Poster #47 (1992); Grattapaglia et al., *Proceedings of the Symposium on Applications of RAPD Technology to Plant Breeding*, CSSA/ASHS/AGA, 37–40 (1992)). With such stringency, only close linkages (theta<0.15) were estimated. In order to obtain more precise estimates of theta for linkage map construction, a larger number of progeny must be genotyped.

TABLE 1

| LOCUS 1 | LOCUS 2 | (+/+) | (+/−) | (−/+) | (−/−) | THETA | CHS.LOC1 | CHS.LOC2 | **CHS.LINK |
|---|---|---|---|---|---|---|---|---|---|
| G6_1140 | H3_1323 | 16 | 2 | 1 | 9 | 0.11 | 2.29 | 1.29 | 17.29 |
| A10_635 | G12_1231 | 12 | 0 | 1 | 16 | 0.03 | 0.66 | 0.31 | 25.14 |
| A10_635 | G5_1898 | 11 | 1 | 3 | 15 | 0.13 | 1.20 | 0.13 | 16.13 |
| A10_562 | G12_1231 | 1 | 16 | 12 | 0 | 0.03 | 0.86 | 0.31 | 25.14 |
| A10_562 | G5_1896 | 3 | 15 | 11 | 1 | 0.13 | 1.20 | 0.13 | 16.13 |
| A11_2374 | B6_515 | 14 | 1 | 0 | 15 | 0.03 | 0.00 | 0.13 | 26.13 |
| A11_1439 | A20_2127 | 18 | 0 | 2 | 9 | 0.07 | 1.69 | 4.17* | 21.55 |
| A11_1439 | A19_2448 | 13 | 1 | 0 | 10 | 0.04 | 0.67 | 0.17 | 20.17 |
| A11_635 | G12_1459 | 10 | 1 | 1 | 17 | 0.07 | 1.69 | 1.69 | 21.55 |
| A11_635 | A7_865 | 1 | 10 | 16 | 1 | 0.07 | 1.29 | 1.29 | 20.57 |
| A11_635 | A2_1744 | 2 | 6 | 17 | 1 | 0.12 | 3.85* | 5.54* | 15.38 |
| D2_1095 | G12_1459 | 9 | 2 | 0 | 16 | 0.07 | 0.93 | 3.00 | 19.59 |
| D2_1095 | A7_865 | 2 | 9 | 15 | 0 | 0.08 | 0.62 | 2.46 | 18.62 |
| D2_1095 | A19_398 | 0 | 9 | 13 | 1 | 0.04 | 1.09 | 0.39 | 19.17 |
| D2_848 | G2_1444 | 0 | 13 | 13 | 1 | 0.04 | 0.04 | 0.04 | 23.15 |
| D2_548 | G5_304 | 12 | 1 | 0 | 15 | 0.04 | 0.14 | 0.57 | 24.14 |
| D3_508 | G12_1459 | 9 | 1 | 1 | 17 | 0.07 | 2.29 | 2.29 | 20.57 |
| D3_508 | A7_865 | 1 | 9 | 16 | 1 | 0.07 | 1.81 | 1.81 | 19.59 |
| D3_508 | A2_1744 | 1 | 6 | 17 | 1 | 0.08 | 4.84* | 4.84* | 17.64 |
| B6_810 | A20_2127 | 18 | 0 | 2 | 9 | 0.07 | 1.69 | 4.17* | 21.55 |
| B6_810 | G2_584 | 2 | 16 | 11 | 1 | 0.10 | 1.20 | 0.53 | 19.20 |
| B6_810 | G2_519 | 16 | 2 | 1 | 11 | 0.10 | 1.20 | 0.53 | 19.20 |
| B6_810 | A19_2448 | 13 | 1 | 0 | 10 | 0.04 | 0.67 | 0.17 | 20.17 |
| B6_780 | A20_1068 | 17 | 1 | 0 | 11 | 0.03 | 1.69 | 0.86 | 25.14 |
| B6_780 | A2_1691 | 17 | 0 | 2 | 7 | 0.08 | 2.46 | 5.54* | 18.62 |
| B7_1732 | A18_509 | 13 | 1 | 1 | 11 | 0.08 | 0.15 | 0.15 | 18.62 |
| B7_1549 | A18_509 | 1 | 11 | 13 | 1 | 0.08 | 0.15 | 0.15 | 18.62 |
| G12_1459 | A19_398 | 0 | 9 | 12 | 2 | 0.09 | 1.09 | 0.04 | 15.70 |
| G12_1231 | GS_1898 | 12 | 1 | 1 | 15 | 0.07 | 0.31 | 0.31 | 21.55 |
| A7_865 | a19_398 | 12 | 2 | 0 | 9 | 0.09 | 1.09 | 0.04 | 15.70 |
| A20_1068 | G5_1898 | 3 | 14 | 11 | 1 | 0.14 | 0.86 | 0.03 | 15.21 |
| G2_1444 | G5_304 | 0 | 14 | 13 | 2 | 0.07 | 0.03 | 0.31 | 21.55 |

Genetic segregation and linkage of RAPD marker loci. Columns list from left to right: markers i.d. (primer number_fragment size in bp) for pairs of linked loci; counts of the 4 haplotypic classes; recombination fraction (theta); Chi-square statistics of goodness-of-fit test to 1:1 segregation for each locus (*indicates distorted locus); Chi-square statistics for linkage at p < .001.

EXAMPLE 4

OTL Analysis in a Eucalyptus Family

A large (>1,000,000 trees) half-sib family of Eucalyptus trees has been analyzed using the present method. A known female eucalyptus tree was crossed with many male plants from different species of Eucalyptus. After the cross, seeds were collected from the female parent and planted over thousands of hectares, resulting in over one million full-grown trees within the same half-sib family. In a sample of over 400 of these progeny, traits such as wood quality and wood volume were examined and 87 significant markers were identified and associated with the traits. (Data not shown.) From this data a genomic map was constructed.

An analysis of the map revealed several quantitative trait loci (QTLs). It was determined that two QTLs which were linked to wood volume traits accounted for 25% of the variability in the phenotype. In the trait of wood specific gravity, four QTLs accounted for 35% of the variance in the family.

From this analysis it was determined that the change from one allele to another in a particular QTL can "move" the phenotype of a particular population 0.66 of a standard deviation in the trait of wood specific gravity. To compare, in the wild, it may take many generations to change a population's phenotype one standard deviation. These data suggest that in experimental situations, a population's phenotype could be altered by 0.5 standard deviations, and changed by 1.0 standard deviations in just two generations, using controlled breeding with the selection of the parent trees based on the present method.

EXAMPLE 5

Resistance to Fusiform Rust Disease in Loblolly Pine

The genetic basis for resistance to the causal agent of fusiform rust disease, *Cronartium quercuum* f.sp. *fusiforme* (Cqf), in loblolly pine (*Pinus taeda*) was studied using RAPD genetic markers and under the hypothesis that resistance to Cqf is under oligogenic control. Previous to this experiment, there was no conclusive evidence that the genetic basis for resistance was oligogenic.

A putative heterozygous (Rr) mother tree (clone 10-5) (N.C.S.U.: Industry Tree Improvement Cooperative Breeding Program) along with two open pollinated daughters (half-sib clones Clone 152-231 and Clone 152-257) were crossed to a highly susceptible pollen parent (rr). Progeny from the resulting full-sib families were challenged with inoculum from known single aeciospore lines and scored for several greenhouse resistance symptoms types. As a susceptible pollen parent was used, only the maternal contribution to the progeny was examined by constructing RAPD maps using megagametophyte tissue. The susceptible pollen parent should not contribute alleles conferring resistance.

Seedlings were tested in the greenhouse by inoculation at six to seven weeks after germination, and scoring the disease for gall formation at three to seven months after inoculation (see Knighten et al., Resistance Screening Center Procedures Manual: A step-by-step guide used in operational screening of southern pines for resistance to fusiform rust. Forest Pest Management Report 83-1-18 (revised 1988). USDA Forest Service, Asheville, N.C.; de Souza et al, *Forest Sci.*, 37, 836 (1991)).

Resistance to particular strains of Cqf was studied: resistance of Clone 10-5 to Aeciospore line 20-21; resistance of Clone 10-5 to Aeciospore line 2–36; resistance of Clone 152-231 to Aeciospore line 2-36; and resistance of Clone 152-257 to Aeciospore line 20-21. As heterogenicity in virulence may exist among aeciospores isolated from within a single gall, basiospore inoculum derived from single aeciospores was used to limit genetic heterogeneity.

RAPD analysis was used. DNA was prepared from megagametophytes according to Doyle and Doyle, BRL Focus, 12, 13 (1990) with minor modifications. One $\mu$g of DNA was routinely obtained from a megagametophyte 5 days after germination. RAPD reactions were carried out in 13 $\mu$l of PCR buffer (Cetus) using 3 ng of megagametophyte DNA, 0.9 units of Taq polymerase, 0.8 ng of 10 base oligomers as primer in a standard reaction mix containing dNTPs at 0.2 mM. Oligonucleotides were purchased from Operon (Alameda, Calif.) or from UBC Biotechnology or made locally. The thermocycling program was 94° C. for 1 min; 37° C. for 1 min; 72° C. for 2 min; for 42 cycles. The reaction buffer contained 10 mM Tris-HCl pH 8.3, 50 mM KCl, 1.5 mM $MgCl_2$ and 0.01% gelatin.

Scores for the presence or absence of RAPD markers for all megagametophytes were analyzed for cosegregation using a program to calculate Chi square values. Those pairs of loci that cosegregated were assigned to linkage groups. MAPMAKER was used to order loci on genetic maps and to confirm linkage associations.

The three families resulting from the cross of the susceptible pollen parent with clone 10-5 and half-sib clones 152-231 and 152-257 have been genotyped. For the initial maps we selected two inoculum by family combinations that approached 1:1 segregation for the presence/absence of galls. Maps using 418 markers in clone 10-5 were prepared (FIG. 3). Sample sizes were expanded using extra progeny genotyped for framework markers. Putative associations between markers and resistance ($\alpha \geq 0.01$) have been found in both families.

Figure 4:
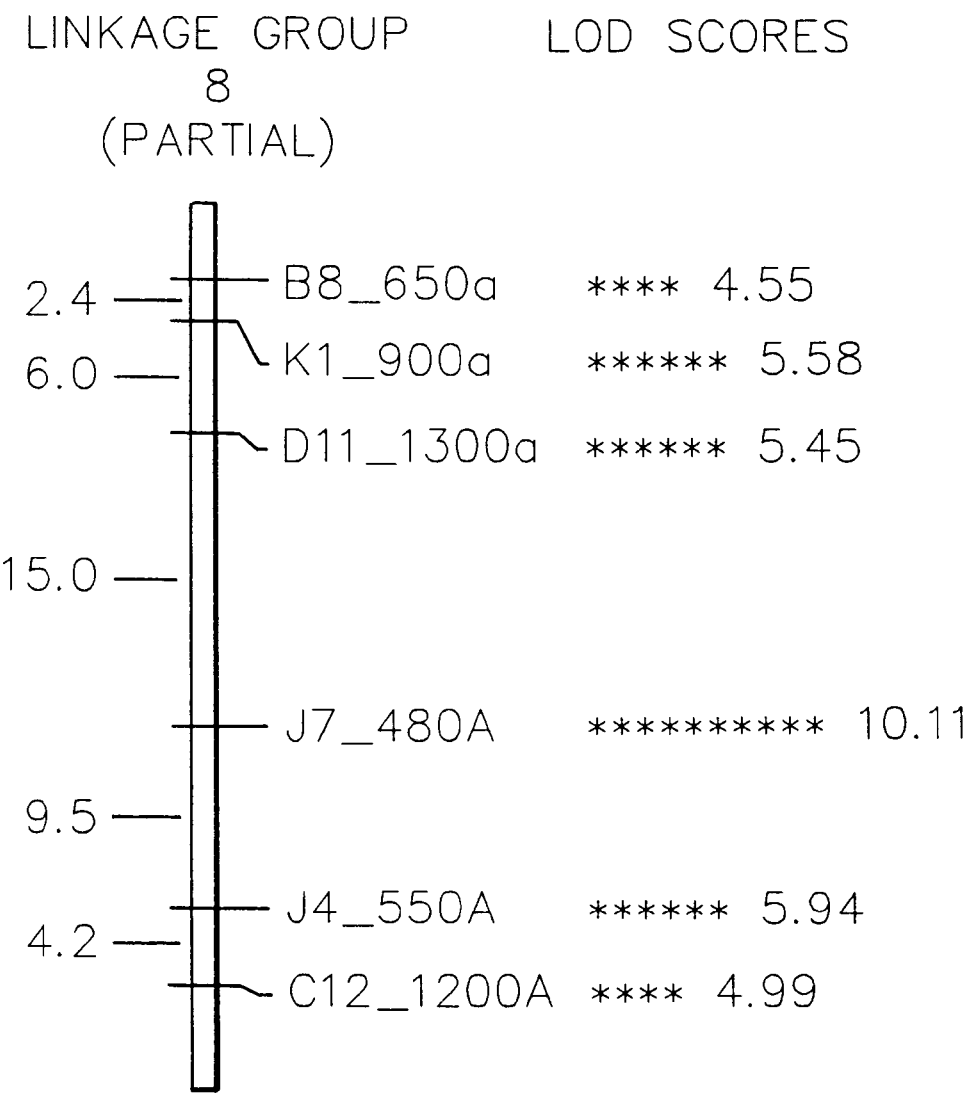
FIG. 4 shows a group of markers putatively linked to resistance to Fusiform Rust Disease in the clone 10-5 (loblolly pine). The markers are all located on the same linkage group (group 8). Numbers to the left of the linkage group indicate location of the marker in cM; designations to the right of the group are the names of the primers as indicated above in description of FIG. 3. LOD scores for each marker are also indicated.
Figure 5A:
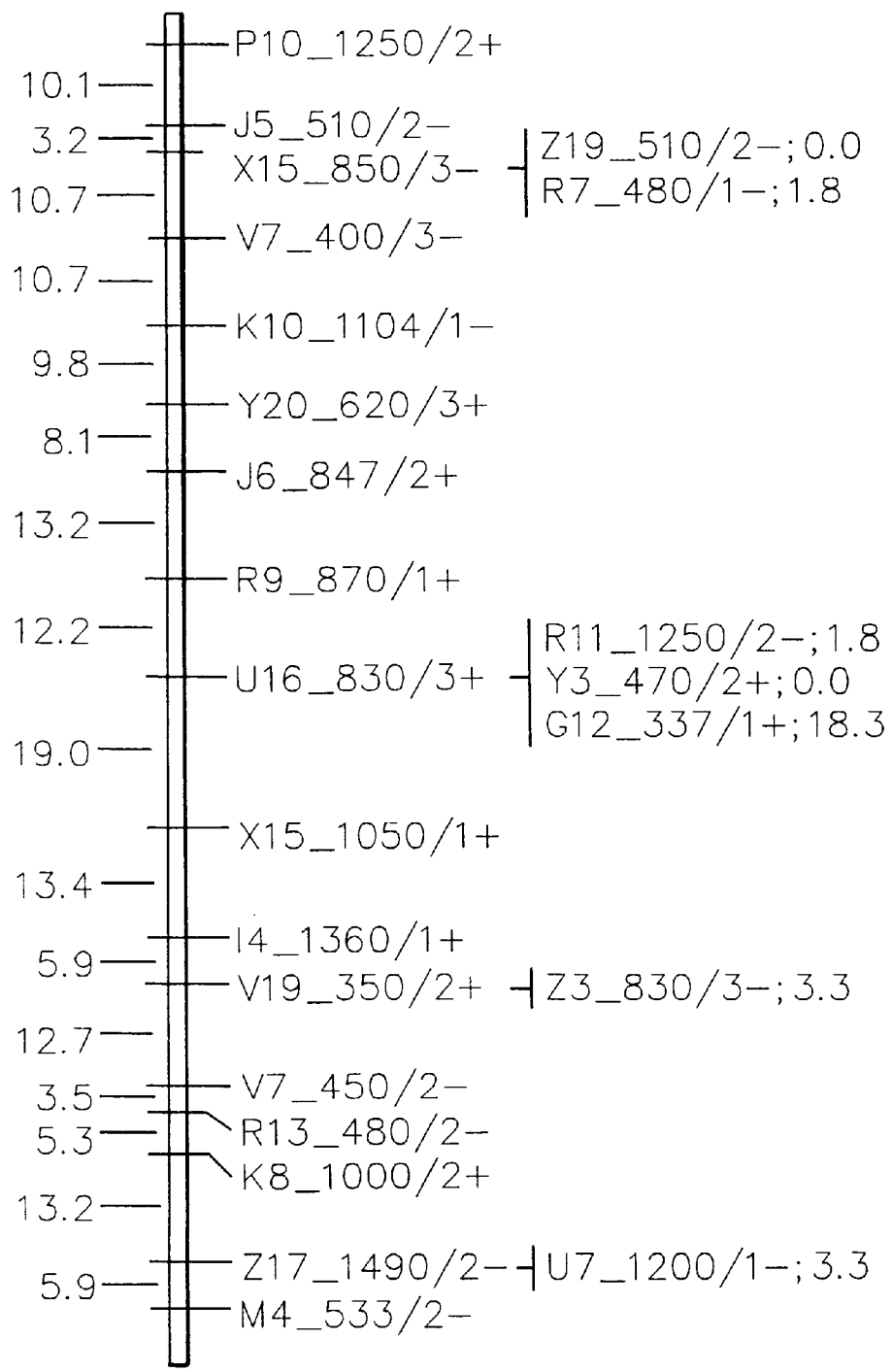
FIGS. 5A–5J together comprise the genetic linkage map of Eucalyptus grandis clone 44. Linkage relationships of 240 RAPD markers in 14 linkage groups were estabished at a threshold LOD score 5.0 and maximum γ=0.25. A framework map of 142 loci or loci clusters (indicated in bold letters along the linkage groups) that could be ordered with a likelihood support ≧1000:1 was assembled covering 95.8% of the estimated genome size. RAPD marker loci that could not be ordered with equal confidence were designated as accessory markers and are listed on the right of the linkage groups along with the approximate cM distance to the closest framework locus. RAPD marker loci are identified by Operon Technologies primer code (see above), fragment size in base pairs, fragment amplification density and linkage phase (+ or −). A RAPD marker locus showing a significant distortion from 1:1 segregation ratio is indicated by an asterisk.
Figure 5B:
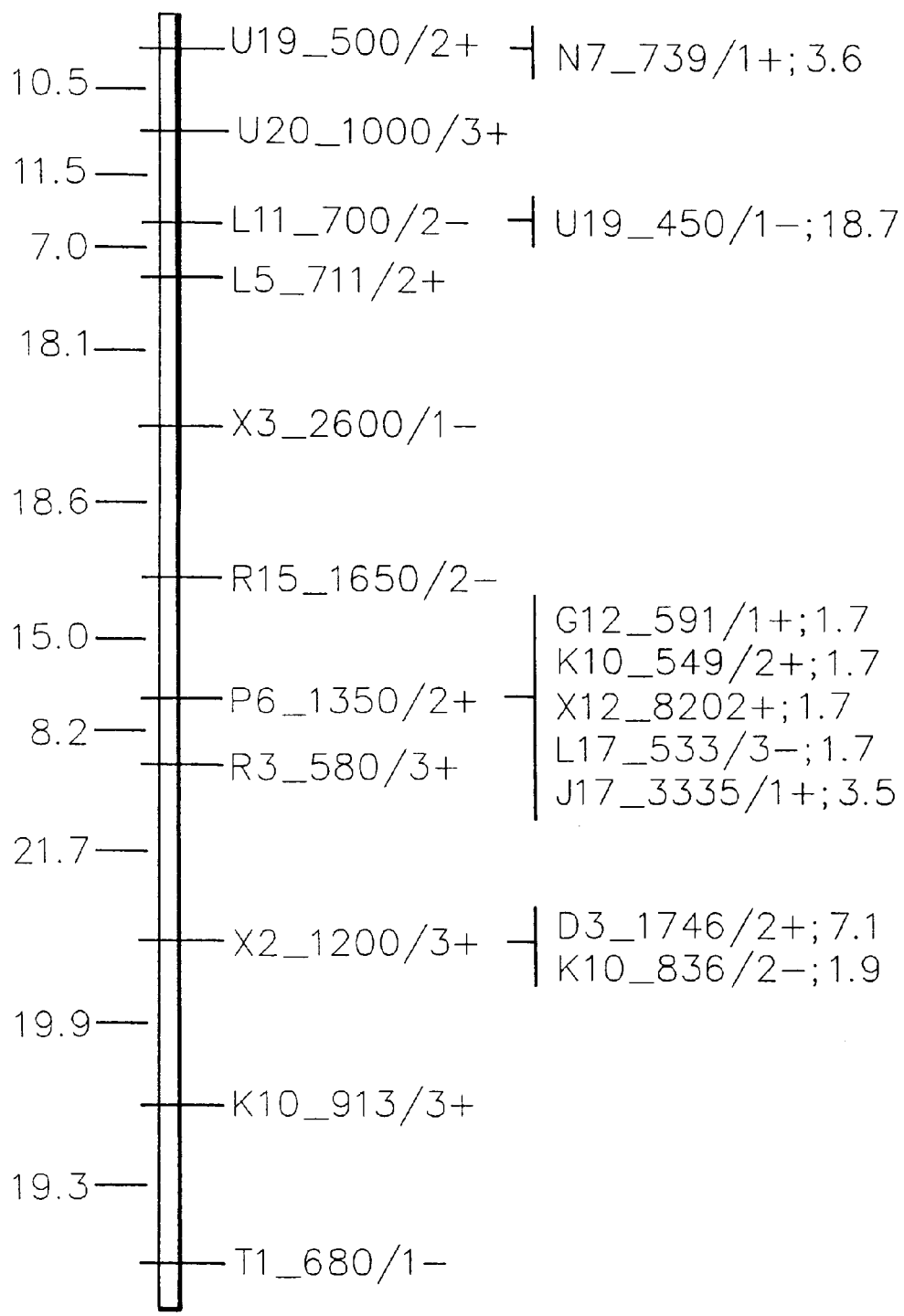
Figure 5C:
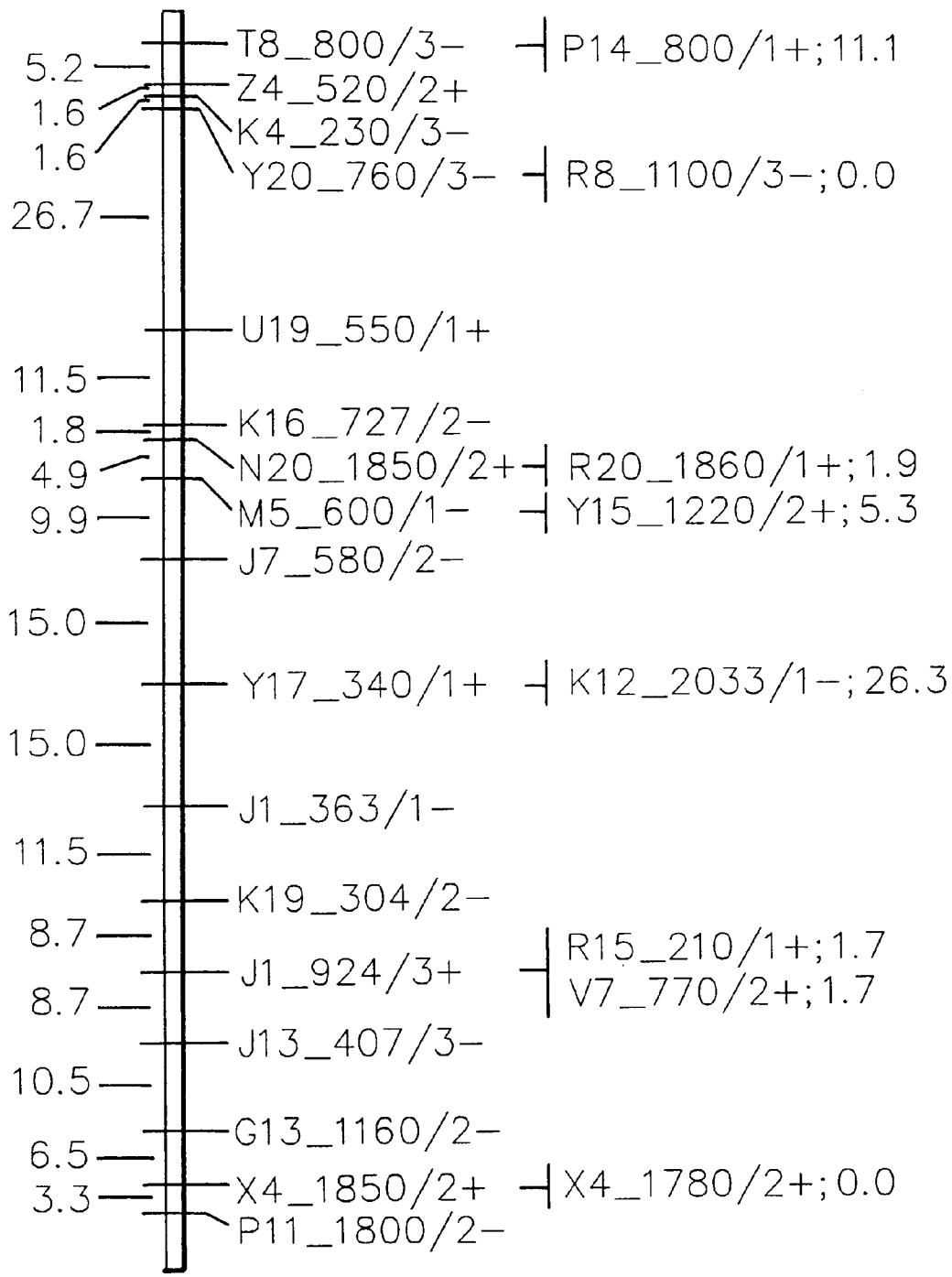
Figure 5D:
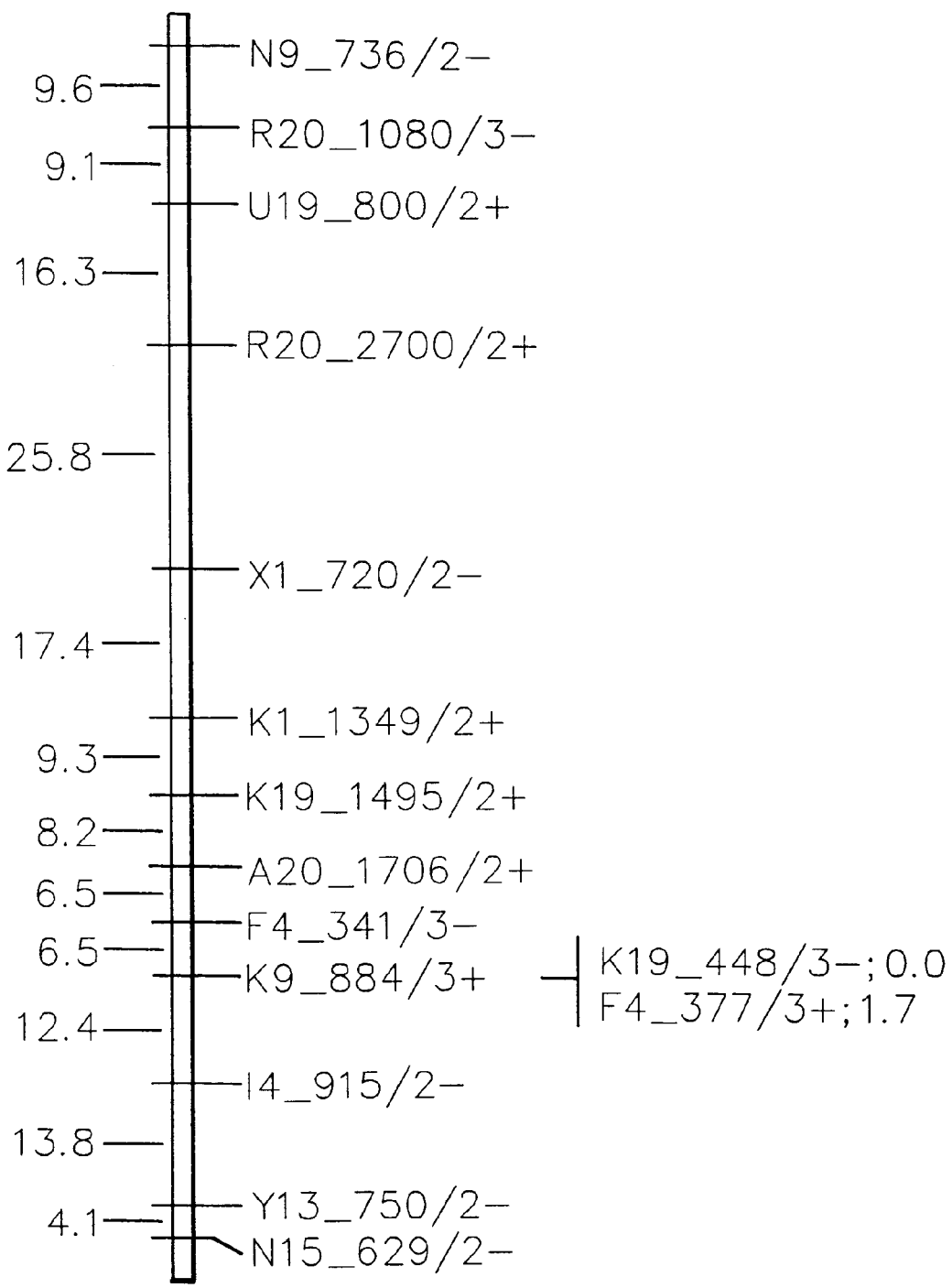
Figure 5E:
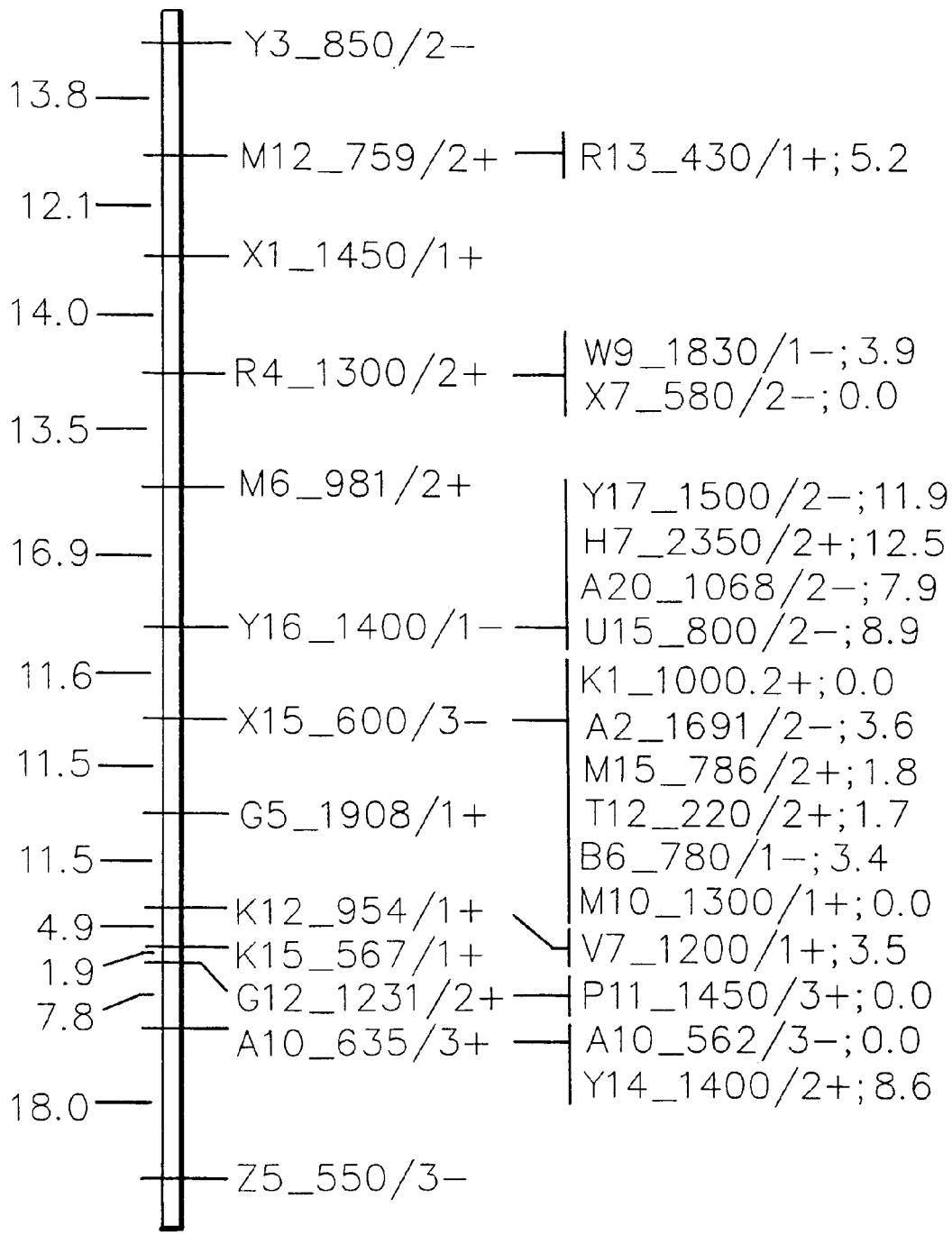
Figure 5F:
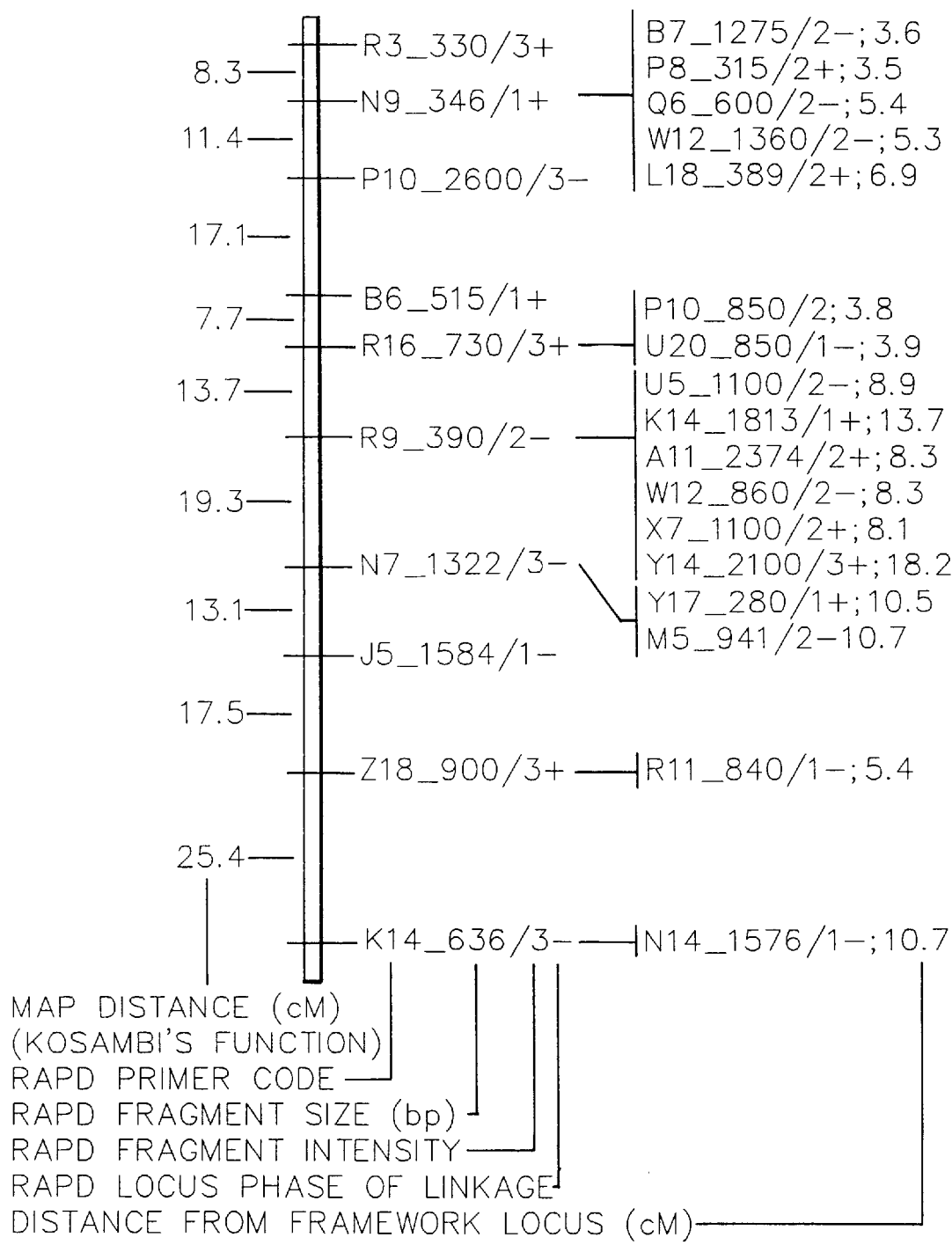
Figure 5G:
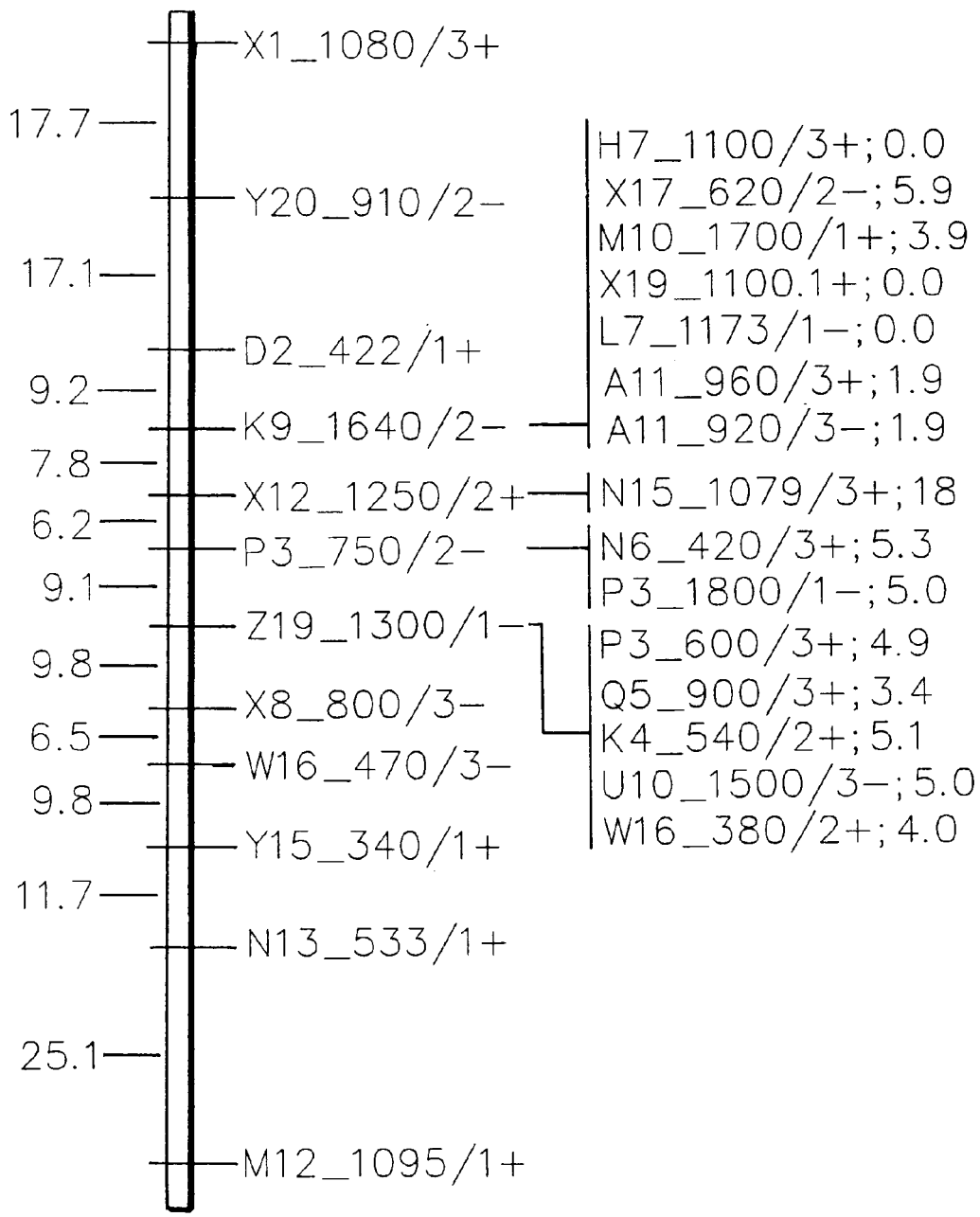
Figure 5H:
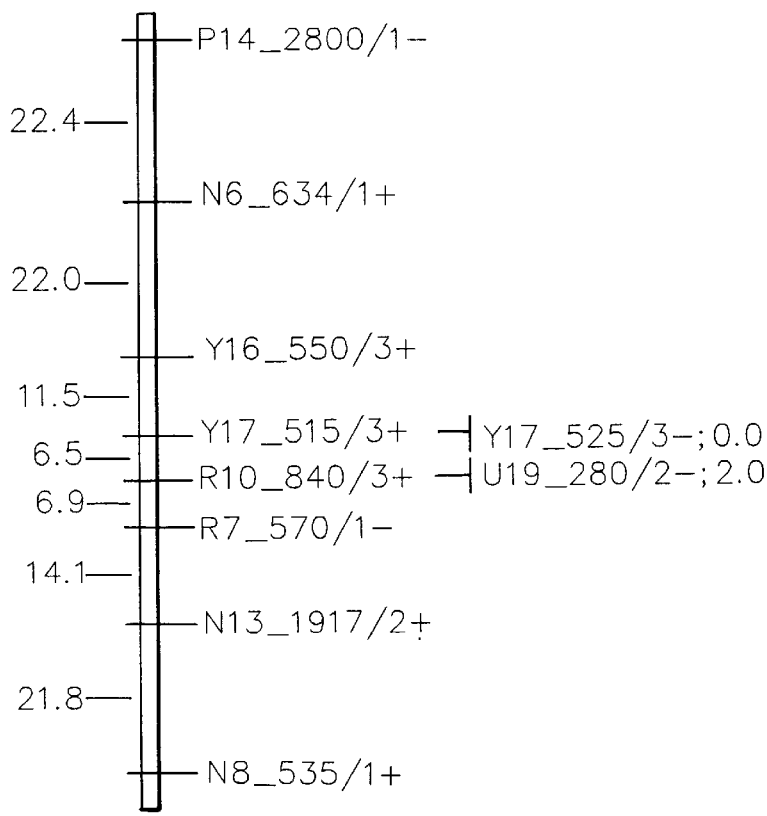
Figure 5H:
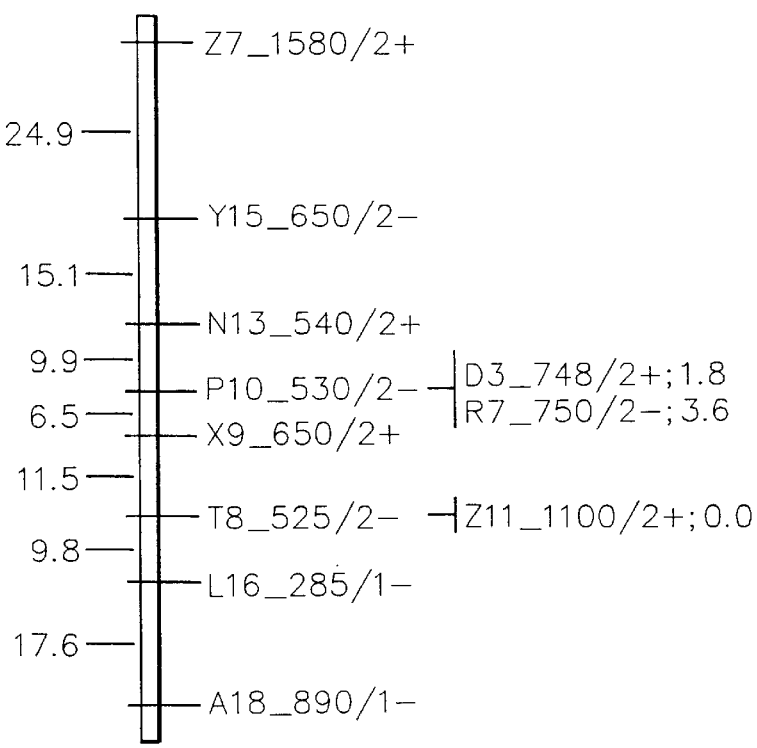
Figure 5I:
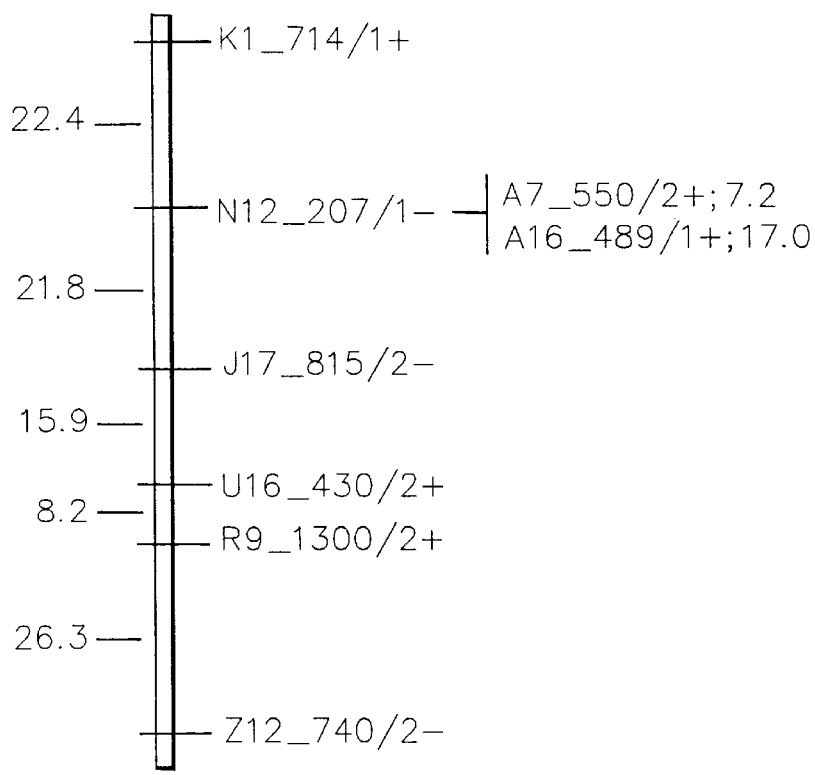
Figure 5I:
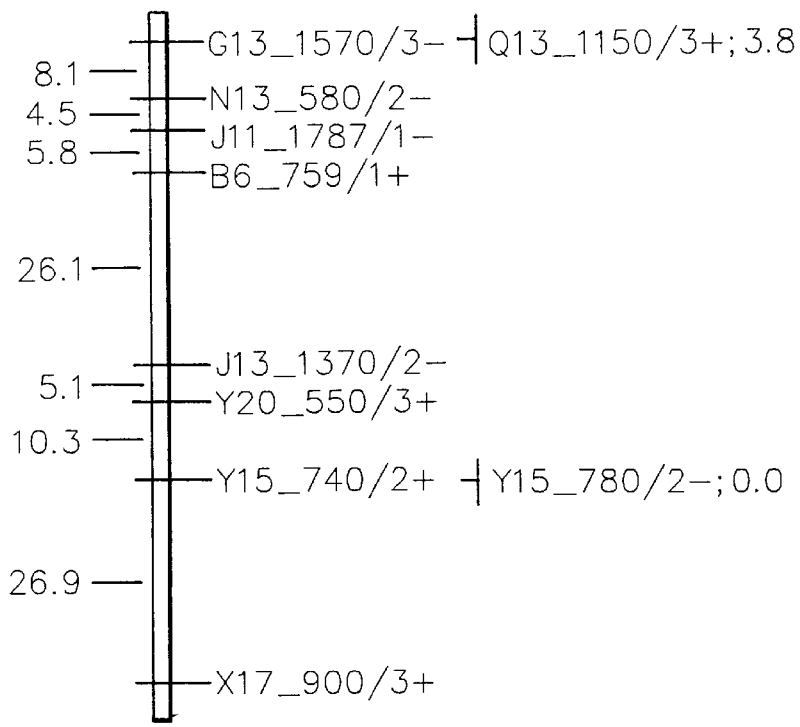
Figure 5J:
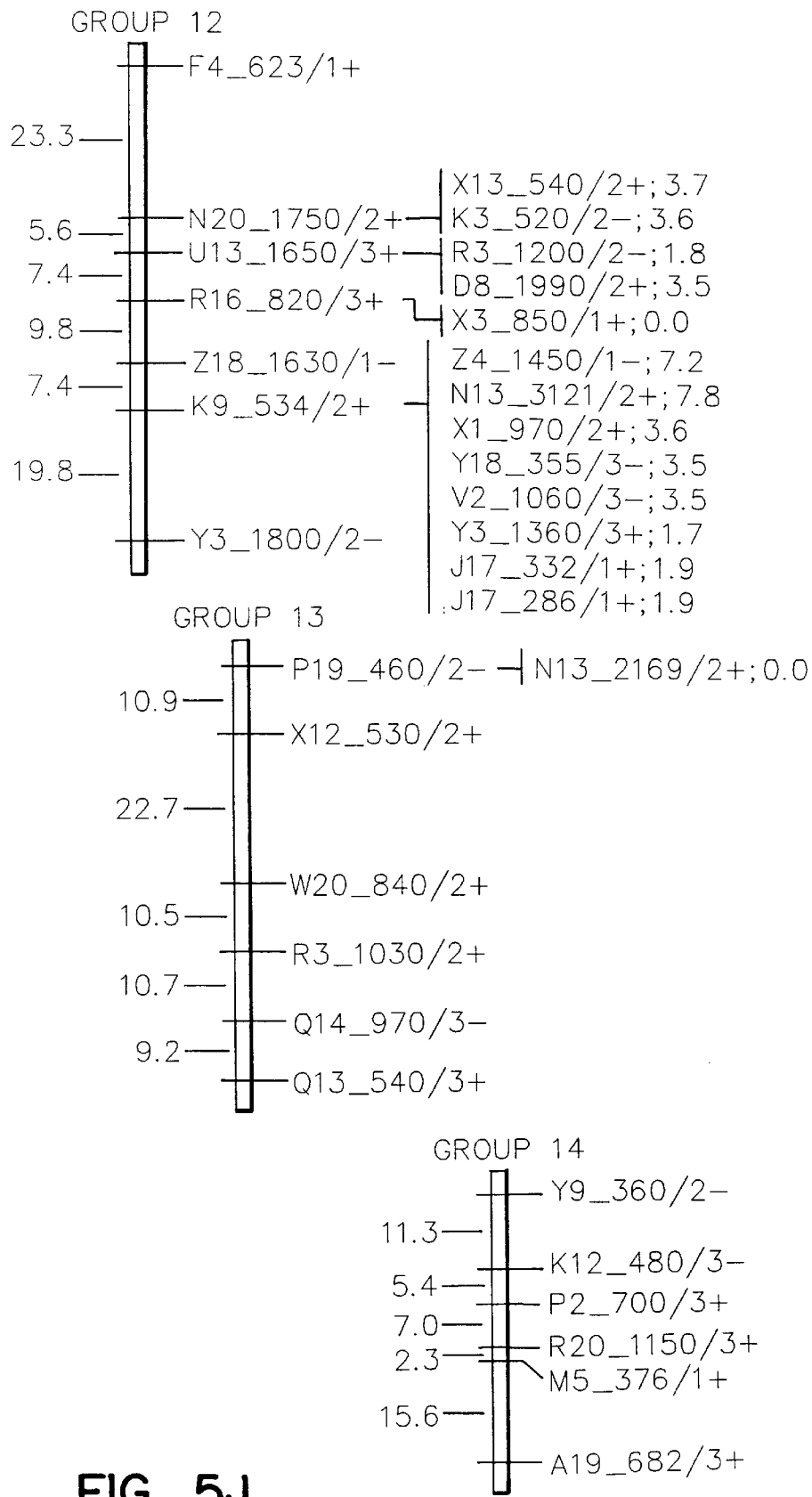

In the 10-5 family, resistance is putatively linked to a distal group of markers in a single linkage group (FIG. 4).

In Clone 10-5, the following markers were found to be predictive of resistance to inoculation with single Aeciospore line 20-21 (all markers are linked, i.e., on the same chromosome):

| Primer | Base Pair Sequence | Size (bp) | LOD Score |
|---|---|---|---|
| OPB8 | CTCCACACGG (SEQ ID NO:1) | 650 | 4.55 |
| OPK1 | CATTCGAGCC (SEQ ID NO:2) | 900 | 5.58 |
| OPD11 | AGCGCCATTG (SEQ ID NO:3) | 1300 | 5.45 |
| OPJ7 | CCTCTCGACA (SEQ ID NO:4) | 480 | 10.11 |
| OPJ4 | CCGAACACGG (SEQ ID NO:5) | 550 | 5.94 |
| OPC12 | TGTCATCCCC (SEQ ID NO:6) | 1200 | 4.99 |

In Clone 10-5 the following marker was found to be predictive of resistance to inoculation with single Aeciospore line 2-36:

| OPK17 | CCCAGCTGTG | 980 | 1.92 |
| | (SEQ ID NO:7) | | |

In Clone 152-231 the following marker was found to be predictive of resistance to inoculation with single Aeciospore line 2-36:

| OPC6 | GAACGGACTC | 1800 | 1.92 |
| | (SEQ ID NO:8) | | |

In Clone 152-257 the following marker was found to be predictive of resistance to inoculation with single Aeciospore line 20-21:

| OPJ7 | CCTCTCGACA | 480 | 3.56 |
| | (SEQ ID NO:4) | | |

These data indicate that the qualitative trait of resistance to fusiform rust disease in loblolly pine is under oligogenic control which can be mapped using genetic markers, using only a two-generation pedigree.

EXAMPLE 6

Studies in Eucalyptus Species

This example extends the analyses discussed above in Examples 2, 3 and 4.

Plant material: A single controlled cross between two highly heterozygous elite trees was selected for genetic mapping. *Eucalyptus grandis* (clone 44, Coffs Harbor provenance, Australia—selection from a Zimbabwe seed source), was used as the female parent and was crossed to *E. urophylla* (clone 28 selection from Rio Claro land race, Brazil), used as male. These two species belong to the same subgenus and section, and are easily crossed and their progeny are fully fertile. A second controlled cross used in the study was performed in the same year and location between a different female parent, *Eucalyptus grandis* (clone 816/2 Atherton provenance, Australia) and the same *E. urophylla* male parent. Seeds obtained from these crosses were surface sterilized in 1 percent sodium hypochlorite for 20 minutes, rinsed in sterile water and germinated on solid agar containing half-strength MS medium (Murashige and Skoog, *Physiol. Plant.*, 15, 473 (1962)) under a 14 hour photoperiod. The mapping population consisted of 62 F1 individuals. This population was immortalized by establishing clonal cultures of the individuals by vegetative propagation in vitro on half-strength MS medium supplemented with 0.005 mg/l IBA (indol-butyric acid) to stimulate rooting of microcuttings.

DNA Extraction: Total genomic DNA was isolated from freeze dried adult leaf tissue of the parents and from fully expanded leaves of in vitro plantlet progeny. A quick DNA miniprep procedure modified from Doyle and Doyle (*Focus*, 12, 13–15 (1987)) was used. Approximately 300 mg of fresh or 50 mg of freeze dried tissue was ground to a fine powder in liquid nitrogen directly in 1.5 ml microtubes using a plastic pestle. Eight hundred μl of extraction buffer (2 percent CTAB, 1 percent PVP, 1.4 M NaCl, 100 mM Tris-HCl pH 8.0, 20 mM EDTA pH 8.0 and 1 percent 2-mercaptoethanol) was added. Tubes were incubated at 65° C. for 30 to 60 minutes and inverted every 15 minutes. The tubes were brought to room temperature, then 700 μl of chloroform: isoamyl alcohol 24:1 was added and the tubes repeatedly inverted until a good emulsion was obtained. Tubes were centrifuged for phase separation (12,000×g, 5 minutes). The upper aqueous phase was transferred to a new tube containing 700 μl of ice-cold isopropanol. Tubes were gently inverted a few times until a precipitate could be seen. When precipitate was not easily visible the tubes were chilled at −20° C. for 30 minutes. DNA was pelleted by centrifugation (12,000×g, 10 min.) Pellets were washed once in 1.5 ml of 70 percent ethanol and once in 500 μl of 95 percent ethanol. Pellets were either dried in a speed-vac (Savant) or air-dried over night and then dissolved in 50 μl of TE buffer (10 mM Tris-HCl pH 8.0 and 1 mM EDTA pH 8.0) containing 50 μg/ml RNAse. DNA quality was checked on an agarose gel and the concentration estimated by comparing the fluorescence intensities of the ethidium bromide stained samples to those of lambda DNA standards. Samples were diluted to between 2.0 and 4.0 ng/μl DNA in sterile water for RAPD analysis.

RAPD assay: Random ten base primers (kits OP-A through OP-Z, Operon Technologies, Inc., Alameda, Calif.) were used. Amplification reactions (13 μl) contained 10 mM Tris-HCl pH 8.3, 50 mM KCl, 1. 5 mM $MgCl_2$, 0.1 percent Triton-X, 200 μM each of dATP, dCTP, dGTP, dTTP, 0.4 μM ten-base primer (corresponding to 32 ng), 0.1 mg non-acetylated Bovine Serum Albumin (New England Biolabs) 5–10 ng of genomic DNA and 1 U of Taq DNA polymerase. With a genome size of 0.6 pg/1C (see Grattapaglia and Bradshaw, *Can. J. For. Res.* (in press) (1994)) the amount of genomic DNA used in a RAPD reaction corresponds to between 8,000 and 16,000 haploid genome equivalents. Reaction mixtures were covered with 50 μl of mineral oil. Amplifications were performed in disposable polyvinylchloride 96-well microtest plates using an MJ Research PT-100 thermal controller programmed for 41 cycles of 1 min at 92° C., 1 min at 35° C. and 2 min at 72° C. with a ramping time of 3 sec/1° C. Amplification products were analyzed by submarine horizontal electrophoresis in 1.5 percent or 2.0 percent agarose 1×TBE gels containing 0.2 μg/ml ethidium bromide (Maniatis, Fritsch and Sambrook, 1982). Gels were run at 10 V/cm in a Biorad H4 model electrophoresis apparatus on a custom made gel tray that allows running three 10-centimeters tiers each with 34 samples. A full 96-well plate could thus be run on a single gel. Gels were photographed under transmitted UV light using a MP4 POLAROID™ camera with either 665 or 667 POLAROID™ film. Alternatively, gel images were captured using an EAGLEYE™ video imaging system (Stratagene) and printed on 20×15 cm thermal paper. Gel scoring was performed directly from the photographs or thermal prints.

Primer screening: A total of 305 ten-base random primers (Operon Technologies Inc.) were screened against the two parents and a progeny sample of 6 individuals. RAPD fragments that are polymorphic between the two parents and segregate in the progeny can be detected. With 6 individual progeny the probability of missing a polymorphic marker segregating 1:1 is 0.094. Twelve primers were conveniently screened on one 96-well plate and one gel. A total of 151 primers were selected during this step based on the number of RAPD polymorphisms amplified, their size and amplification intensity. Selected primers were used on the mapping population.

Scoring of RAPD markers: Segregation of RAPD markers in the mapping population was recorded in two independent replications, each one with a different set of individuals. In the first replicate the two parents and 30 progeny were assayed for RAPD markers with all the selected primers. In a second replicate, totally independent DNA extractions, reaction mixture preparations, gel analysis had genotype scoring were performed for another set of 32 individuals. In a 96-well format, three sets of 32 individuals could be analyzed with 3 random primers per plate/gel. This procedure provided an internal control and an estimate of repeatability for virtually all the scored markers. Markers that did not amplify consistently or could not be scored reliably across the two replicates were dropped from analysis.

Segregating RAPD markers were identified by the manufacturer primer code (Operon Technologies Inc., Alameda, Calif.) corresponding to a particular ten-base sequence, followed by an underscore, then a number indicating the fragment size in base pairs. (Primers were designated as follows: Each "kit" from Operon Technologies was identified by a letter (A-Z, AA-ZZ, etc.). Each kit contained 20 primers, labeled 1–20. Each primer was a randomly-ordered, 10 base-pair sequence assigned by a computer. A complete listing of all primers can be found in the Operon Technologies Catalog, and can be obtained from the company at 1-800-688-2248, or at 1000 Atlantic Avenue, Alameda, Calif. 94501.) Fragment sizes were estimated using the software SEQAID II (Rhoads, D. D. and Roufa, D. J. SEQAID 3.80, Kansas State University, Molecular Genetics Laboratory (1990)). Following the fragment size, separated by a slash, a subjective score was given from 1 to 3 denoting the fragment amplification intensity (3 being most intense). For example RAPD marker $A11_{13}$ 980/3 corresponds to a RAPD fragment amplified by Operon primer A11 (corresponding to the sequence 5'-CAATCGCCGT-3', SEQ ID NO. 22) with 980 base pairs in size, of high (score 3) amplification intensity. (Sequences of primers for markers associated with traits for all Examples herein are listed in TABLE 2.)

All the scored RAPD fragments were sampled from the agarose gel by gently stabbing the fluorescing band with a pipette tip and rinsing the tip into 20 μl of sterile TE buffer (10 mM Tris-HCl and 0.2 mM EDTA). All samples were stored at −20° C. until required for reamplification when performing RAPD fragment copy number characterization and homology survey.

Use of RAPD bands as hybridization probes: RAPD fragments to be used as hybridization probes were reamplified using the RAPD assay conditions described previously. Template DNA for reamplification consisted of a 3 μl volume of the 20 μl RAPD band sample. Non-radioactive labelling of the probes was performed by substituting 5 percent of dTTP with dUTP-digoxigenin (Boehringer-Mannheim) in the nucleotide mixture. Reamplifed probes were checked for single band purity on a mini-gel, diluted to 5 ng/μl in TE and stored until later use.

Confirmation of RAPD marker inheritance. codominance and presence in different individuals: Putative codominance (size-variation) of RAPD markers was investigated by DNA hybridization of gel blots of RAPD products with the putative codominant fragment used as probe. A subset of mapped RAPD markers were surveyed for their presence and segregation in a different individual of E. grandis by analyzing the second F1 cross described previously. RAPD assay was carried out on the two parents and 10 progeny for each one of the two crosses. RAPD products were run side by side on a gel. Confirmation of homology for RAPD markers of same size was carried out through DNA hybridization, using the fragment of interest as a probe. RAPD gels were blotted onto nylon membranes and hybridized described previously for genomic Southern blots.

Segregation and Linkage Analysis of RAPD Markers: Segregating markers were scored for presence (1) or absence (2) of the amplified RAPD band. The parental origin of the marker was also recorded. Two separate data sets were obtained, one for each parent. In the pseudo-testcross configuration all markers are single dose. They are present in one parent and absent in the other or vice versa, and are expected to segregate 1:1 in the F1 generation. a Chi squared test ($\alpha$=0.05) was performed to test the null hypothesis of 1:1 segregation on all scored markers using a program in BASIC. Preliminary grouping was done using a chi squared test for independence of segregation at a threshold of 15.00 (corresponding approximately to a LOD score of 5.0, R. Doerge, personal communication). The linkage analysis was done using MAPMAKER (Lander et al., Genomics, 1, 174–181, (1987)) version 1.0 for MacIntosh and version 3.0 for UNIX. The software program GMENDEL (Liu and Knapp, version 2.0, Oregon State University (1992)) was also used during linkage analysis particularly for ordering linkage groups. The MAPMAKER model assumes that all markers are in coupling phase. Therefore to allow the detection of linkage of RAPD markers that belong to the same linkage group but are in repulsion phase the data set was duplicated and recorded (1 for absence of a band, 2 for presence of a band). A LOD score of 5.0 was set as a linkage threshold for grouping markers into linkage groups. When working with the MacIntosh version where no backcross option was available and the default routine for F2 populations was used, to analyze markers segregating 1:1, this threshold doubles to a LOD score of 10.0 (Reiter, et al., Proc. Nat. Acad. Sci., 89, 1477–1481 (1992). A maximum recombination fraction of 0.25 was used. Map distances in centimorgans (cM) were calculated from recombination frequencies using Kosambi's mapping function that takes into account interference (Kosambi, Ann. Eug., 12, 172–175 (1944)). Preliminary orders of marker loci in each linkage group were established using a matrix correlation method implemented in the MacIntosh version of MAPMAKER. From this initial order, a subset of evenly spaced landmark loci that could be ordered with a likelihood ratio support >1000:1 established a framework map. Error detection functions of MAPMAKER 3.0 were employed in the framework selection. The final framework order obtained was then compared to the order outputted for the same subset of marker loci by GMENDEL that employs a seriation algorithm. Markers that could not be ordered with equal confidence were indicated as accessory markers at an already specified locus on the map. Genome map sizes were estimated according to Hulbert, et al., Genetics, 120, 947–958 (1987), taking into consideration only pairwise comparisons between markers placed on the framework map.

RESULTS

Primer Screening: In our standard conditions, RAPD reactions amplified an average of 10.7 visible bands on an ethidium bromide stained agarose gel. Primer screening was efficiently carried out using both parents and sample of F1 individuals (FIG. 1). With this format, parental origin of the polymorphic loci as well as their allelic state (homozygous or heterozygous) was directly inferred from the presence of the fragment in one parent, the absence in the other and at least one presence/absence in the F1 progeny sample. Of the 305 arbitrary primers screened, 57 (18.7 percent) did not yield any amplified product, 50 (16.4 percent) did not detect any visible sequence polymorphism in our particular cross and 198 (64.9 percent) uncovered at least one RAPD fragment polymorphism. From these 198 primers, a total of 151 were selected, aiming at maximizing the number of scorable markers per primer in the following mapping step. A total of 558 RAPD markers were scored on the mapping population, yielding an average of 3.69 markers/selected primer or 1.82 markers/any arbitrary primer. Similar ratios were recently reported for single-dose RAPD polymorphisms in sugar can (1.88) (Sobral et al., *Theor. Appl. Genet.*, 86:105–112 (1993)) and *Stylosanthese* (1.8) (Kazan et al., *Genome*, 36:50–56 (1993)). Although the majority (64.9 percent) of primers screened detected at least one polymorphism, the screening step essentially doubled the time efficiency and halved the cost of data gathering in the mapping phase.

Scoring of Markers on the Mapping Population: Segregation of a total of 558 RAPD markers was scored on the mapping population consisting of 62 F1 individuals (FIG. 2). The number of markers inherited from each parent were very similar: 272 from the maternal parent *E. grandis* and 286 from the paternal parent *E. urophylla*. RAPD fragments sizes ranged from 3335 bp to 207 bp, with an average of 979 bp, a standard deviation of 570 bp, a median of 840 bp and a mode of 600 bp for *E. grandis* and in the same order 910 bp, 521 bp, 770 bp and 700 bp for *E. urophylla*. The replicated design used (see Material and Methods) throughout the mapping phase provide a data quality control system and allowed the identification of unreliable RAPD markers. A repeatability estimate of 92.4 percent was obtained with this procedure. From the 558 RAPD markers, 516 were fully repeatable in both replicates while 42 did not behave so, 20 from *E. grandis* and 21 from *E. urophylla*. These markers either could be scored in the first set of progeny and not in the second or vice versa. With no exception, all the 42 markers that could not be repeated under the standard conditions were originally classified as class 1 markers denoting low amplification intensity and/or difficulty in scoring due to co-migrating fragments. Such fragments were not considered in further analysis.

Figure 8A:
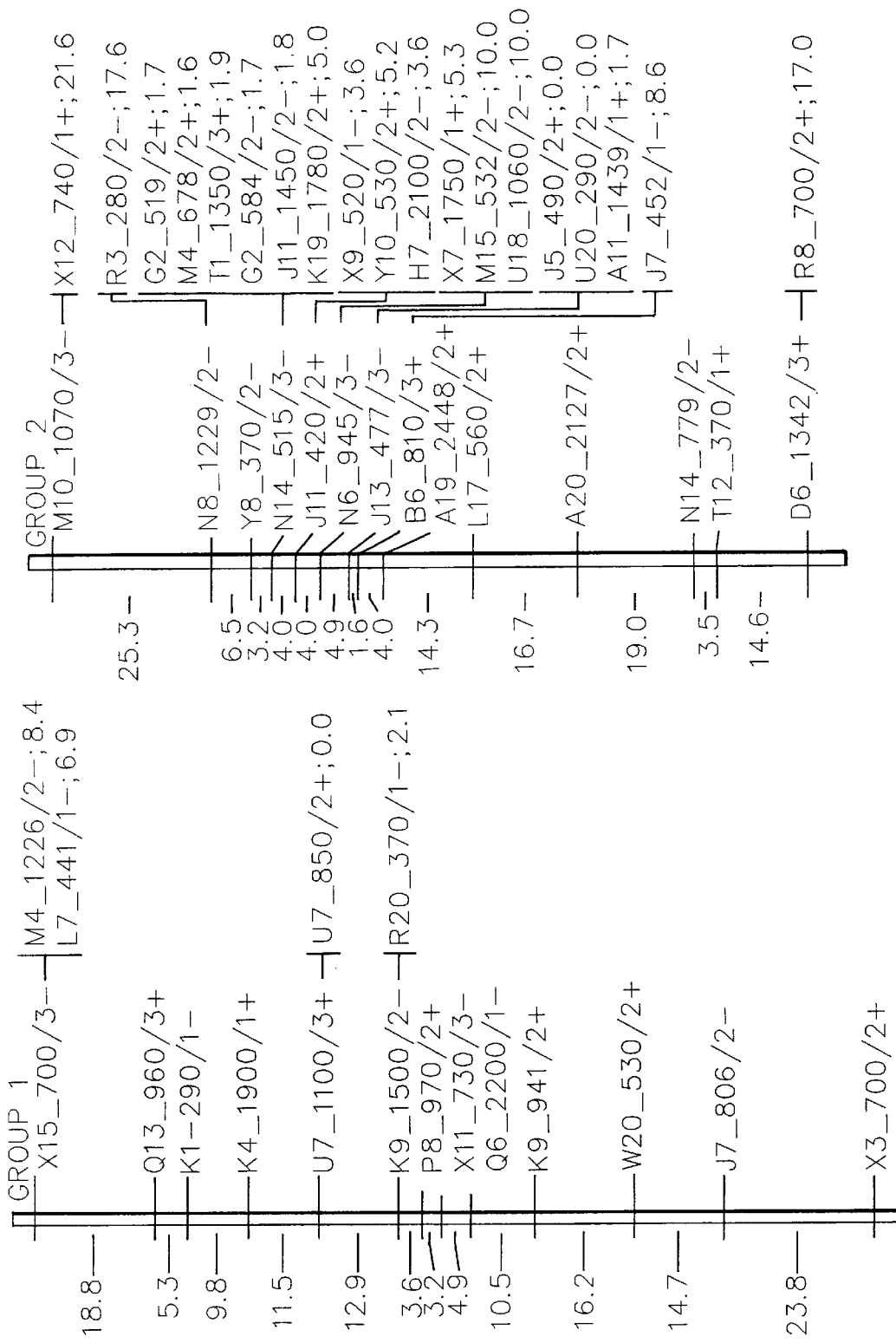
Figure 8B:
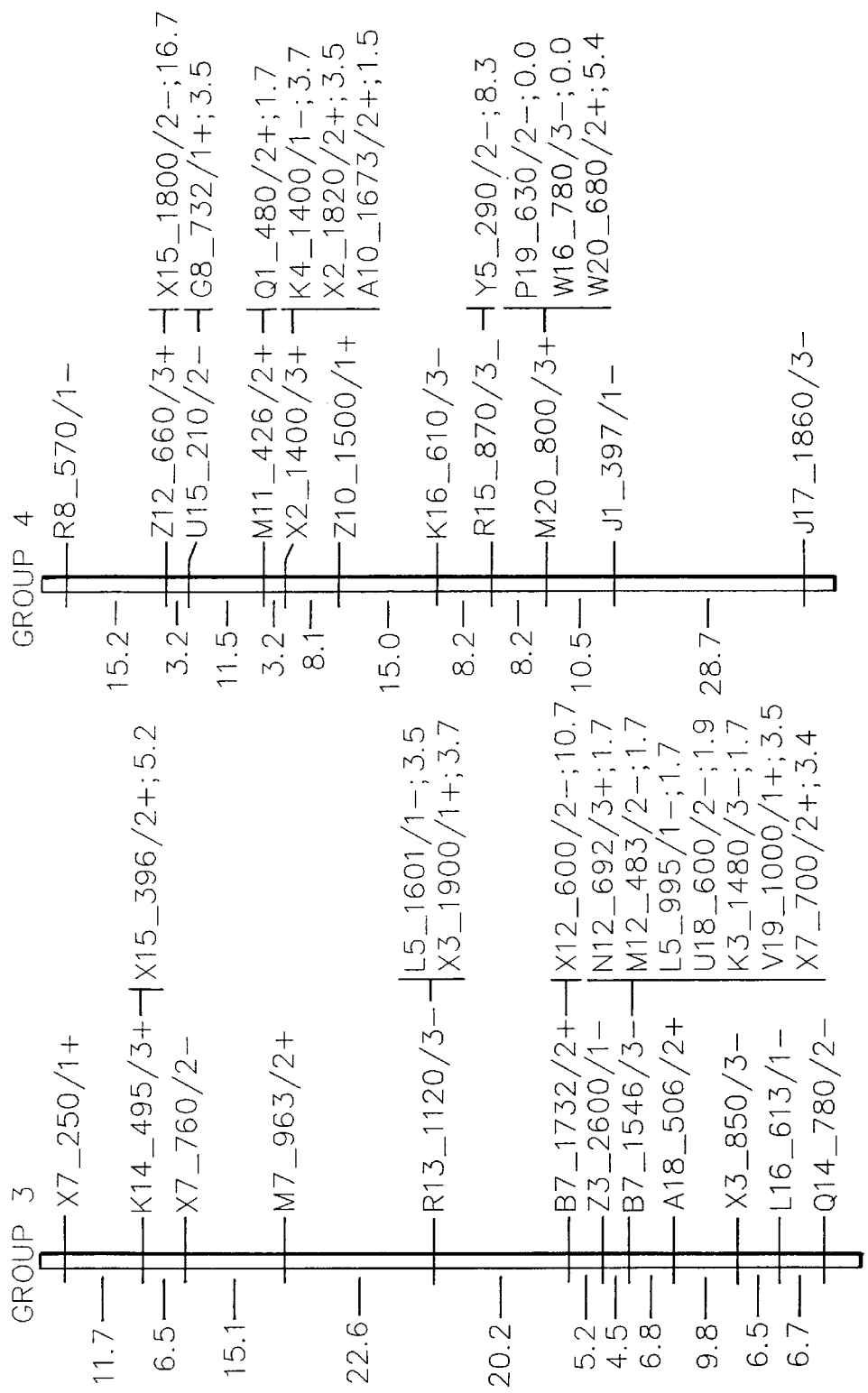
Figure 8D:
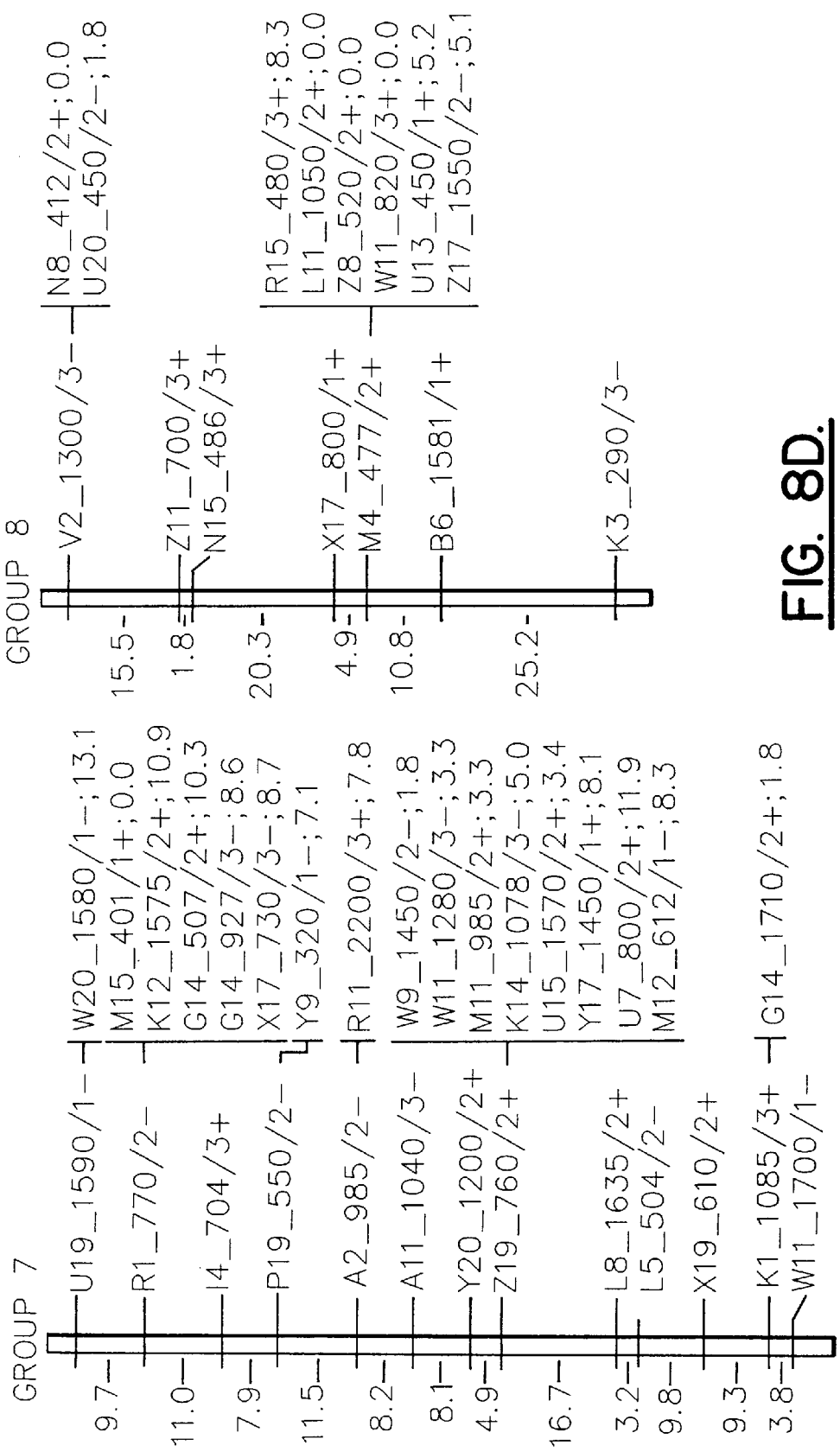
Figure 8E:
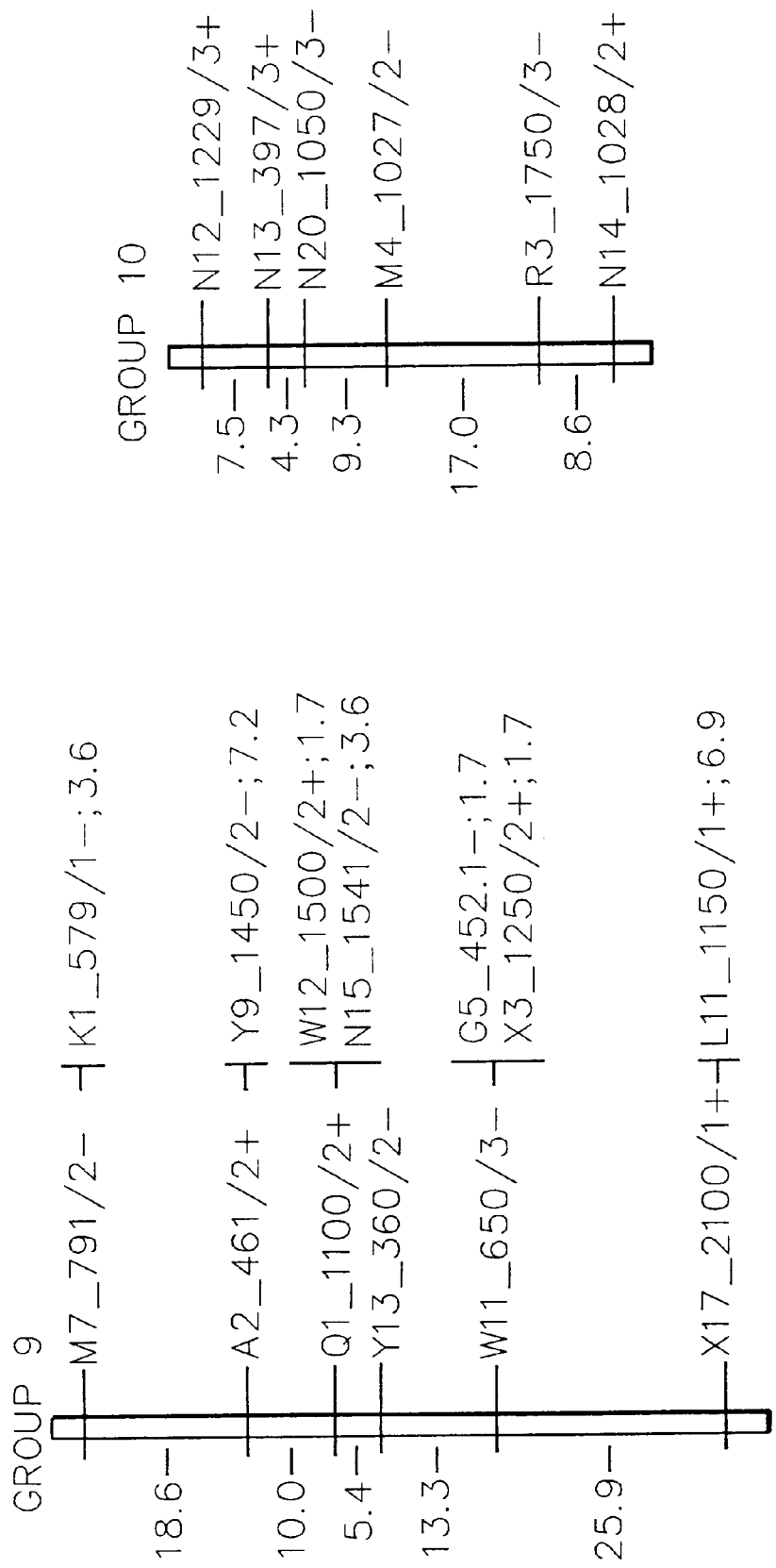
Figure 8F:
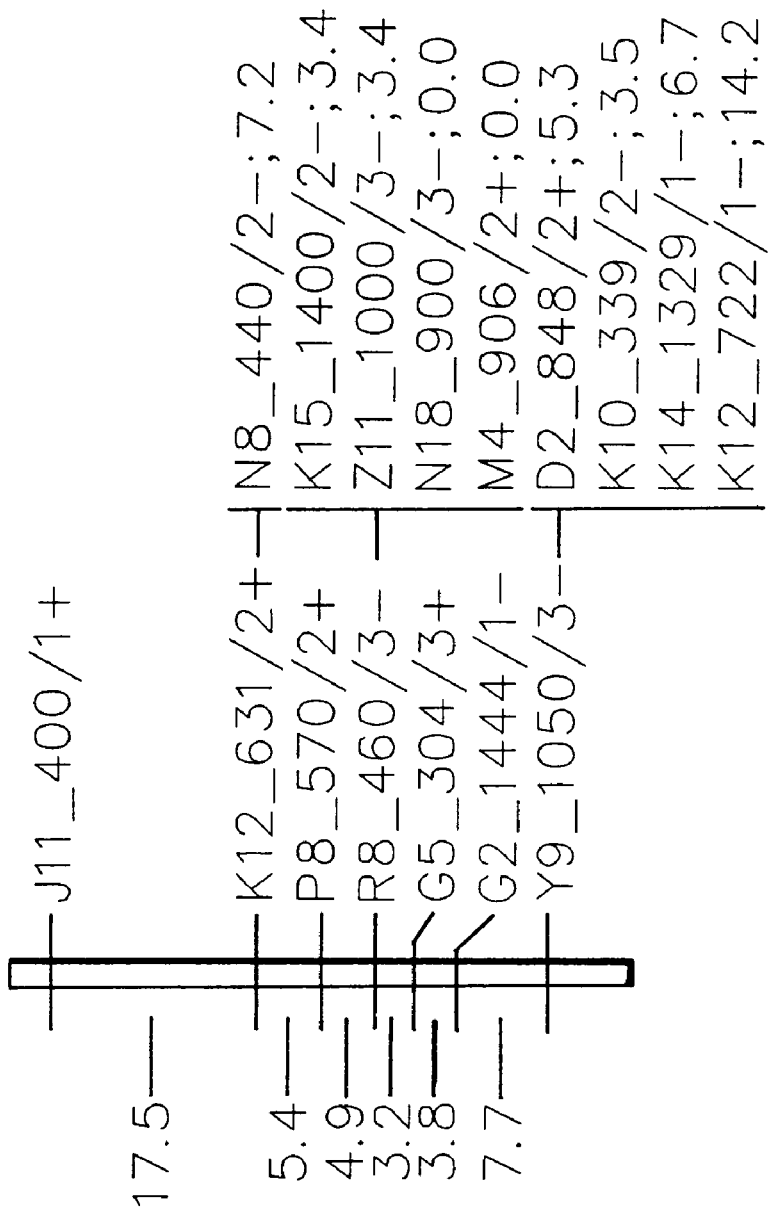
Figure 9A:
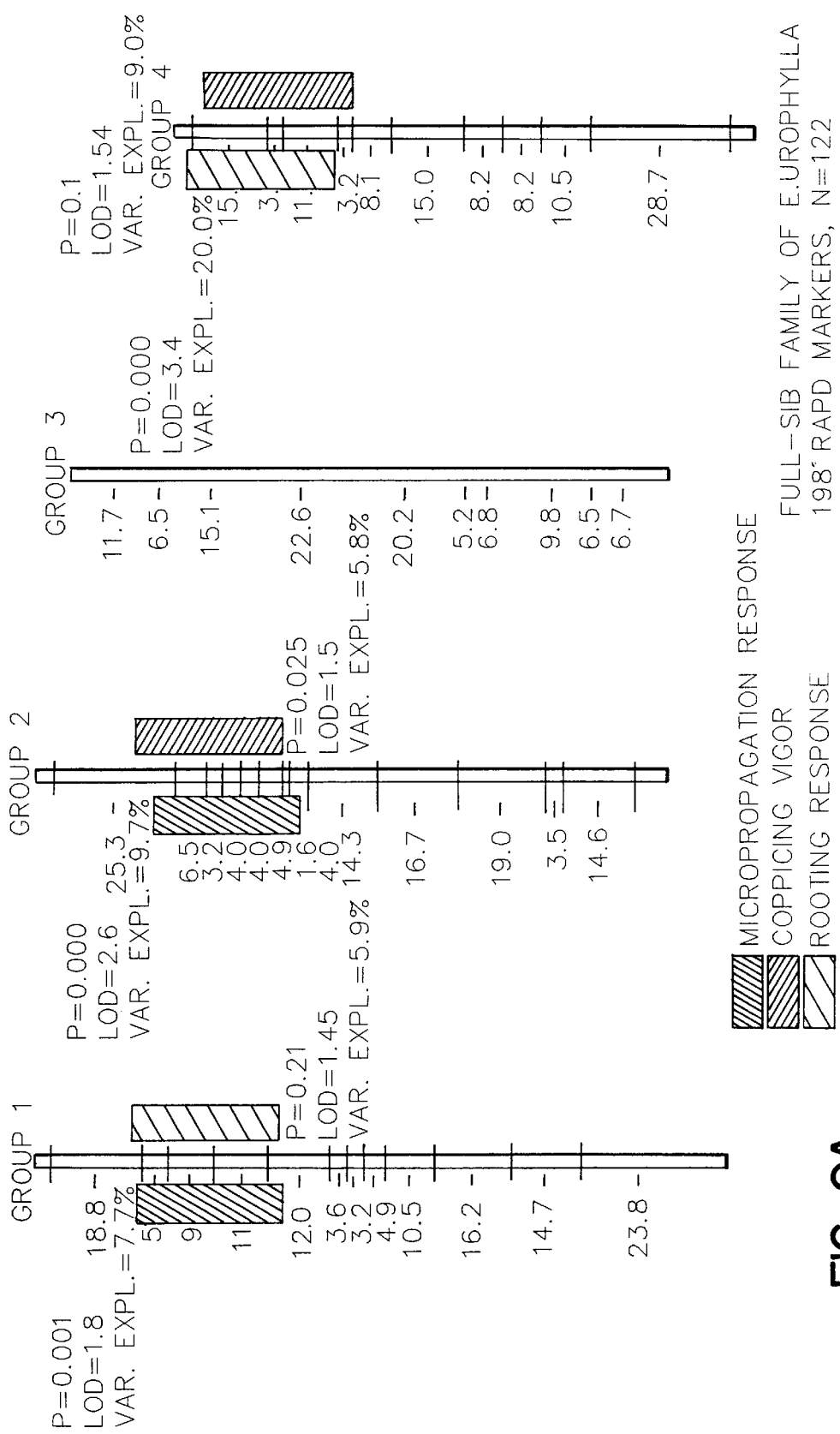
FIGS. 9A–9C together comprise a genomic map of an *E. urophylla* individual showing markers representing most regions of the genome, and showing the approximate locations of markers that are statistically associated with quantitative traits of progeny in a full-sib family. These regions of strong marker: trait association are indicative of the existence of one or more QTL in these regions.
Figure 9B:
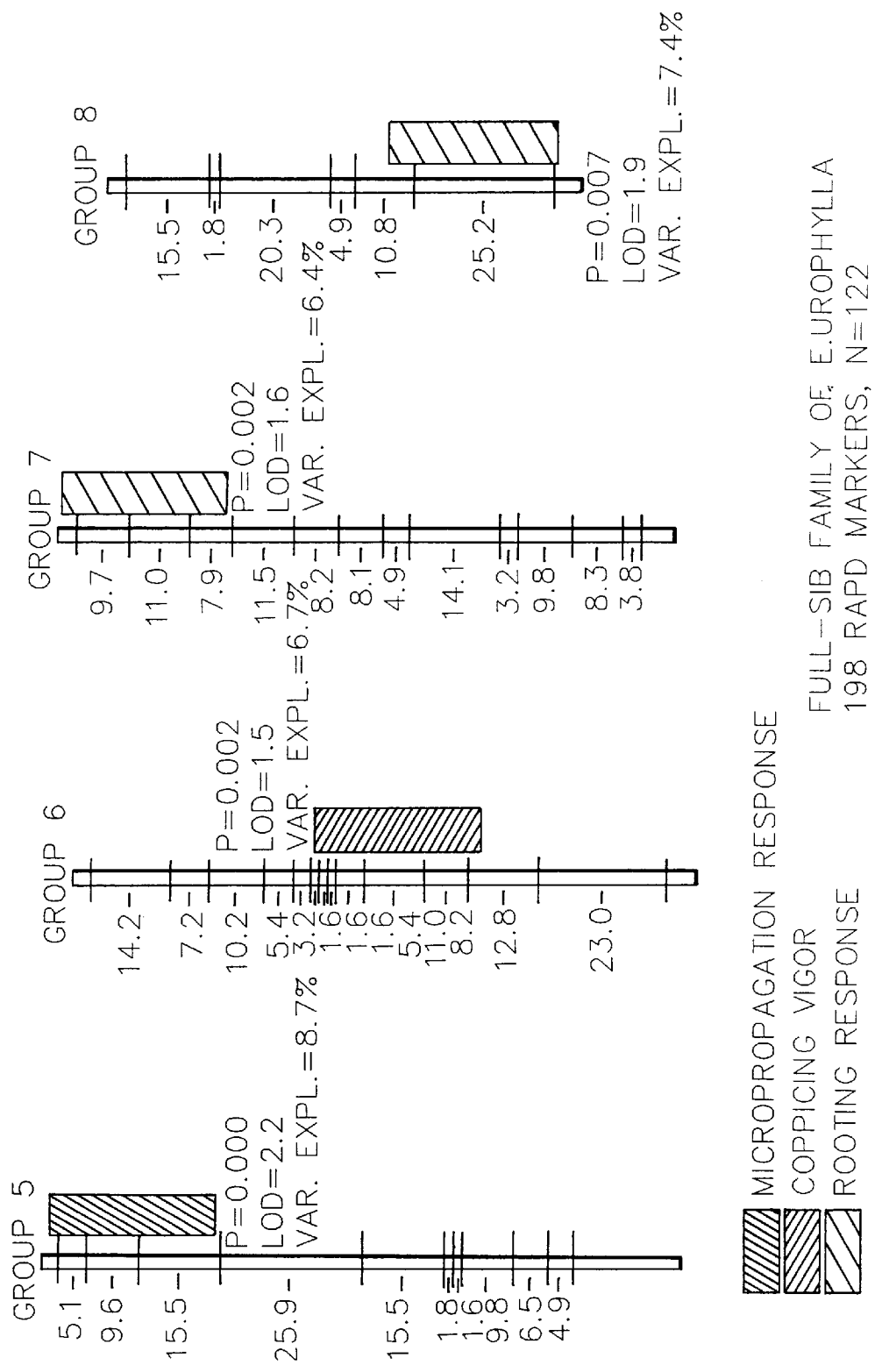
Figure 9C:
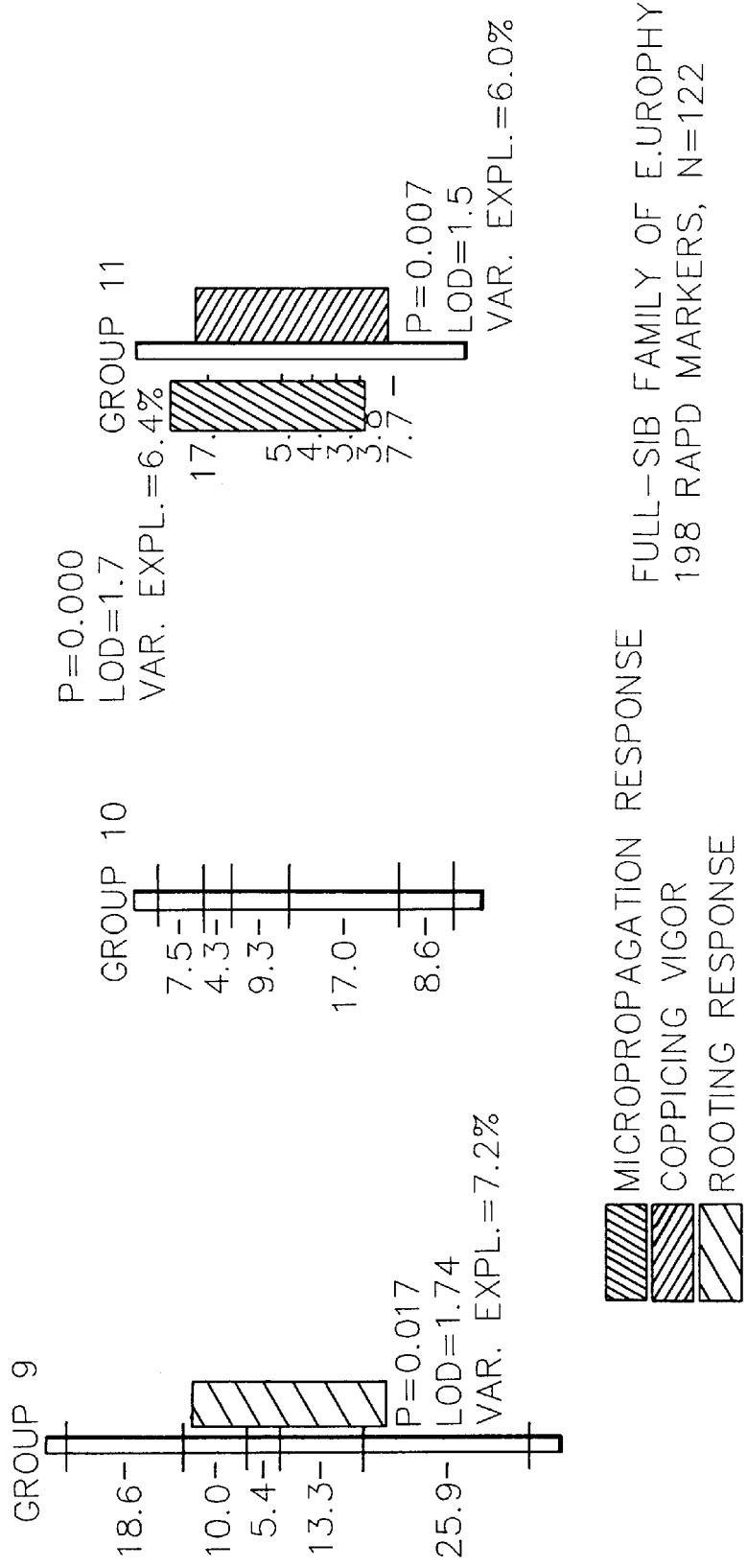

Linkage Analysis: Segregation ratios that departed from the Mendelian expectation of 1:1 at $\alpha=0.05$ were detected at 10 marker loci in *E. grandis* and 10 marker loci in *E. urophylla*. No departure was detected at $\alpha=0.01$ (critical $\chi^2=63$). These apparently distorted markers (denoted with an accompanying asterisk following the marker identification) are clustered on only 2 linkage groups in *E. grandis* (groups 6 and 7) but are scattered in 6 linkage groups in *E. urophylla* (FIGS. 8A and 8B). Note that a $\alpha=0.05$, considering a total of 500 marker loci, around 25 of these are expected to display this behavior due to chance. The distortions detected might therefore have no biological basis. Only markers that passed the single-locus segregation test were initially used in the MAPMAKER linkage grouping analysis. Distorted markers were later placed into linkage groups using the NEAR and TRY commands. These commands used sequentially determined the most probable location of a marker in an already established gene order.

Linkage relationships of the segregating markers were established using both a simple $\chi^2$ test for independence of segregation at a threshold value of 15.00 and the two-point GROUP command of MAPMAKER with a LOD score 5.0 (LOD 10.0 when using the MacIntosh version 1.0, see Material and Methods) and maximum recombination fraction ($\theta$) 0.25 as linkage thresholds. Although the stringency of the $\chi^2$ analysis was slightly higher, both linkage analyses agreed very closely. Overall, linkages were robust at a LOD score range from 4.0 to 6.0. In view of the larger number of markers, at lower LOD scores, especially below 4.0, occasional spurious linkages resulted in the agglomeration of some linkage groups, while increasing LOD scores beyond 6.00 would result in fragmentation of linkage groups. Final grouping and map assembly was carried out at LOD 5.0. Such stringency resulted in the maternal *E. grandis* map having a total of 240 markers into 14 linkage groups and the paternal *E. Urophylla* map with 251 markers in 11 linkage groups (FIGS. 3 and 4). Twelve markers for *E. grandis* and 13 for *E. urophylla* remained unlinked at LOD 5.0. Although they were linked at a lower LOD (3.0), and higher $\theta$ (0.35), they did not contribute any significant additional information in terms of genome coverage and therefore they were left out from the final map versions. The proportion of unlinked markers found (4.5 percent) is smaller than those reported for other single-dose marker linkage mapping studies (e.g., 10 percent in potato (Gebhart et al., *Theor. Appl. Genet.*, 78:65–75 (1989)); 15.4 percent and 12.9 percent in sugar cane (Al-Janabi et al., *Genetics*, 134:1249–1260 (1993)).

Locus ordering and map construction: Both Eucalyptus species have n=11 chromosomes, and therefore 11 linkage groups were expected in each map. At the LOD threshold adopted (5.0), this expectation was met for the *E. urophylla* map but not for the *E. grandis* map. However, for *E. grandis*, lowering the threshold LOD score to 4.0 and increasing $\theta$ to 0.35 would result in the merging of 3 pairs of linkage groups leading therefor to a correspondence between number of linkage groups and number of chromosomes. The following mergers with the respective highest LOD score between markers on separate groups would take place: groups 8 and 12 (LOD score 4.3 between markers N6_634/1 and K9_534/2); groups 11 and 13 (LOD score 4.4 between markers B6_759/1 and X12_530/2); groups 1 and 6 (LOD score 4.05 between V7_450/2 and L16_389/2) (FIG. 3). In spite of the possibility of merging some linkage groups to attain the expected number of chromosomes, it was found more appropriate to assemble both maps with the same statistical stringency allowing for more meaningful comparisons between maps. An excess of linkage groups in relation to the haploid chromosome number has been reported for other species (e.g., bean (Nodari et al., *Theor. Appl. Genet.*, 85:513–520 (1993)); lettuce (Kesseli et al., *Genetic Maps*, Cold Spring Harbor Laboratory Press, pp. 6100–6102 (1990)).

The linkage groups were constructed using markers in both linkage phases. Repulsion phase markers were assigned using the data set doubling and recording procedure so as to put all the markers as though they were in coupling, allowing MAPMAKER to recognize the data input (see Material and Methods). On the linkage maps, markers on one linkage phase are indicated with a "+" sign following the marker identification code, while markers on the alternative phase are indicated with a "−" sign (FIGS. 3 and 4).

The FIRST ORDER procedure of the MacIntosh version of MAPMAKER was used to get a preliminary ordering. This ordering algorithm is extremely fast and conveniently handles larger numbers of markers simultaneously although local ambiguities usually still exist in the resulting order, particularly for closely linked markers. Based on this first approximate order, a subset of candidate framework marker loci was selected spanning the whole linkage group at distances varying between 5 and 20 cM. This selection was based on a sequence of criteria, that by order of priority were as follows: (i) fragment intensity of amplification score; (ii) ease of marker scoring in view of co-migration of other fragments of smearing that could lead to errors in genotyping (gel photo was reviewed); (iii) number of missing date;

(iv) size of amplified fragment (below 2000 and above 300 basepairs). Candidate framework markers selected were again ordered using the FIRST ORDER command. This linear order was then tested by permutating all possible sets of 3 adjacent marker using the RIPPLE command. A final framework order was accepted when the log-likelihood difference between the initial order and all the alternative permutations was at least −3.0. Therefore, the framework map orders presented are approximately 1000 times more likely than the next best orders. For 12 of the 25 linkage groups analyzed, a final framework order was obtained immediately following the selection of framework markers. For the remaining groups, local differences of less than −3.0 were observed, particularly but not restricted to closely spaced markers. In those cases additional markers were excluded from the framework at the regions of ambiguous ordering, and the FIRST ORDER and RIPPLE analyses performed again. Generally, after one or two such iterations, a final order was attained. This final framework order was then compared to the order obtained by the seriation algorithm implemented by GMENDEL. With the exception of a few two-marker order permutations the framework orders obtained were the same.

Markers that could not be placed on the map with a 1000:1 odds were designated as accessory markers and were positioned on the map in relation to the closest framework marker. Their most likely position was obtained using the NEAR command and looking for the framework locus that displayed the highest LOD score and lowest two-point θ, or alternatively with the TRY command looking for the interval with log-likelihood closest to zero. Markers that belong to the framework are indicated with bold letters. Accessory markers are listed on the right along with the approximate cM distance to the closest framework marker (FIGS. 3 and 4).

Clustering of markers was found throughout both linkage maps, particularly in *E. urophylla* that displays large clusters on groups 2, 5, and 6. Clustering is a common occurrence and has been reported in essentially all relatively dense linkage maps constructed to date irrespective of the organism or technique used to assay DNA polymorphisms: RFLP in common bean (Vallejos et al., *Genetics*, 131:733–740 (1992)); RAPD in Arabidopsis (Ritter et al., *Genetics*, 125:645–654 (1990)) or microsatellites in humans (Weissenbach et al., *Nature*, 359:794–801 (1992)).

The great majority of the accessory markers are within 5 cM from the nearest framework marker. It is likely that their ordering ambiguity results largely from the relatively small recombinational distance estimated from a limited number of meioses analyzed. With 62 meioses, the standard error on a recombination fraction of 0.05 is approximately 0.03. However, in both maps, not considering markers showing segregation distortion, which were deliberately left out of the framework, 25 percent of the accessory markers (22 in 88 for *E. grandis*) and 18.5 percent (25 of 135 in *E. urophylla*) were at distances greater than 6 cM (θ~0.05) and could still not be placed in the framework. The ambiguity in the placement of this group of markers might be the result of missing data or to errors in genotyping. In our experimental conditions, a genotyping error rate ≦3 percent was estimated, varying with the RAPD fragment amplification intensity.

Linkage Maps Statistics and Estimates of Genome Size and coverage: Approximately 59 percent of the markers for *E. grandis* could be placed on the framework defining a total of 142 loci or loci clusters and 1551 cM of total map distance. For *E. urophylla* 47 percent of the markers could be placed on a framework of 119 loci or loci clusters covering 1101 cM (FIGS. 3 and 4). Linkage groups were numbered sequentially from the longest to the shortest. For *E. grandis* the average size of linkage groups was 110±35 cM and the range from 41.6 cM to 156.9 cM. For *E. urophylla* the average size was 99±32 cM and the range from 46.7 to 141 cM. The total number of markers per linkage group (framework and accessory) varied from 6 (group 14) to 30 (group 5) for *E. grandis*, and from 6 (group 11) to 39 (group 6) for *E. urophylla*. The average distance between two framework markers was 12.2±6.3 cM for *E. grandis* and 10.2±6.6 cM for *E. urophylla*. Both maps have a density of 27 cM, which corresponds approximately to a recombination fraction of 0.25 (i.e., no interval between two markers is greater than 27 cM).

Total genome size was estimated for both parents using the method of Hulbert et al., *Genetics*, 120:947–858 (1987), as described by Vallejos et al., *Genetics*, 131:733–740 (1992). MAPMAKER's TWO-POINT routine was used to determine K, the expected number of marker pairs linked with a θ≦0.25 (corresponding to 27 cM under Kosambi's function) and a LOD score ≧5.0. Only framework markers were used in this procedure to avoid an upward bias in K that later would result in an overestimate of genome coverage. For *E. grandis*, the maternal parent, a total map distance of 1620 cM was estimated, of which 1552, i.e., 95.8 percent, were covered by the framework map. For *E. urophylla*, the paternal parent, the total map distance estimated was 1156 cM, of which 1101 cM, i.e., 95.2 percent, were covered. A reasonably equivalent genome coverage in both species and sexes was therefore achieved with the pseudo-testcross mapping strategy. Given the estimated total map distances and genome size of 641 and 646 Mbp/1C (Grattapaglia et al., *Can. J. For. Res.* (in press), (1993)), the average physical equivalent of 1 cM would correspond to 395 and 559 kilobase pairs, respectively for *E. grandis* and *E. urophylla*.

Figure 6A:
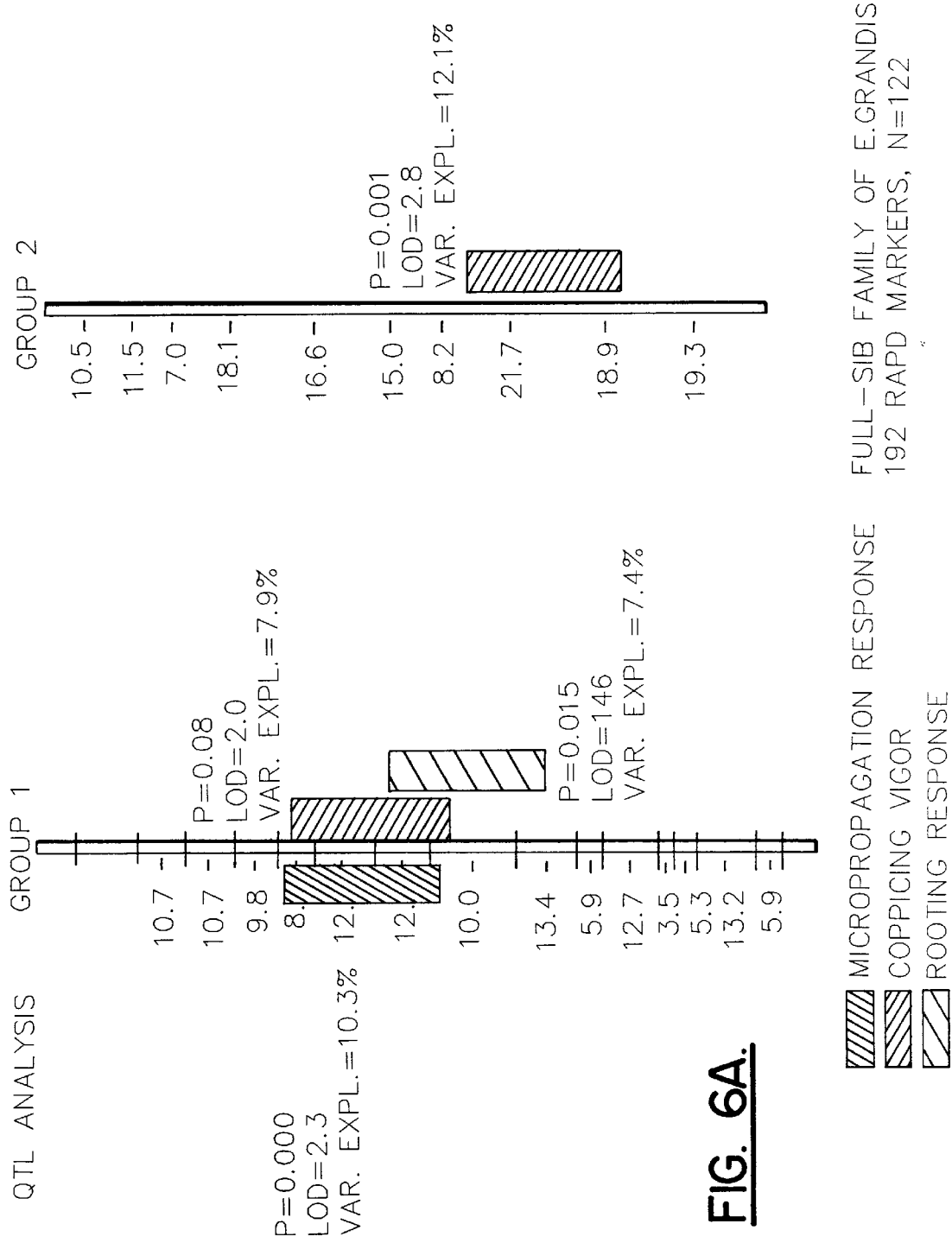
Figure 6B:
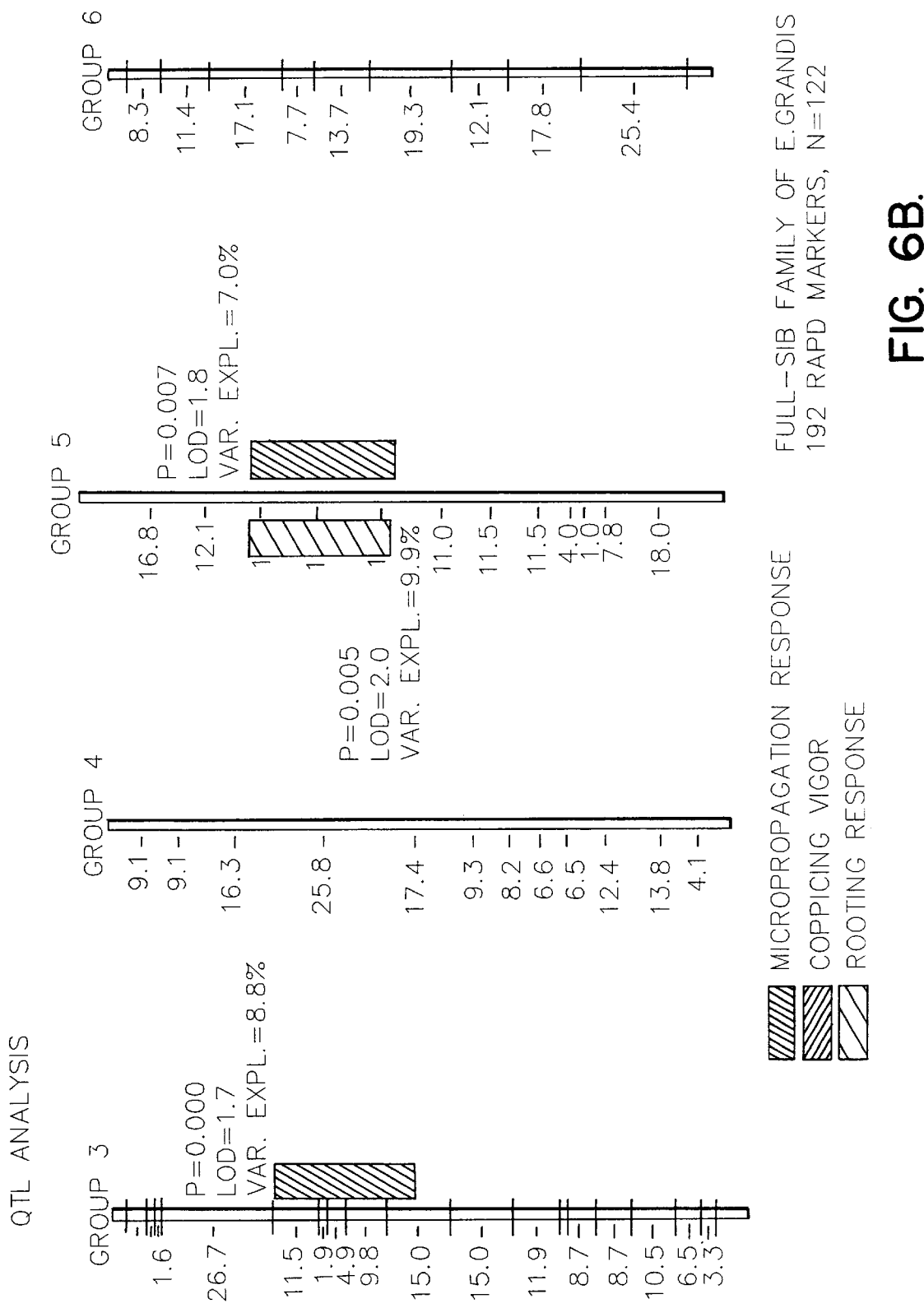
Figure 6C:
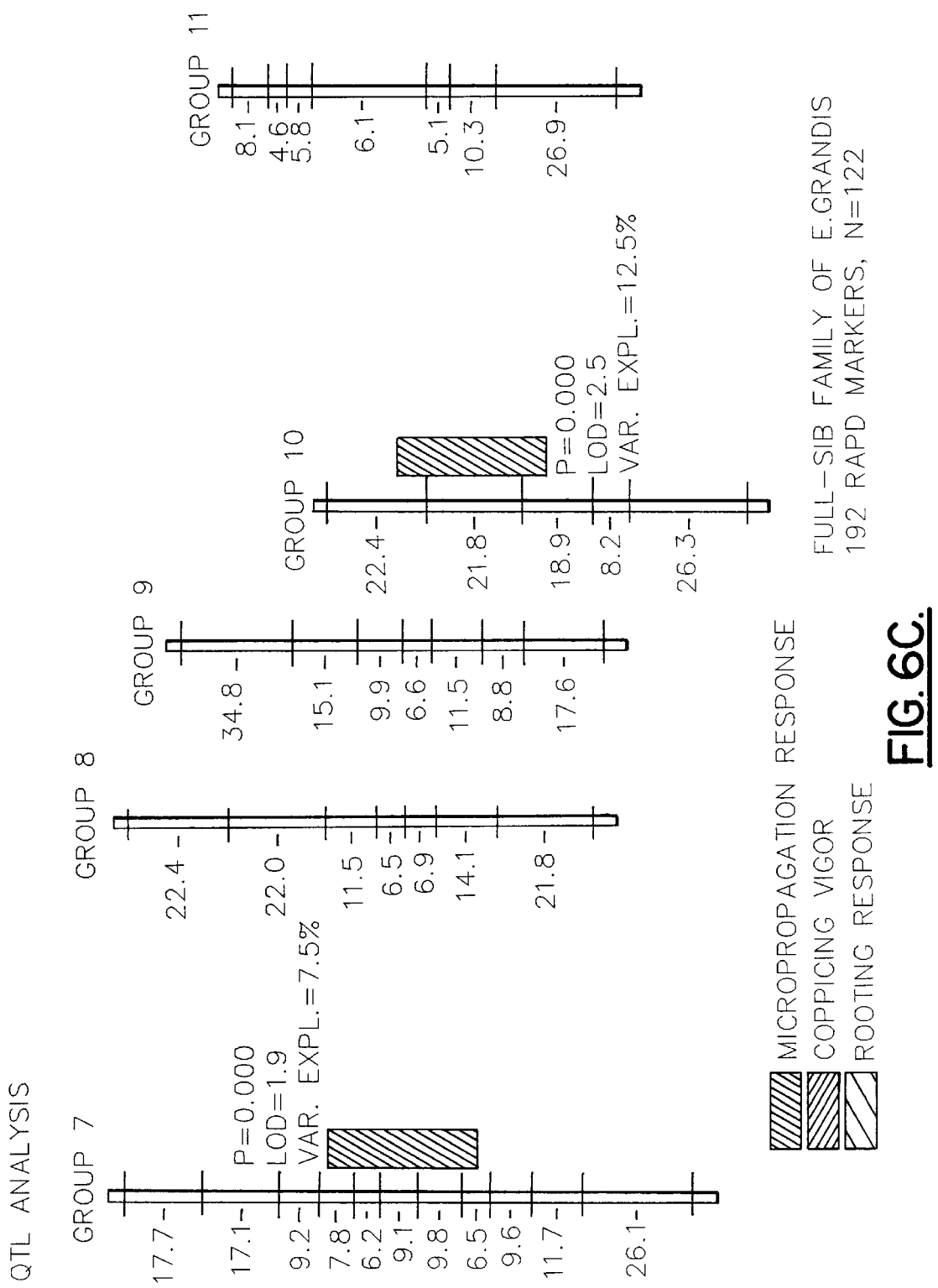

Confirmation of Inheritance and segregation of RAPD Markers: The inheritance of segregating RAPD markers from both parents following the pseudo-testcross configuration was confirmed by DNA hybridization experiments (FIGS. 5 and 6). A case of allelism between RAPD fragments in the two parents was tested and confirmed using DNA hybridization. In *E. grandis*, the RAPD Marker G14_927/3 is present in one allelic form with a fragment size of 927 bp. In *E. urophylla*, the same marker is present in two allelic forms, again a 927 bp fragment and a second allele with 960 bp. In the F1 a 1:1 segregation is observed for the 960 bp allele versus the heterozygous genotype with both alleles. The hypothesized allelism between the two 927 bp bands in the two parents, and the 960 band in *E. urophylla* was confirmed by probing the RAPD gel blot with 927 bp RAPD fragment from *E. grandis*, and detecting signal in all three alleles (FIGS. 5, panel A). The same principle was used to confirm the homology of markers that segregated 3:1. Both parents showed bands of equivalent size, and the progeny showed a segregation ratio that fit a 3:1. DNA hybridization of the RAPD gel both with a fragment from one of the parents confirmed the hypothesis (FIG. 5, panel B). A total of 11 markers were found in this configuration, i.e., present in both parents in a heterozygous state therefore segregating 3:1 in the progeny. Those markers were not included in the linkage analysis and map construction. Such markers once genotyped on a larger sample of individuals could be helpful to define homologies between linkage groups in the two maps and, if one wishes, to partially merge the maps into one. For this task, however, codominant markers such as RFLP's or isozymes would be preferable.

Codominant (size-variant) RAPD Markers: Although rare, codominant (size-variant) RAPD markers were found on both maps. Codominant RAPD markers can result from small insertions or deletions between priming sites (Williams et al., *Methods Enzymol.* (1992)). Codominant RAPD's were initially hypothesized from the following observation: (i) both allelic fragments are present in the same parent and are amplified with the same primer; (ii) F1 individuals received either one or the other allele, i.e., the two RAPD fragments are in repulsion; and (iii) no recombinant genotypes are observed in the F1, i.e., no individuals with both fragments or null for both fragments. In *E. grandis* four marker pairs fit these observations: A10_635/562 (group 5); A11_980/920 (group 7); Y17_525/515 (group 8); Y15_760/740 (group 11). In *E. urophylla* also four pairs were found: U7 1100/850 (group 3); Y20_400/390 (group 5) U13_350/320 (group 5); Z11_550/480 (group 6). DNA hybridization experiments confirmed the codominance of such sets of markers (FIG. 6, panel C). Several pairs of RAPD markers were observed that satisfied all the observations outlined above except that the two fragments were amplified with different primers (e.g., in *E. grandis* the pair K9_884/3 and K19_448/3 on group 4). For this category of tightly linked markers in repulsion, no DNA hybridization experiments were carried out. Functionally, as point out originally by Williams et al. (1990) such pairs of markers could also be used as single codominant marker. Overall, however, the frequently of truly codominant and functionally codominant RAPD markers for the Eucalyptus species surveyed remains below 3 percent.

Survey of the Presence and Allelic State of RAPD Markers in Different Individuals: A subset of markers from the *E. grandis* clone 44 map were surveyed for their presence and allelic state in a second individual tree of the same species (*E. grandis* 816/2) by analyzing their segregation in a second F1 progeny set involving 816/2 as a parent. From a total of 112 RAPD markers surveyed, 37 (33 percent) were found to amplify in the second tree. Of these, 20 were also in a heterozygous state and segregated 1:1 in the F1, while 17 were homozygous, i.e., did not segregate. DNA hybridization experiments were carried out for 5 markers that were not shared (FIG. 6, panel A), and 10 that were shared confirming the homology (FIG. 6, panels B and C). Only one marker of the ones tested, was found to be misinterpreted, i.e., the RAPD bands were scored as being the same but in fact were not homologous. This was a relatively large (1500 bp) fragment). Misinterpretations of this kind are more likely for larger fragments that are not as efficiently size fractionated in the electrophoretic conditions used as smaller fragments. In carrying out this kind of RAPD marker survey it is imperative that gels be run for at least 15 cm in length.

Similar survey had been originally planned for *E. urophylla*. However, after surveying 34 randomly chosen RAPD markers of *E. urophylla* clone 28, it was found that all of them were present in what was though to be a different individual of the same species. Moreover, all the markers surveyed also segregated in the second F1 progeny. The possibility that the same *E. urophylla* clone 28 had actually been used as the male parent in the second cross was tested and confirmed. A subset of five markers that were recombinationally unseparated in a locus cluster on group 5 (defined by marker U13_350/2) and a second subset of four markers in a locus cluster on group 8 (defined by marker M4_477/2) were surveyed for linkage on a set of 16 progenies. All the markers were found to be present and no recombinants were found. Further DNA hybridization experiments also confirmed that in fact the same *E. uro-* *phylla* (clone 28) had been used as the male parent in both crosses (data not shown). This result did not allow us to explore the extent of conservation of RAPD markers in different individuals of *E. urophylla*, however, it was useful to confirm the stable behavior of RAPD markers in terms of segregation and linkage relationships in a second cross involving the same individual tree.

Figure 7A:
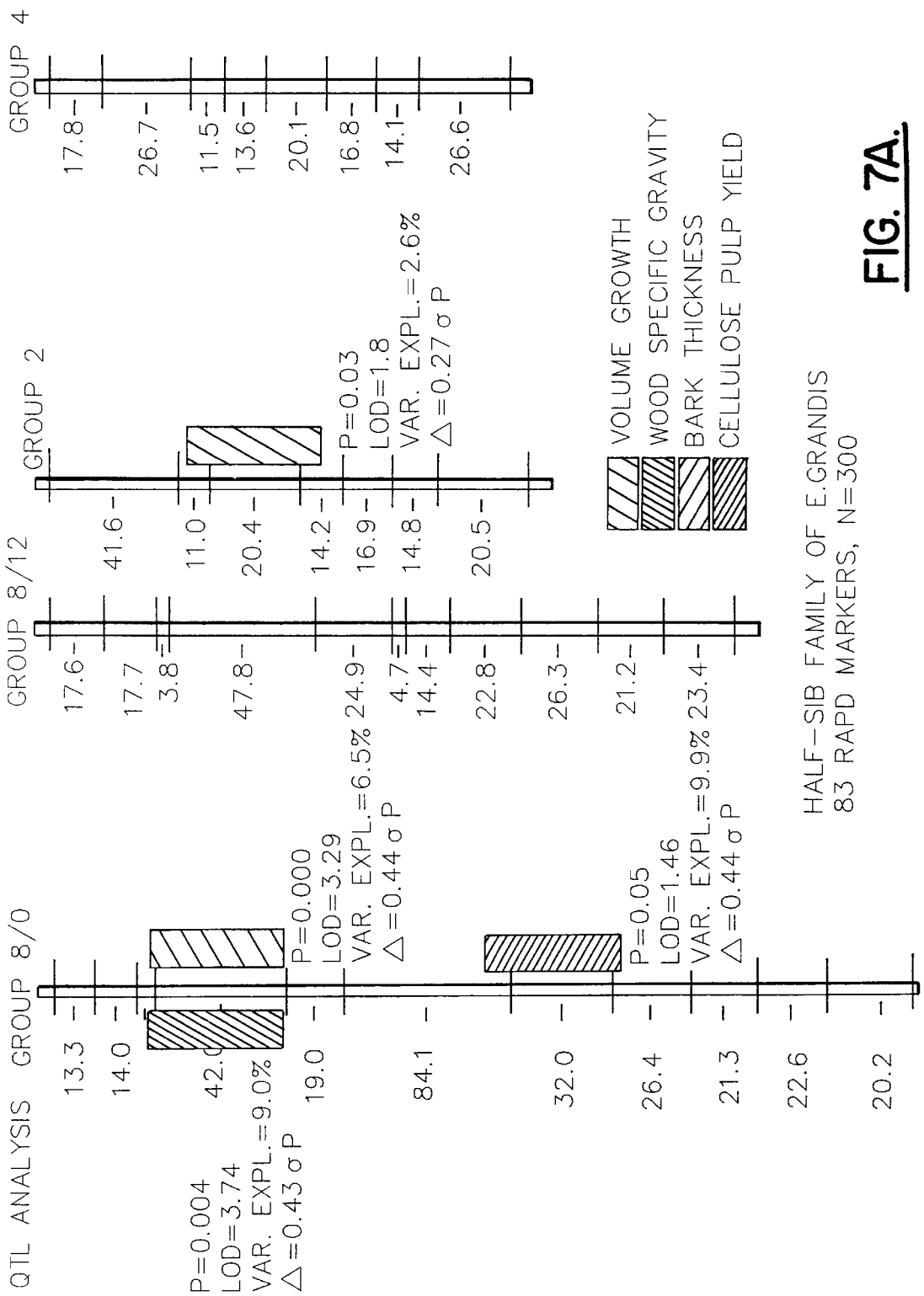
FIGS. 7A–7C together comprise a genomic map of an *E. grandis* individual showing markers representing most regions of the genome, and showing the approximate locations of markers that are statistically associated with quantitative traits of progeny in a full-sib family. These regions of strong marker: trait association are indicative of the existence of one or more QTL in these regions.
Figure 7B:
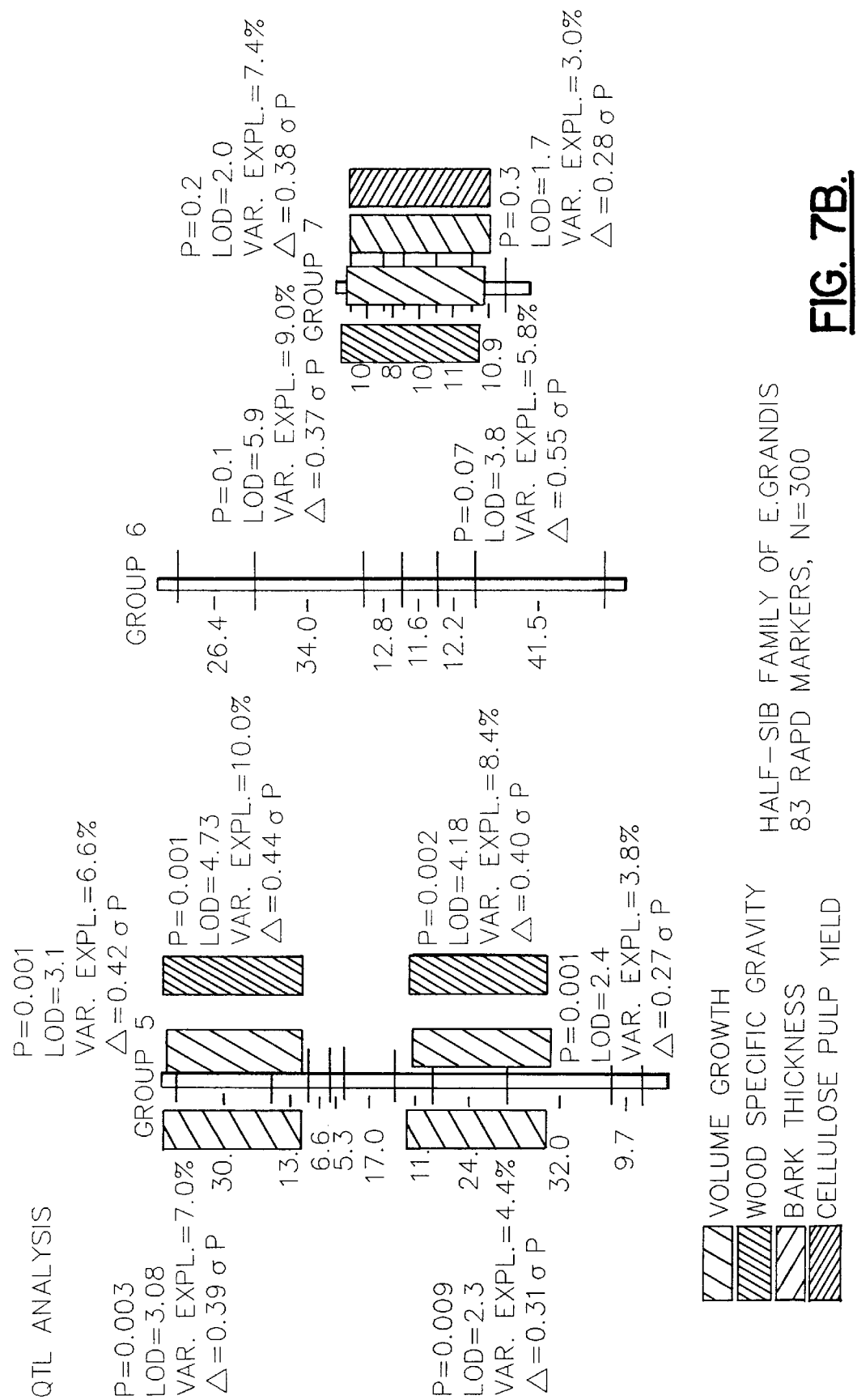
Figure 7C:
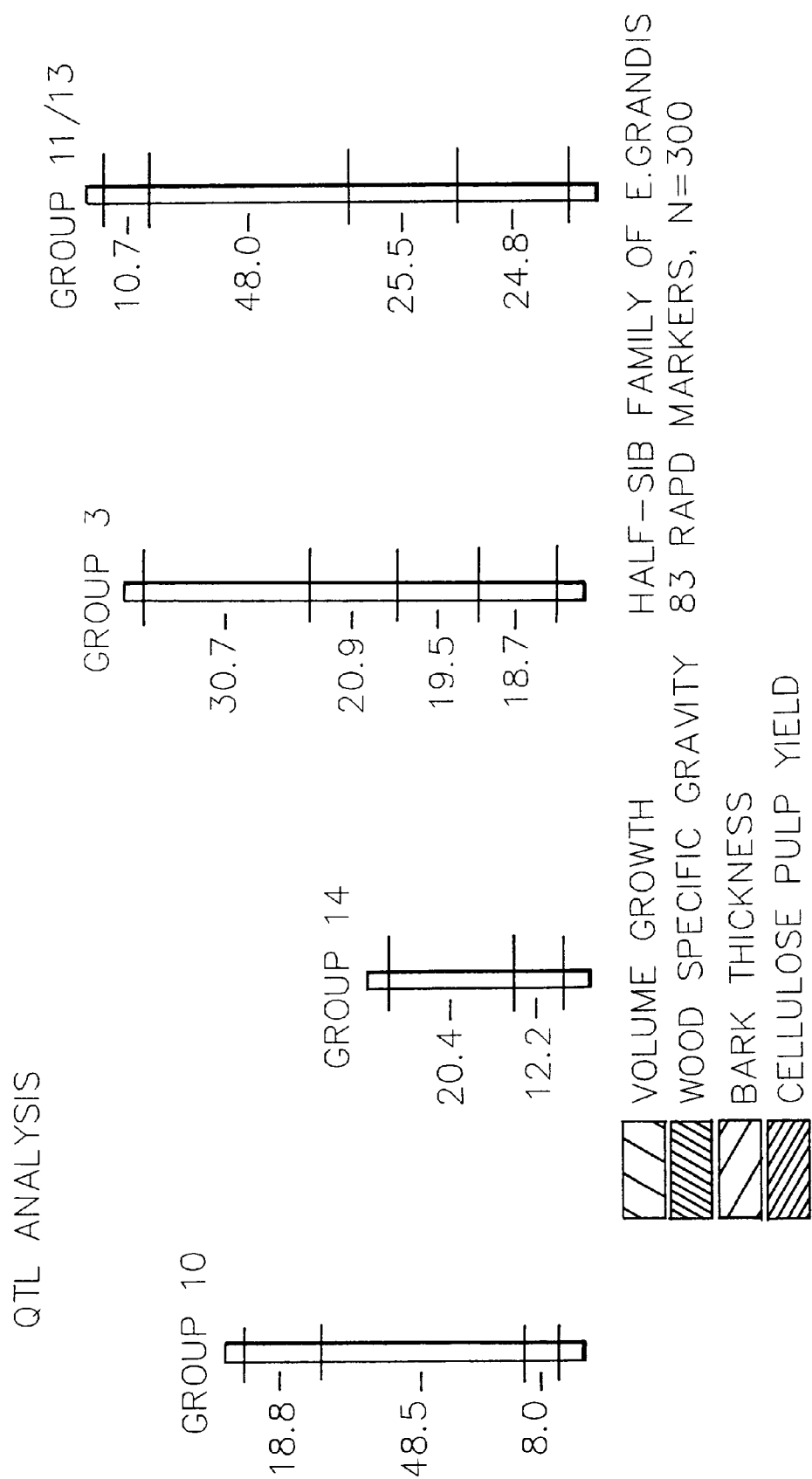

Characterization of Genomic sequence Complexity of RAPD Marker Loci: A sample of 48 RAPD fragments corresponding to 48 mapped marker loci were characterized for genomic sequence complexity in dot blot experiments (FIG. 7, panel A). Over 50 percent of the RAPD fragments were amplified from low copy genomic regions (1 to 10 copies) and less than 10 percent originated from very highly repeated regions ($\leq$1000 copies). Approximately equal frequencies (~20 percent) were found for fragments amplified from moderately repeated (10 to 100) and highly repeated regions (100 to 1000) (FIG. 7), panel B). Similar estimates of genomic sequence complexity of RAPD marker loci was observed in soybean (Williams et al., *Nucleic Acids Res.*, 18:6531–6535 (1990)) and Arabidopsis (Reiter et al., *Proc. Natl. Acad. Sci. USA*, 89:1477–1481 (1992)). Based on 48 data points, a simple correlation analysis was carried out between the following variables; RAPD fragment size in basepairs, amplification intensity score and copy number r=0.04; intensity score x copy number r=0.18. In conclusion, no significant correlation ($\alpha$=0.05) was found for any of the three pairwise analyses, suggesting no particular dependency of the fragment size or amplification efficiency of RAPD marker loci on the complexity of the genomic region sampled.

DISCUSSION

Pseudo-testcross Mapping Strategy using RAPD Markers: We have used a "pseudo-testcross" mapping strategy in combination with the RAPD assay to construct the first reported linkage maps for species of Eucalyptus. In a cross between heterozygous parents, many single-dose polymorphic markers will be heterozygous in one parent, null in the other and therefore segregate 1:1 in their progeny as in a testcross. We use the name "pseudo-testcross" for this strategy because the testcross mating configuration of the markers is not known a priori as in a conventional testcross where the tester is homozygous recessive for the locus of interest. Rather, the configuration is inferred a posteriori after analyzing the parental origin and genetic segregation of the marker in the progeny of a cross between highly heterozygous parents with no prior genetic information. When this inference is done for both parents involved in the cross, the term "two-way pseudo-testcross" is more appropriately used.

Ritter et al., *Genetics*, 125:645–654 (1990), described the theoretical background for linkage analysis of markers segregating in crosses between heterozygous parents. As mentioned in that work, map construction in allogamous plant species for which only heterozygous individuals are available can make use of single-dose polymorphic markers behaving as dominant markers in an F1, segregating 1:1 for the presence or absence of the fragment. These markers were used for genetic mapping in potato (Bonierbale et al., *Genetics*, 120:1095–1103 (1988)), and recently allowed genetic mapping in polyploid sugar can (Wu et al., *Theor. Appl. Genet.*, 83:294–300 (1992); Da Silva et al., *Genome*, 36:782–791 (1993); Sobral et al., *Theor. Appl. Genet.*, 86:105–112 (1993); Al-Janabi et al., *Genetics*, 134:1249–1260 (1993)). We and others observed this same mating configuration when analyzing genetic segregation of RAPD markers in F1 crosses of forest and fruit trees, and suggested its wide applicability for genetic mapping in this group of highly heterozygous largely undomesticated species (Carlson et al., *Theor. Appl. Genet.*, 83:194–200 (1991); Grattapaglia et al., Section 2.02–08 Cali, Colombia (in press), (1992); Roy et al., *Theor. Appl. Genet.*, 85:173–180 (1992); Lawson et al., Conference on the Plant Genome I, San Diego, Calif. (1992)).

The pseudo-testcross mapping strategy is conceptually simple to implement and can be applied with any type of molecular marker. However, its potential can be better explored with the efficiency of the RAPD assay in prescreening marker polymorphisms in search of the informative test cross configurations. The fact that the RAPD assay is sensitive to single base changes, contributes to a higher efficiency in scanning the genomes for polymorphisms. Moreover, the fact that RAPD detects only one allele at a locus, facilitates the occurrence of pseudo-testcross configurations since the necessary null genotype of one of the parents actually corresponds to undetected alleles. In addition to that, the RAPD assay is technically simple and fast to perform facilitating the initial screening step. Following our screening procedure in Eucalyptus, 36 arbitrary primers could be easily screened in a single working day, yielding an estimated 1.82 markers/primer, i.e. 65 markers from both parents taken together. Finally, the segregation ratio observed for a dominant RAPD marker in this configuration has the same information content as that of a codominant marker. Evidently, a highly polymorphic, multi-allelic marker that detected all four allelic variants of the mating configuration, (e.g., sequence tagged microsatellite site), would contain more genetic information (M. Morgante and A. M. Olivieri) *The Plant Journal* 3: 175–182 (1993).

The use of RAPD markers in a pseudo-testcross configuration is a general strategy for the construction of genetic linkage maps in outbred forest trees as well as in any highly heterozygous living organisms. It can be immediately applied to any species without prior genetic information. The only requirements are sexual reproduction between two individuals that results in the generation of a progeny large enough to allow the estimation of recombination frequencies between segregating markers. Its efficiency will be directly proportional to the level of genetic heterozygosity of the species under study, which is a function of the mating system, and the genetic divergence between the individuals crossed. In our study we employed an interspecific cross between highly heterozygous individuals from two closely related outcrossing species, thus increasing the probability of finding a pseudo-testcross marker configurations. We only found 11 markers heterozygous in both parents thus segregating 3:1 compared to 558 markers in a test cross configuration, segregating 1:1.

The pseudo-testcross strategy should also be efficient at the intraspecific level and increasingly so with crosses of genetically divergent individuals from geographically distinct origins. In a survey of 112 mapped markers, we found that only 33 percent were shared between two individuals of the same species and different provenances. We suggest that at the intraspecific level, the mapping efficiency of the pseudo-testcross strategy, measured by the number of informative markers/arbitrary primer should reach between 60 to 70 percent of the one reported in this study, that is –2.4 instead of 3.69 markers/selected primer. With individuals form the same population, this number will tend to be lower, as more markers will be shared. In a group of 38 heterozygous clones of *Solanum tuberosum* the informativeness of RFLP probes for direct segregation analysis of F1 populations varied from 49 to 95 percent indicating that linkage mapping using F1 progeny should be feasible for most combinations (C. Gebhardt, et al.) *Theor. Appl. Genet.* 78: 65–75 (1989). Test cross RAPD marker configurations were often observed at the intraspecific level in other highly heterozygous forest tree species, however no estimates of frequencies per arbitrary primer were given (J. E. Carlson, et al.) *Theor. Appl. Genet.* 83: 194–200 (1991); E. Roy, et al.) *Theor. Appl. Genet.* 85: 173–180 (1992).

The pseudo-testcross strategy basically extends the haploid mapping approach used for conifers, to any other angiosperm tree species. The final results is essentially the same, i.e. linkage maps for individual trees, however it requires performing a controlled cross. On the other hand it is more time and cost efficient since gametic segregation from two individuals or twice the heterozygosity is surveyed simultaneously in the same PCR reaction, both in the primer screening and in the mapping phase. Therefore, even in conifers, the pseudo-testcross could potentially be the mapping strategy of choice for quickly generating single-tree linkage maps.

Genetic linkage maps of single individuals: The genetic linkage maps constructed in this study (FIGS. 3 and 4) are individual specific. The pseudo-testcross strategy is specifically based on the selection of single-does markers present in one parent and absent in the other. Therefore no mapped RAPD markers are in common between the two maps and so it is impossible at this point, to determine homologies of linkage groups in the two maps or integrate the two maps into one. Overlap of RAPD marker occurrence and linkage relationships in genetic maps of different individuals will depend on the presence of the same RAPD marker loci and their allelic state. While at the interspecific level, the overlap will be very low, at the intraspecific level, it will be increasingly high as individuals from the same population are used. In this study we found that 33 percent of the mapped makers in *E. grandis* were present in a second individual of the same species but from a very distinct origin, and 54 percent of those were also in a heterozygous state. Indirect evidence for the occurrence of the same RAPD markers across different individuals of the same population come also from studies that employed RAPD markers to estimate outcrossing rates in stands of *E. urophylla* (D. Grattapaglia, D. O'Malley and R. R. Sederoff) Proceedings of IUFRO International Conference, Section 2.02–08 Cali, Columbia (1992), and *Datisca glomerata* (P. Fritsch and L. H. Rieseberg) *Nature* 359: 633–636 (1992).

To integrate linkage maps constructed by the pseudo-testcross strategy, codominant markers will alleles segregating from both parents would be necessary, providing a set of common loci which would be used as locus bridges. More than 50 percent of the RAPD fragments mapped in this study are low-copy, and could potentially be used to detect codominant RFLP's. While such markers could be helpful in connecting linkage groups, a complete map merging would still be fairly problematic to achieve, since correct locus ordering among all the markers within a bridged linkage group would not be known (B. H. Liu, personal communication). Furthermore, map merging is potentially unnecessary in the context of the breeding applications envisaged for these linkage maps in forest tree breeding (see below).

No morphological traits or other single gene traits that could potentially be placed on these maps, segregated in the population used for map construction. To our knowledge no simply inherited traits are presently known in Eucalyptus that could be place on any genetic map, with the exception of isozyme loci. The same screening procedure with parents and a subset of progeny could be used for mapping isozyme loci. Informative configurations of isozymes genotypes in the parents would result in either 1:1 or 1:2:1 segregation ratios in the F1, and mapping of the isozyme locus could be achieved in only one or both maps respectively. The existing RAPD linkage maps provide a scaffold where even distant linkage relationships of isozymes could be determined. On the other hand, isozyme loci would provide anchor loci for single-tree map comparisons and merging.

We obtained equivalent genome coverages on the two maps in spite of different estimates of total map distances. This suggests that the difference in total map distance observed between the two species and sexes are biologically significant. However no distinction is possible at this point between a species specific, sex specific or individual specific difference in genetic recombinations. If applied within species, however, the pseudo-testcross strategy should provide a valuable tool to study specific differences in general recombination rate. Genome sizes estimated in our study are well within the range of several other species (listed by R. O. Nodari, et al.) Theor. Appl. Genet. 85: 513–520 (1993). However, genome coverages found in our study are slightly higher than those found in other maps. A good comparative example in this respect is common bean, that has genome characteristics similar to eucalyptus, (n=11 chromosomes; genome size around 600 Mbp). Approximately 80 percent of the genome could be covered with a framework map of 145 RFLP loci (C. E. Vallajos, et al.) Genetics 131: 733–740 (1992). Besides intrinsic biological differences in levels of DNA polymorphism and rates of recombination, one of the possible reasons for the observed difference in genome coverage could be the result of a more efficient genome sampling by RAPD markers as compared to the RFLP technique, particularly for genomic regions rich in repetitive DNA.

Framework maps of RAPD marker loci that could be ordered with a likelihood ratio support $\geq 1000:1$ were presented (FIGS. 3 and 4). Markers loci that could not be ordered with equal confidence constitute accessory markers on the map, and are assigned to already mapped loci. This presentation of the data is convenient for selecting a subset of evenly spaced framework markers to initially scan the genome for QTL mapping. Recent simulation studies have shown that wide marker spacings of 20 or even 50 cM are optimal for this task (Darvasi, et al. 1993). A more focused search for the exact position of QTL's can then be done with the available nearby accessory markers. If more markers are still needed in a region of interest, genetic walking based on a genotype pooling techniques could be used (R. W. Michelmore, et al.) Proc. Natl. Acad. Sci. USA 88:9828–9832 (1991); (J. J. Giovannoni, et al.) Nucl. Acid. Res. 19: 6553–6558 (1991); (R. S. Reiter, et al.) Proc. Natl. Acad. Sci. USA 89: 1477–1481 (1992).

Genome complexity of mapped RAPD maker loci: Eucalyptus grandis and E. Urophylla have a typical angiosperm haploid genome size ($7 \times 10^8$ bp) (D. Grattapaglia and H. D. Bradshaw, Jr.) Can. J. For. Res. 24: 1074–1078 (1994). In this context, approximately 70 to 80 percent of the genome should correspond to repetitive DNA (B. Lewin) Oxford University Press, Oxford (1990). If the RAPD assay sampled the genome randomly, this repetitive/nonrepetitive ratio should be reflected in the ratio between fragments containing high and low copy sequences. We found, however, that over 50 percent of the RAPD fragments characterized, amplified from low copy regions (1–10 copies). It is important to point out that the sample of RAPD fragments surveyed in this experiment are not randomly chosen RAPD fragments, rather they correspond to a selected subset of fragments that behave as genetic markers thus segregating in a mendelian fashion, mapping to a single location and therefore originating from a unique site in the genome defined by a pari of ten-basepair priming sites and the size of the amplified fragment.

These results suggest that when assaying a genome for RAPD genetic markers a skewed sampling toward low-copy genomic regions takes place probably reflecting the requirement for the amplification site to be unique in the genome. Such sites are more likely to occur in non-repetitive then repetitive regions. If most structural genes lie in non-repetitive genomic regions, the majority of the RAPD markers indicated on the maps amy be physically very close to genes. Given their molecular nature (amplification from inverted repeat units), it is likely that they are amplified from non coding DNA stretches such as introns as well as 5' and 3' untranslated regions. This argument will depend on the distribution of genes in the Eucalyptus genome which is presently unknown. (J. L Wolff, et al.) Braz. J. Genet. 16: 431–439 (1993) screened PstI genomic libraries of E. grandis and E. urophylla and found that 60 percent of the probes detected RFLP's, and 80 percent of those detected a simple polymorphism pattern. Thus approximately 48 percent of the genomic clones tested were useful as RFLP probes. In our study we found that 53 percent of the RAPD fragments are amplified from low copy regions and could potentially be used as RFLP probes. In Eucalyptus, these results indicate that in terms of usefulness for RFLP analysis, the genomic library of RAPD fragments obtained as a byproduct of this mapping experiment, closely resembles a genomic library constructed by the traditional approach. RAPD fragments as probes would be very convenient since they could be easily reamplified without cloning.

The foregoing is illustrative of the present invention and is not to be construed as limiting thereof. The invention is defined by the following claims, with equivalents of the claims to be included therein.

TABLE 2

| SEQ ID: | PRIMER | SEQUENCE (5' → 3') |
|---|---|---|
| 1 | OPB8 | CTCCACACGG |
| 2 | OPK1 | CATTCGAGCC |
| 3 | OPD11 | AGCGCCATTG |
| 4 | OPJ7 | CCTCTCGACA |
| 5 | OPJ4 | CCGAACACGG |
| 6 | OPC12 | TGTCATCCCC |
| 7 | OPK17 | CCCAGCTGTG |
| 8 | OPC6 | GAACGGACTC |
| E. urophylla: Rooting markers | | |
| 9 | Z12 | TCAACGGGAC |
| 10 | Q13 | GGAGTGGACA |
| 11 | W11 | CTGATGCGTG |
| 12 | K3 | CCAGCTTAGG |
| E. grandis: Coppicing vigor | | |
| 13 | U16 | CTGCGCTGGA |
| 14 | K10 | GTGCAACGTG |
| 15 | V2 | AGTCACTCCC |
| 16 | Y3 | ACAGCCTGCT |
| 17 | P10 | TCCCGCCTAC |
| Half-sib primers: Volume markers | | |
| 18 | R4 | CCCGTAGCAC |
| 19 | X1 | CTGGGCACGA |
| 20 | V7 | GAAGCCAGCC |
| 21 | Y17 | GACGTGGTGA |
| 22 | A11 | CAATCGCCGT |
| 23 | V10 | ACCTCGGCAC |
| 24 | V10 x2 | TTCCGCCACC |
| Half-sib primer: WSG | | |
| 25 | Y15 | AGTCGCCCTT |
| Half-sib primer: Pulp | | |
| 26 | Z18 | AGGGTCTGTG |

That which is claimed is:

1. A method of determining whether a quantitative trait is a heritable oligogenic trait in a family of trees of the genus Eucalyptus, comprising the steps of:
   (a) choosing a sexuall mature forest tree parent plant;
   (b) obtaining a plurality of progeny of said parent plant by performing self or cross-pollinations, said parent and said progeny together comrising a plant family, said progeny being selected from the group conststing of full sib progeny, half-sib progeny, and selfed progeny;
   (c) constructing a genomic map of said plant family using a plurality of Random Amplified Polymorphic DNA (RAPD) markers, said RAPD markers segregating in an essentially Mendelian ratio and showing linkage with other markers;
   (d) grouping said progeny into classes based on the allelic state of a RAPD marker;
   (e) measuring said quantitative trait in each of said progeny;
   (f) determinig the mean of said quantitative trait in each of said classes of progeny; and
   (g) determining statistically whether said means of said classes differ significantly, wherein a signifcant difference among means of said classses indicates said trait is a heritable oligogenic trait.

2. The method of claim 1, further comprising repeating steps (d)–(g) for additional RAPD markers.

* * * * *